US012613622B1

(12) United States Patent
Appelbaum et al.

(10) Patent No.: US 12,613,622 B1
(45) Date of Patent: Apr. 28, 2026

(54) METHOD AND SYSTEM FOR MANAGING LIFESTYLE AND HEALTH INTERVENTIONS

(71) Applicant: Click Therapeutics, Inc., New York, NY (US)

(72) Inventors: Kevin Appelbaum, Corte Madera, CA (US); Mark Berman, San Francisco, CA (US); Andres Camacho, Lafayette, CA (US); Sourav Dey, South San Francisco, CA (US)

(73) Assignee: Click Therapeutics, Inc., New York, NY (US)

( * ) Notice: Subject to any disclaimer, the term of this patent is extended or adjusted under 35 U.S.C. 154(b) by 0 days.

(21) Appl. No.: 18/925,785

(22) Filed: Oct. 24, 2024

Related U.S. Application Data

(63) Continuation of application No. 15/963,994, filed on Apr. 26, 2018, now abandoned.
(Continued)

(51) Int. Cl.
*G16H 20/30* (2018.01)
*G06F 3/0484* (2022.01)
(Continued)

(52) U.S. Cl.
CPC ........... *G06F 3/0484* (2013.01); *G16H 20/30* (2018.01); *G16H 20/60* (2018.01); *A61B 5/0022* (2013.01); *G16H 50/30* (2018.01)

(58) Field of Classification Search
None
See application file for complete search history.

(56) References Cited

U.S. PATENT DOCUMENTS

| | | | |
|---|---|---|---|
| 7,935,307 B2 | 5/2011 | Angelides | |
| 8,066,640 B2 | 11/2011 | Angelides | |

(Continued)

FOREIGN PATENT DOCUMENTS

| | | | |
|---|---|---|---|
| WO | WO-2017/106770 A1 | 6/2017 | |
| WO | 2020/061562 A1 | 3/2020 | |
| WO | 2020/247032 A1 | 12/2020 | |

OTHER PUBLICATIONS

Berman et al.: "FareWell and the How of Lifestyle Medicine", American Journal of Lifestyle Medicine, vol. 11, No. 4, Apr. 6, 2017 (Apr. 6, 2017), pp. 314-317, XP009506081, DOI: 10.1177/1559827617701411.
(Continued)

*Primary Examiner* — Rinna Yi
(74) *Attorney, Agent, or Firm* — MORRISON & FOERSTER LLP

(57) ABSTRACT

Provided herein are systems and methods for communicating with user devices over networked environments. A server may provide, to a user device over a communication network, an instruction to present a graphical user interface (GUI) on a user device to prompt a user to input values for event parameters for events on the user device according to a data protocol. The server may receive, from the user device, a plurality of values for a plurality of event parameters The server may determine, based on inputting via the GUI, a metric. The server may apply the plurality of values and the metric into a machine learning model to generate a likelihood to satisfy a target associated with the data protocol. The server may, responsive to the likelihood not satisfying a threshold, transmit a subsequent instruction.

14 Claims, 24 Drawing Sheets

Related U.S. Application Data

(60) Provisional application No. 62/492,065, filed on Apr. 28, 2017, provisional application No. 62/628,842, filed on Feb. 9, 2018, provisional application No. 62/629,644, filed on Feb. 12, 2018.

(51) Int. Cl.
| | |
|---|---|
| *G16H 20/60* | (2018.01) |
| *A61B 5/00* | (2006.01) |
| *G16H 50/30* | (2018.01) |

(56) References Cited

U.S. PATENT DOCUMENTS

| | | | |
|---|---|---|---|
| 8,568,309 | B2 | 10/2013 | Angelides |
| 8,812,244 | B2 | 8/2014 | Angelides |
| 8,838,513 | B2 | 9/2014 | Sudharsan |
| 9,064,040 | B2 | 6/2015 | Sudharsan |
| 9,516,053 | B1* | 12/2016 | Muddu ............... G06F 16/9024 |
| 9,536,053 | B2 | 1/2017 | Sudharsan |
| 9,754,077 | B2 | 9/2017 | Sysko et al. |
| 9,817,559 | B2 | 11/2017 | Simon et al. |
| 9,824,190 | B2 | 11/2017 | Sudharsan |
| 9,858,394 | B2 | 1/2018 | Sudharsan |
| 9,881,136 | B2 | 1/2018 | Sysko et al. |
| 9,992,292 | B2 | 6/2018 | Gunnarsson et al. |
| 10,152,675 | B2 | 12/2018 | Sudharsan |
| 10,176,893 | B2 | 1/2019 | Sysko et al. |
| 10,192,638 | B2 | 1/2019 | Sysko et al. |
| 10,319,477 | B1 | 6/2019 | Bill |
| 10,672,509 | B2 | 6/2020 | Sudharsan |
| 10,748,658 | B2 | 8/2020 | McRaith et al. |
| 10,818,389 | B2 | 10/2020 | Sysko et al. |
| 10,839,951 | B2 | 11/2020 | Sysko et al. |
| 10,846,607 | B2 | 11/2020 | Sysko et al. |
| 10,854,337 | B2 | 12/2020 | McRaith et al. |
| 10,860,943 | B2 | 12/2020 | Sysko et al. |
| 10,872,686 | B2 | 12/2020 | Sysko et al. |
| 10,978,207 | B2 | 4/2021 | McRaith et al. |
| 11,355,228 | B2 | 6/2022 | Appelbaum et al. |
| 2007/0072156 | A1 | 3/2007 | Kaufman et al. |
| 2007/0288266 | A1 | 12/2007 | Sysko et al. |
| 2008/0299009 | A1 | 12/2008 | Angelides |
| 2009/0264337 | A1 | 10/2009 | Angelides |
| 2010/0191075 | A1 | 7/2010 | Angelides |
| 2011/0046519 | A1 | 2/2011 | Raheman |
| 2011/0119075 | A1 | 5/2011 | Dhoble |
| 2011/0125519 | A1 | 5/2011 | Dhoble |
| 2011/0125520 | A1 | 5/2011 | Dhoble |
| 2012/0029327 | A1 | 2/2012 | Angelides |
| 2012/0231431 | A1 | 9/2012 | Angelides |
| 2013/0035563 | A1 | 2/2013 | Angelides |
| 2013/0078601 | A1 | 3/2013 | Angelides |
| 2013/0110551 | A1 | 5/2013 | Bingol |
| 2013/0117040 | A1 | 5/2013 | James et al. |
| 2013/0187780 | A1 | 7/2013 | Angelides |
| 2013/0216989 | A1 | 8/2013 | Cuthbert |
| 2014/0052475 | A1 | 2/2014 | Madan et al. |
| 2014/0074454 | A1* | 3/2014 | Brown .................... G10L 15/08 704/235 |
| 2014/0089836 | A1 | 3/2014 | Damani et al. |
| 2014/0154653 | A1 | 6/2014 | Angelides |
| 2014/0214442 | A1 | 7/2014 | Duffy et al. |
| 2014/0214443 | A1 | 7/2014 | Duffy et al. |
| 2014/0222454 | A1 | 8/2014 | Duffy et al. |
| 2014/0278474 | A1* | 9/2014 | McClure ............... G16H 40/67 705/2 |
| 2014/0363794 | A1 | 12/2014 | Angelides |
| 2015/0079561 | A1 | 3/2015 | Petakov et al. |
| 2015/0281384 | A1 | 10/2015 | Gunnarsson et al. |
| 2015/0288797 | A1 | 10/2015 | Vincent |
| 2015/0313529 | A1 | 11/2015 | Nevo et al. |
| 2015/0371007 | A1 | 12/2015 | Cederlund et al. |
| 2016/0012342 | A1 | 1/2016 | Simon et al. |
| 2016/0321935 | A1* | 11/2016 | Mohler .................... G09B 5/08 |
| 2016/0324463 | A1 | 11/2016 | Simpson et al. |
| 2017/0076630 | A1 | 3/2017 | Angelides et al. |
| 2017/0080288 | A1* | 3/2017 | Roh ..................... A61B 5/6898 |
| 2017/0109479 | A1 | 4/2017 | Vemireddy et al. |
| 2017/0162069 | A1 | 6/2017 | Petakov et al. |
| 2017/0228520 | A1 | 8/2017 | Kidd et al. |
| 2017/0329917 | A1 | 11/2017 | McRaith et al. |
| 2017/0329933 | A1 | 11/2017 | Brust et al. |
| 2017/0344726 | A1 | 11/2017 | Duffy et al. |
| 2018/0180633 | A1 | 6/2018 | Volek et al. |
| 2018/0247713 | A1 | 8/2018 | Rothman |
| 2018/0277246 | A1 | 9/2018 | Zhong et al. |
| 2018/0315499 | A1 | 11/2018 | Appelbaum et al. |
| 2019/0074080 | A1 | 3/2019 | Appelbaum et al. |
| 2020/0335218 | A1 | 10/2020 | McRaith et al. |
| 2020/0383571 | A1 | 12/2020 | Fakhouri et al. |
| 2020/0383648 | A1 | 12/2020 | Bridgewater et al. |
| 2020/0388376 | A1 | 12/2020 | Kendale |
| 2020/0388381 | A1 | 12/2020 | Kozin et al. |
| 2020/0388392 | A1 | 12/2020 | Chen et al. |
| 2020/0388393 | A1 | 12/2020 | Boulos et al. |
| 2020/0388399 | A1 | 12/2020 | Kozin et al. |
| 2020/0388403 | A1 | 12/2020 | Boulos et al. |
| 2021/0035690 | A1 | 2/2021 | McRaith et al. |
| 2021/0104173 | A1* | 4/2021 | Pauley ................... G16H 20/10 |
| 2021/0272474 | A1* | 9/2021 | Geronimo-Button ........................ G16H 20/70 |
| 2022/0061775 | A1* | 3/2022 | Jepson ................. A61B 5/7267 |
| 2022/0062621 | A1* | 3/2022 | Hogg ................. A61N 1/36014 |
| 2022/0375619 | A1 | 11/2022 | Appelbaum et al. |
| 2022/0392611 | A1 | 12/2022 | Appelbaum et al. |
| 2023/0017196 | A1* | 1/2023 | Jain ....................... H04L 67/306 |

OTHER PUBLICATIONS

Berman: "Learning & Outcomes from our First Digital Therapeutic Pilot", Feb. 16, 2017 (Feb. 16, 2017), XP55484428; Retrieved from the internet: https://farewell-assets.s3.amazonaws.com/Pilot_Results_Extended_Referenced_Version.pdf [retrieved on Feb. 27, 2024].

Berman: "Learning & Outcomes From Our First Digital Therapeutic Pilot" Feb. 10, 2017, Retrieved from: https://farewell-assets.s3.amazonaws.com/Pilot_Results_Extended_Referenced_Version.pdf.

Comstock: "FareWell raises $8.5M for digital coaching weight loss service", Jun. 23, 2016; Retrieved from: https://www.mobihealthnews.com/content/farewell-raises-85m-digital-coaching-weight-lossservice.

Comstock: "Farewell raises $8.5m for Digital Coaching Weight Loss Service", MobiHealthNews, Jun. 23, 2016 (Jun. 23, 2016), XP002782054, Retrieved from the internet: https://www.mobihealthnews.com/content/farewell-raises-85m-digital-coaching-weight-loss?service [retrieved on Feb. 27, 2024].

Coughlin, et al., "Smartphone Applications for Promoting Healthy Diet and Nutrition: A Literature Review" Jacobs J Food Nutr. 2015;2(3):021. Retrieved from: https://www.ncbi.nlm.nih.gov/pmc/articles/PMC4725321/pdf/nihms-733996.pdf.

Coughlin: "Smartphone Applications for Promoting Healthy Diet and Nutrition: A Literature Review", Jacobs J Food Nutr., Jan. 25, 2016 (Jan. 25, 2016), XP55484530, Retrieved from the internet: https://www.ncbi.nlm.nih.gov/pmc/articles/PMC4725321/ [retrieved on Feb. 27, 2024].

Examination Report on EP Appl. No. 18724093.2 dated Nov. 15, 2024.

Examiner's Report for CA Appl. No. 3,061,729 dated Feb. 29, 2024.

Examiner's Report for CA Appl. No. 3,061,729 dated Mar. 19, 2024.

Final Office Action for U.S. Appl. No. 15/963,994 dated Mar. 30, 2023.

Final Office Action for U.S. Appl. No. 15/963,994 dated May 24, 2024.

Final Office Action for U.S. Appl. No. 15/963,994 dated Nov. 17, 2021.

Non-Final Office Action for U.S. Appl. No. 15/963,994 dated Apr. 28, 2022.

(56)     References Cited

OTHER PUBLICATIONS

Non-Final Office Action for U.S. Appl. No. 15/963,994 dated Feb. 19, 2021.

Non-Final Office Action for U.S. Appl. No. 15/963,994 dated Oct. 23, 2023.

Non-Final Office Action for U.S. Appl. No. 17/833,623 dated Jul. 31, 2024.

Non-Final Office Action on US No. U.S. Appl. No. 17/833,625 dated Sep. 12, 2024.

Sforzo: "A Digital Therapy using Wellcoaches Model", Blog entry; Wellcoaches, School of coaching; Mar. 13, 2017 (Mar. 13, 2017); Retrieved from the internet: https://www.wellcoachesschool.com/post/a-digital-therapy-using-wellcoaches-model [retrieved on Feb. 27, 2024].

Final Office Action on U.S. Appl. No. 17/833,623 dated May 7, 2025.

Final Office Action on U.S. Appl. No. 17/833,625 dated May 30, 2025.

Anonymous (Apr. 9, 2016. e-pub. Apr. 6, 2016). "Worldwide Trends in Diabetes Since 1980: A Pooled Analysis of 751 Population-Based Studies with 4.4 Million Participants," NCO Risk Factor Collaboration (NCO-Rise): The Lancet 387:1513-1530.

Anonymous (Apr. 2013). "Economic Costs of Diabetes in the U.S. in 2012," Diabetes Care 36(4):1033-1046.

Barnard, N.D et al. (2009). "A Low-Fat Vegan Diet and a Conventional Diabetes Diet in the Treatment of Type 2 Diabetes: A Randomized, Controlled, 74-Wk Clinical Trial," Am. J. Clin. Nutr. 89:15885-15968.

Decision to grant received for European Application No. 18724423.1, mailed on May 11, 2023, 3 pages.

European Search Report received for European Application No. 25172392.0, mailed on Aug. 8, 2025, 14 pages.

Intention to grant received for European Application No. 18724423.1, mailed on Jan. 2, 2023, 6 pages.

International Preliminary Report on Patentability received for PCT application No. PCT/US2018/029653, mailed on Nov. 7, 2019, 13 pages.

International Preliminary Report on Patentability received for PCT application No. PCT/US2018/029654, mailed on Nov. 7, 2019, 17 pages.

International search Report and written opinion received for PCT application No. PCT/US2018/029653, mailed on Jul. 18, 2018, 15 pages.

International search Report and written opinion received for PCT application No. PCT/US2018/029654, mailed on Sep. 11, 2018, 22 pages.

Invitation to Pay Additional Fees received for PCT application No. PCT/US2018/029654, mailed on Jul. 18, 2018, 16 pages.

Jenkins, D.J.A et al. (2002). "A Dietary Portfolio Approach to Cholesterol Reduction: Combined Effects of Plant Sterols, Vegetable Proteins, and Viscous Fibers in Hypercholesterolemia Metabolism," 51:1596-1604.

Krittanawong, C et al. (May 30, 2017). "Artificial Intelligence in Precision Cardiovascular Medicine," JACC Journals Archives 69(21):2657-2664.

National Diabetes Statistics Report 2017: Centers for Disease Control and Prevention, U.S. Department of Health and Human Services, URL: www.cdc.gov/diabetes/library/reports/congress/html, 16 pages.

Non-Final Office Action on U.S. Appl. No. 18/925,785 dated Apr. 10, 2025.

Non-Final Office Action on U.S. Appl. No. 18/925,785 dated Jan. 13, 2025.

Notification of Oral Proceeding received for European Application No. 18724423.1, mailed on May 23, 2022, 12 pages.

Office Action received for European Application No. 18724093.2, mailed on Jun. 14, 2022, 4 pages.

Partial OA Response dated Apr. 23, 2024, Squire Patton Boggs LLP, 6 pages.

Shahraz, S. et al. (2017, e-pub. Nov. 14, 2017). "Change in Testing, Awareness of Hemoglobin A1c Result, and Glycemic Control in US Adults, 2007-2014," JAMA 318(18):1825-1827.

Shi, Y et al. (Jun. 7, 2014, e-pub. Mar. 7, 2014). "The Global Implications of Diabetes and Cancer," Lancet 383 (9933):1947-1948.

\* cited by examiner

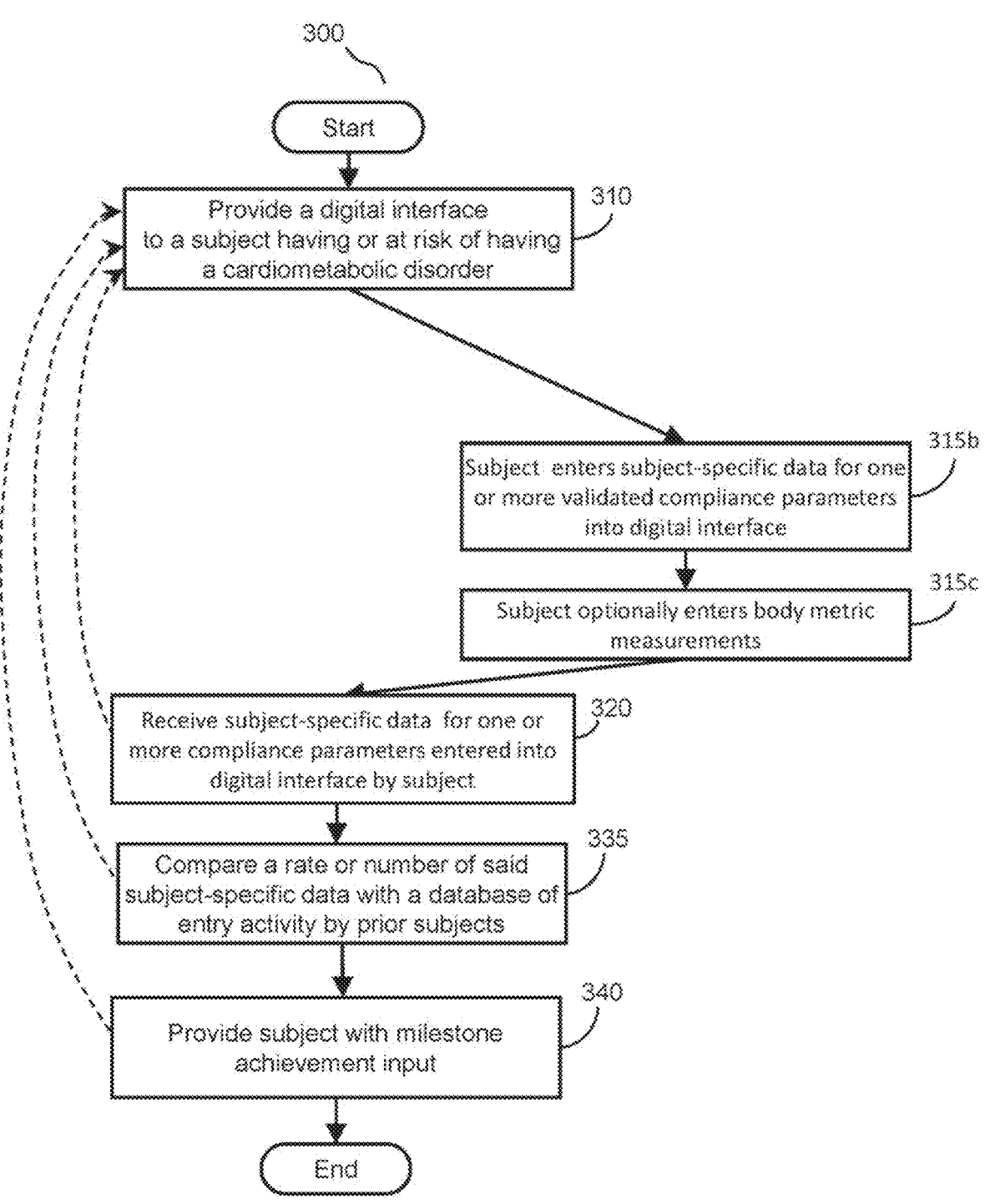

300

Start

Provide a digital interface
to a subject having or at risk of having
a cardiometabolic disorder                310

Subject enters subject-specific data for one
or more validated compliance parameters
into digital interface                315b Subject optionally enters body metric
measurements                315c Receive subject-specific data for one or
more compliance parameters entered into
digital interface by subject                320

Compare a rate or number of said
subject-specific data with a database of
entry activity by prior subjects                335

Provide subject with milestone
achievement input                340

End

FIG. 3

| | count | mean | std | min | 25% | 50% | 75% | max |
|---|---|---|---|---|---|---|---|---|
| good | 33.0 | 72.757576 | 18.525372 | 13.0 | 63.00 | 74.0 | 87.0 | 110.0 |
| bad | 36.0 | 56.972222 | 27.781274 | 8.0 | 30.75 | 54.0 | 79.5 | 107.0 | p(X|y) for total_completed_calls

| | count | mean | std | min | 25% | 50% | 75% | max |
|---|---|---|---|---|---|---|---|---|
| good | 33.0 | 6.666670 | 2.228857 | 0.0 | 6.0 | 7.0 | 8.0 | 10.0 |
| bad | 36.0 | 4.138889 | 2.231627 | 0.0 | 2.0 | 4.0 | 8.0 | 8.0 | p(X|y) for activity_target_times

| | count | mean | std | min | 25% | 50% | 75% | max |
|---|---|---|---|---|---|---|---|---|
| good | 33.0 | 19.545455 | 16.196240 | 1.0 | 5.00 | 15.0 | 30.0 | 67.0 |
| bad | 36.0 | 20.777778 | 24.749154 | 0.0 | 1.75 | 12.5 | 33.5 | 90.0 | p(X|y) for activity_fallback_falses

| | count | mean | std | min | 25% | 50% | 75% | max |
|---|---|---|---|---|---|---|---|---|
| good | 33.0 | 110.181818 | 10.097817 | 56.0 | 112.00 | 112.0 | 112.0 | 119.0 |
| bad | 36.0 | 108.111111 | 10.756467 | 56.0 | 110.25 | 112.0 | 112.0 | 118.0 | p(X|y) for meal_plan_count

| | count | mean | std | min | 25% | 50% | 75% | max |
|---|---|---|---|---|---|---|---|---|
| good | 33.0 | 176.818182 | 89.778706 | 24.0 | 119.0 | 174.0 | 228.00 | 387.0 |
| bad | 36.0 | 117.583333 | 96.662886 | 22.0 | 53.5 | 89.0 | 143.25 | 396.0 | p(X|y) for meal_target_trues

>= 5% weight loss
< 5% weight loss

| | count | mean | std | min | 25% | 50% | 75% | max |
|---|---|---|---|---|---|---|---|---|
| good | 33.0 | 153.121212 | 80.194591 | 34.0 | 93.0 | 150.0 | 188.0 | 323.0 |
| bad | 36.0 | 148.194444 | 89.421256 | 10.0 | 79.5 | 143.0 | 197.5 | 322.0 | p(X|y) for meal_fallback_trues

>= 5% weight loss
< 5% weight loss

| | count | mean | std | min | 25% | 50% | 75% | max |
|---|---|---|---|---|---|---|---|---|
| good | 33.0 | 42.090909 | 39.186544 | 0.0 | 13.0 | 32.0 | 61.00 | 159.0 |
| bad | 36.0 | 49.027778 | 39.363860 | 0.0 | 15.0 | 44.5 | 66.25 | 156.0 | p(X|y) for meal_fallback_falses

>= 5% weight loss
< 5% weight loss

FIG. 12

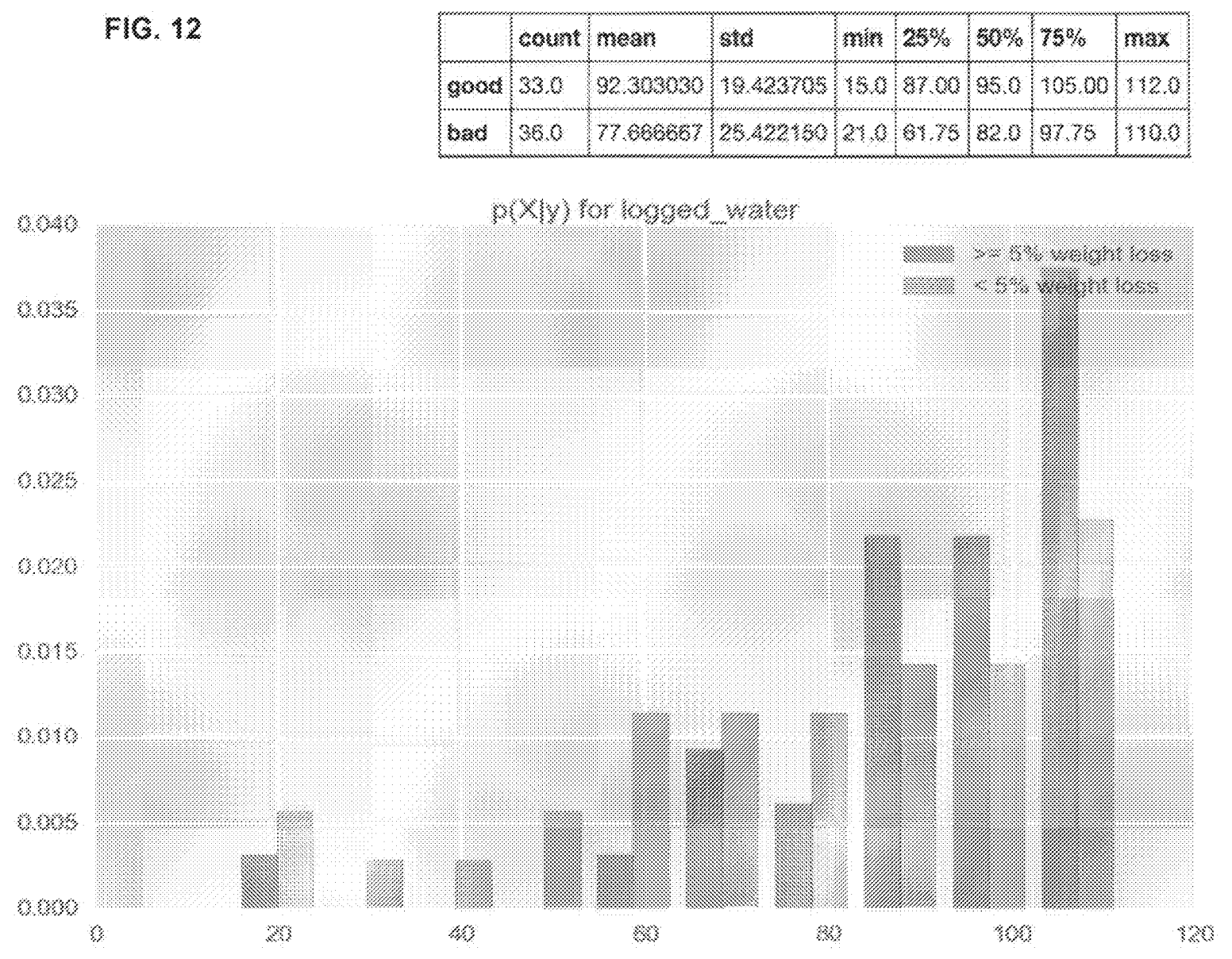

|  | count | mean | std | min | 25% | 50% | 75% | max |
|---|---|---|---|---|---|---|---|---|
| good | 33.0 | 92.303030 | 19.423705 | 15.0 | 87.00 | 95.0 | 105.00 | 112.0 |
| bad | 36.0 | 77.666667 | 25.422150 | 21.0 | 61.75 | 82.0 | 97.75 | 110.0 | p(X|y) for logged_water

>= 5% weight loss
< 5% weight loss

FIG. 13

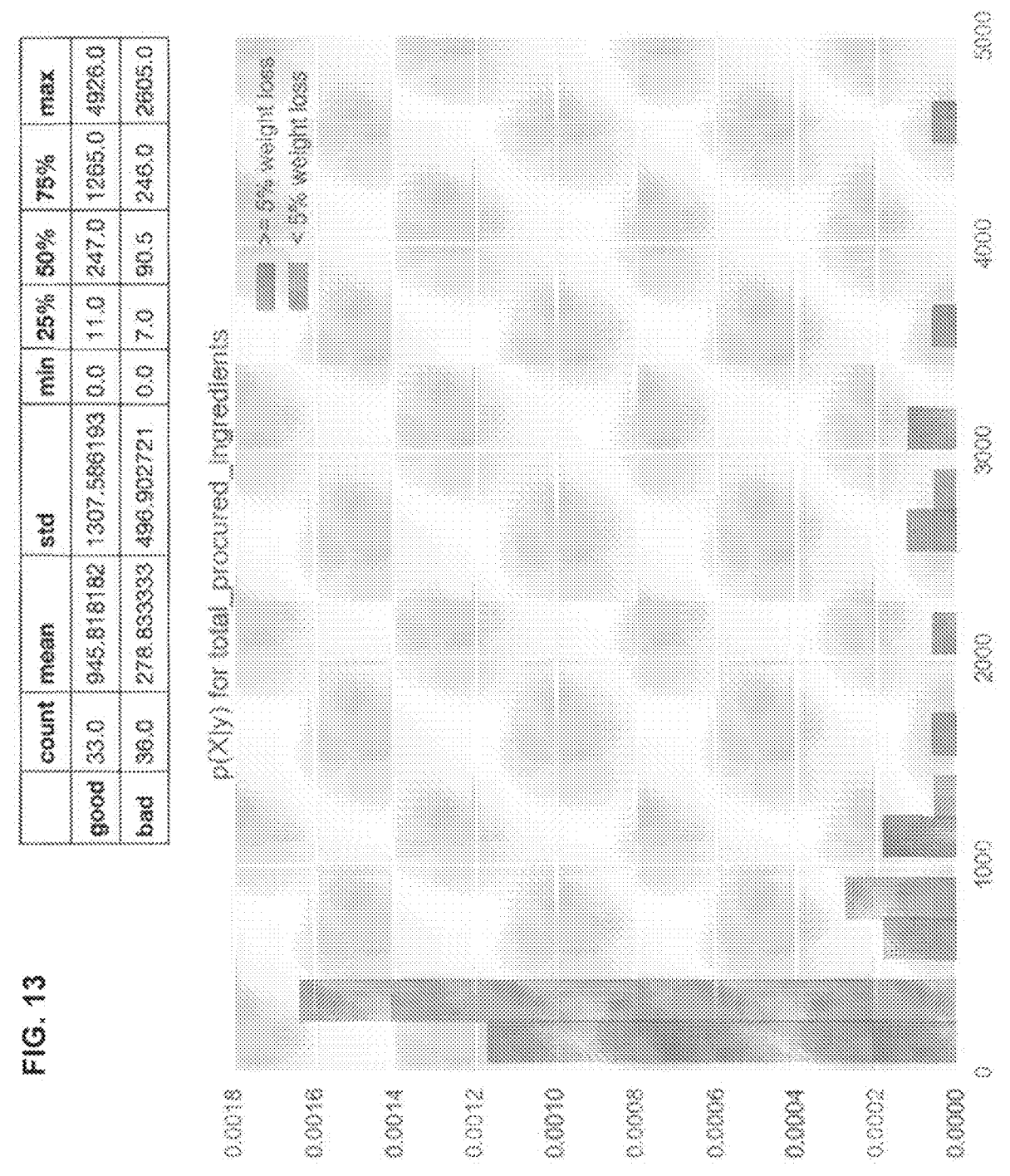

| | count | mean | std | min | 25% | 50% | 75% | max |
|---|---|---|---|---|---|---|---|---|
| good | 33.0 | 645.818182 | 1307.586193 | 0.0 | 11.0 | 247.0 | 1205.0 | 4920.0 |
| bad | 36.0 | 278.833333 | 496.902721 | 0.0 | 7.0 | 90.5 | 246.0 | 2605.0 | p(X|y) for total_procured_ingredients

>=5% weight loss

<5% weight loss

| | count | mean | std | min | 25% | 50% | 75% | max |
|---|---|---|---|---|---|---|---|---|
| good | 33.0 | 98.9696997 | 53.124560 | 7.0 | 59.0 | 95.0 | 127.0 | 207.0 |
| bad | 36.0 | 64.361111 | 48.054822 | 12.0 | 30.5 | 47.5 | 88.5 | 188.0 | p(X|y) for weight_check_count

METHOD AND SYSTEM FOR MANAGING LIFESTYLE AND HEALTH INTERVENTIONS

CROSS REFERENCE TO RELATED PATENT APPLICATIONS

This application is a continuation of U.S. patent application Ser. No. 15/963,994, filed Apr. 26, 2018, and claims the benefit of U.S. Provisional Patent Application No. 62/629,644, filed Feb. 12, 2018, and U.S. Provisional Patent Application No. 62/628,842, filed Feb. 9, 2018, and U.S. Provisional Patent Application No. 62/492,065, filed Apr. 28, 2017, each of which are incorporated herein by reference in their entirety.

TECHNICAL FIELD

The present application is generally directed to managing the resources of the computers connected by a computer network.

BACKGROUND

Despite the long-standing, massive effort to develop effective methods for increasing healthy behavior in human subjects, the number of people worldwide who suffer from adverse cardiometabolic conditions such as obesity, cardiovascular disease, and metabolic disorders (e.g., type-II diabetes) is rapidly growing. These conditions result in numerous medical complications, a lowered quality of life, shortened lifespan, lost work productivity, a strain on medical systems, and a burden on medical insurance providers, all of which translates into increased costs for both individuals and society.

Indeed, type 2 diabetes prevalence is at pandemic levels and continues to rise in the U.S. and globally. NCD Risk Factor Collaboration, *The Lancet* 387:1513-1530 (2016); Shi & Hu, *The Lancet* 383:1947-1948 (2014). Medication costs are rising in parallel and threaten to bankrupt national health systems. National Diabetes Statistics Report 2017: Centers for Disease Control and Prevention, U.S. Department of Health and Human Services (internet); Economic Costs of Diabetes in the U.S. in 2012, *Diabetes Care* 36(4):1033-1046 (2013). Despite increased use of medications and the advent of new pharmacological interventions, glycemic control among those with diabetes has not been improving since 2010. Barnard et al., Change in Testing, Awareness of Hemoglobin A1c Result, and Glycemic Control in US Adults, 2007-2014 *JAMA* 318(8):1825-1827 (2017).

As but one example, metformin is an antihyperglycemic agent that can improve glucose tolerance in patients with type II diabetes by lowering both basal and post-prandial plasma glucose. In patients with known or suspected impaired renal function such as those with advanced age, however, metformin administration requires close dose monitoring and titration to prevent lactic acidosis, a potentially fatal metabolic complication. Patients with concomitant cardiovascular or liver disease, sepsis, and hypoxia also have an increased risk of lactic acidosis. Thus, metformin remains an unavailable and/or risky treatment for certain patient groups due to its side effects.

Similarly, the pharmaceutical and surgical interventions currently available for treatment of obesity are also associated with significant risks and costs. Until recently, obesity treatments included two FDA-approved drugs. Orlistat (Xenical®) reduces intestinal fat absorption by inhibiting pancreatic lipase, while sibutramine (Meridia®) decreases appetite by inhibiting deactivation of the neurotransmitters norepinephrine, serotonin, and dopamine, but sibutramine has now been taken off the market in the U.S. and Europe. Undesirable side-effects, including effects on blood pressure, have been reported with both these drugs. (See, e.g., "Prescription Medications for the Treatment of Obesity," NIH Publication No. 07-4191, December 2007). Moreover, surgical treatments, including gastric bypass surgery and gastric banding, are available, but only in extreme cases. These procedures can be dangerous, and furthermore may not be appropriate options for patients with more modest weight loss goals.

As yet another example, cardiac disease intervention can include statins, diuretics, ACE inhibitors, calcium channel blockers, beta blockers, alpha blockers, angioplasty, and cardiac bypass surgery. Each of these medical or surgical interventions for addressing cardiometabolic conditions are associated with significant risks and costs.

More recently, efforts have been made to intervene with individuals via a digital interface, both to collect personal biometric data from participants and to encourage their participation in established diabetes protocols, e.g., via group therapy. See, e.g., US 2013/0117040 and US 2007/0072156. Unfortunately, however, the predictive analytics employed in these platforms are generally inadequate, placing primary reliance on body metric data collection and comparative analysis against generalized body metric objectives. Moreover, subsequent interventions lack personalization and are largely historical in focus, i.e. a determination of how far the participant has progressed towards a given objective. Not surprisingly, then, compliance rates for existing digital programs directed toward behavioral changes that are targeted toward improving one or more lifestyle-related health conditions are extremely low and generally not durable over time. Thus, there remains a need for development of methods and systems for managing lifestyle interventions in a manner that provides improved compliance, improved outcomes, and/or long-term durability of improved health.

SUMMARY

The present invention successfully resolves this long-standing need in the art by way of a novel, skill-focused digital therapeutic intervention directed to modifying a patient's lifestyle, e.g. their dietary and activity patterns, and improving their culinary and fitness literacy, comprising a digital interface collecting and delivering data and information to the patient and coordinating human support. As demonstrated herein for the first time, the subject intervention can provide a measurable improvement in one or more therapeutic milestones in cardiometabolic disorders such as diabetes or hypertension, increase adherence to a lifestyle regimen, and can in some instances lead to an actual reduction in pharmaceutical reliance.

In one aspect, the present invention provides a method for improving a lifestyle-related health condition of a subject, said method comprising: a) providing to said subject a digital interface for: i) receiving a lifestyle intervention regimen to achieve a lifestyle-related health condition milestone; ii) entering subject-specific data for one or more validated compliance parameters associated with said lifestyle-related health condition milestone; and iii) optionally collecting body metric measurements; b) receiving from said subject and via the digital interface, said subject-specific data for one or more validated compliance parameters associated with said lifestyle-related health condition milestone; c) comparing entry activity comprised of a rate and/or number of said subject-specific data received from said subject via the digital interface with a database of entry activity by prior subjects; and d) providing said subject with milestone achievement input, wherein said milestone achievement input is derived at least in part, or entirely, from the entry activity (e.g., rate and/or number of subject-specific data entry) received from said subject via said digital interface, and predicts the subject's likelihood of success in achieving the lifestyle-related health condition milestone at a future date.

In another aspect, the present invention provides a method for treating a subject having or at risk of having a cardiometabolic disorder, said method comprising: a) providing to said subject a digital interface for: i) receiving a lifestyle intervention regimen to achieve a therapeutic milestone for said cardiometabolic disorder; ii) entering subject-specific data for one or more validated compliance parameters associated with said therapeutic milestone for said cardiometabolic disorder; and iii) optionally collecting body metric measurements; b) receiving from said subject and via the digital interface, said subject-specific data for one or more validated compliance parameters associated with said therapeutic milestone; c) comparing entry activity comprised of a rate and/or number of said subject-specific data received from said subject via the digital interface with a database of entry activity by prior subjects; and d) providing said subject with milestone achievement input, wherein said milestone achievement input is derived at least in part, or entirely, from the entry activity (e.g., rate and/or number of subject-specific data entry) received from said subject via said digital interface, and predicts the subject's likelihood of success in achieving the therapeutic milestone for said cardiometabolic disorder at a future date. In some embodiments, the methods of treatment result in a reduced dosage of one or more pharmaceutical interventions.

In another aspect, methods for reducing reliance on and/or dosage of a pharmaceutical intervention in a subject having a cardiometabolic disorder are provided, comprising a) providing to said subject a digital interface for: i) receiving a lifestyle intervention regimen to achieve a therapeutic milestone for said cardiometabolic disorder; ii) entering subject-specific data for one or more validated compliance parameters associated with said therapeutic milestone for said cardiometabolic disorder; and iii) optionally collecting body metric measurements; b) receiving from said subject and via the digital interface, said subject-specific data for one or more validated compliance parameters associated with said therapeutic milestone; c) comparing entry activity comprised of a rate and/or number of said subject-specific data received from said subject via the digital interface with a database of entry activity by prior subjects; d) providing said subject with milestone achievement input, wherein said milestone achievement input is derived at least in part, or entirely, from the entry activity (e.g., rate and/or number of subject-specific data entry) received from said subject via said digital interface, and predicts the subject's likelihood of success in achieving the therapeutic milestone for said cardiometabolic disorder at a future date.

In another aspect, the present invention provides a method for improving a lifestyle-related health condition in a subject by a) providing to said subject a digital interface for: i) receiving a lifestyle intervention regimen to achieve a lifestyle-related health condition milestone; ii) entering subject-specific data for one or more validated compliance parameters associated with said lifestyle-related health condition milestone; and iii) optionally collecting body metric measurements; b) monitoring entry of said subject-specific data for one or more validated compliance parameters associated with said lifestyle-related health condition milestone by said subject and via the digital interface; c) detecting an entry activity rate or amount that is below a threshold; and d) sending a notification that triggers a user local device to present a message to increase entry activity, wherein in comparison to an absence of the monitoring, detecting, and sending, the method: i) increases the subject's likelihood of adherence to the lifestyle intervention program; ii) increases the subject's likelihood of success in achieving the lifestyle-related health condition milestone at a future date; iii) reduces reliance on one or more pharmaceutical interventions in the subject; and/or iv) provides a measurable improvement in one or more therapeutic milestones.

In another aspect, the present invention provides a method for improving a lifestyle-related health condition in a subject by a) providing to said subject a digital interface for: i) receiving a lifestyle intervention regimen to achieve a lifestyle-related health condition milestone; ii) entering subject-specific data for one or more validated compliance parameters associated with said lifestyle-related health condition milestone; and iii) optionally collecting body metric measurements; b) monitoring entry of said subject-specific data for one or more validated compliance parameters associated with said lifestyle-related health condition milestone by said subject and via the digital interface; c) detecting a failure to achieve or report achievement of one or more validated compliance parameters; and d) sending a notification that triggers a user local device to present a message to achieve or report achievement of one or more validated compliance parameters, wherein in comparison to an absence of the monitoring, detecting, and sending, the method: i) increases the subject's likelihood of adherence to the lifestyle intervention program; ii) increases the subject's likelihood of success in achieving the lifestyle-related health condition milestone at a future date; iii) reduces reliance pharmaceutical on one or more pharmaceutical interventions in the subject; and/or iv) provides a measurable improvement in one or more therapeutic milestones.

In an exemplary embodiment of the above methods, the cardiometabolic disorder is diabetes and the therapeutic milestone comprises one or more of maintenance of HbA1c, fasting glucose, fasting insulin, alanine transaminase, and/or fasting lipids at a level indicative of therapeutic benefit for a subject having or at risk of having diabetes. In some embodiments, the pharmaceutical intervention(s) comprise one or more interventions selected from the group consisting of: biguanides; sulfonylureas; meglitinide derivatives; alpha-glucosidase inhibitors; thiazolidinediones (TZDs); glucagonlike peptide-1 (GLP-1) agonists; dipeptidyl peptidase IV (DPP-4) inhibitors; selective sodium-glucose transporter-2 (SGLT-2) inhibitors, and insulin.

In another exemplary embodiment of the above methods, the cardiometabolic disorder is heart disease and the therapeutic milestone comprises one or more of weight loss, improved lipid profile, lower blood pressure, and lower resting pulse rate. In some embodiments, the pharmaceutical intervention(s) comprise one or more interventions selected from the group consisting of: a beta-blocking agent, an alpha-blocking agent, an angiotensin-converting enzyme inhibitor, a statin, a diuretic, and a calcium channel blocker.

In another exemplary embodiment, the cardiometabolic disorder is hypertension and the therapeutic milestone comprises maintenance of a diastolic and/or systolic blood pressure at a level indicative of therapeutic benefit for a subject having or at risk of having hypertension. In some embodiments, the pharmaceutical intervention(s) comprise one or more interventions selected from the group consisting of: a beta-blocking agent, an alpha-blocking agent, an angiotensin-converting enzyme inhibitor, an angiotensin II receptor blocker, a calcium channel blocker, a diuretic, and a renin inhibitor.

In another exemplary embodiment, the cardiometabolic disorder is hyperlipidemia and the therapeutic milestone is improved lipid profile. In some embodiments, the pharmaceutical intervention(s) comprise one or more interventions selected from the group consisting of: a statin, exetimibe, and PCSK9 inhibitors.

In another exemplary embodiment, the cardiometabolic disorder is coronary artery disease and the therapeutic milestone comprises one or more of weight loss, improved lipid profile, lower blood pressure, increased stamina, reduced angina, reduced fluid retention, increased coronary arterial blood flow; and reduced arterial plaque. In some embodiments, the pharmaceutical intervention(s) comprise one or more interventions selected from the group consisting of: a) a cholesterol-modifying medication selected from the group consisting of a statin, exetimibe, and PCSK9 inhibitors; b) an anti-coagulant, preferably selected from the group consisting of an anti-platelet agent (e.g. aspirin or Plavix), warfarin, low-molecular weight heparin, a direct thrombin inhibitor, and a factor Xa inhibitor; c) a beta-blocking agent, d) a vasodilator; e) a diuretic; and f) an angiotensin-converting enzyme inhibitor and an angiotensin II receptor blocking agent.

In some embodiments of the foregoing aspects, the lifestyle intervention regimen is selected from the group consisting of a dietary regimen and an activity regimen, or a combination thereof. In some cases, the lifestyle intervention regimen comprises a dietary regimen, and said dietary regimen comprises a plant-based diet. In some cases, the plant-based diet comprises, consists essentially of, or consists of vegetables, fruit, legumes, nuts and seeds, and whole grains. In some cases, the plant-based diet comprises at least 50% of calories, or a majority of calories, from vegetables, fruit, legumes, nuts and seeds, and whole grains. As used herein, a plant-based diet consisting essentially of vegetables, fruit, legumes, nuts and seeds, and whole grains is comprised of at least 80% of calories from foods that are categorized as a vegetable, fruit, legume, nut, seed, or whole grains. Similarly, a plant-based diet consisting of vegetables, fruit, legumes, nuts and seeds, and whole grains does not comprise calories from animal-derived protein or fat, highly refined flour, or added dietary sweeteners (e.g., sugar, cane syrup, etc.). In some cases, the dietary regimen further comprises a culinary literacy program comprising at least one of recipes, ingredients and local ingredient acquisition locations. In some cases, the validated compliance parameters comprise one or more compliance parameters selected from the group consisting of: a) generate meal plan; b) follow meal plan; c) procure ingredients from a shopping list; d) engage with digital interface; e) log daily or weekly targets (e.g. plant-based meals consumed, exercise performed); f) log hydration; and/or g) communicate with coach.

In some embodiments of the foregoing aspects, the validated compliance parameters comprise at least 2, 3, 4, 5, or 6, or all of the compliance parameters selected from the group consisting of: a) generate meal plan; b) follow meal plan; c) procure ingredients from a shopping list; d) engage with digital interface; e) log daily and/or weekly targets (e.g.

plant-based meals consumed, exercise performed); f) log hydration; and g) communicate with coach.

In some embodiments of the foregoing aspects, the lifestyle intervention comprises an activity regimen, and said activity regimen comprises an exercise routine (e.g. type, frequency and intensity of exercise), a daily caloric burn target, or a combination thereof. In some cases, the validated compliance parameters comprise compliance parameters selected from the group consisting of: a) type of activity (e.g., resistance training, interval training, flexibility training, cardiovascular training); b) intensity of activity; c) duration of activity; d) frequency of activity; e) engage with digital interface; f) log daily and/or weekly targets (e.g. plant-based meals consumed, exercise performed); g) log hydration; and h) communicate with coach. In some cases, the lifestyle intervention further comprises the dietary regimen.

In some embodiments of the foregoing aspects, the method comprises collecting body weight metric measurements of said subject via the digital interface and said milestone achievement input is further derived from the body metric measurements of said subject collected via the digital interface.

In some embodiments, the providing to said subject the digital interface comprises transmitting the digital interface from a digital interface server to a user local display. In some embodiments, the user local display is a component of a user local device, wherein said user local device comprises the user-local display, a user local processor, and a user local datalink. In some embodiments, the receiving from said subject said subject-specific data comprises receiving one or more transmissions comprising said subject-specific data: a) from said user local datalink; and b) to a comparison engine.

In some embodiments, the providing said subject with milestone achievement input comprises transmitting computer readable instructions to said user-local device through said user-local datalink, wherein said computer readable instructions are configured to display a message comprising said input on said user-local display. In some embodiments, the message comprises a pre-configured communication indicating likelihood of success. In some embodiments, the message comprises a pre-configured communication encouraging increased engagement with the digital interface (e.g., increased entry of subject-specific data). In some embodiments, the message comprises a pre-configured communication encouraging increased adherence to the lifestyle intervention regimen.

In some embodiments, the milestone achievement input comprises a communication (e.g., displayed by the digital interface) that indicates likelihood of achieving a milestone. The milestone achievement input can be in the form of a graphical icon or a numerical score, or a combination thereof.

In some cases, the milestone achievement input communicates a number, degree, or proportion by which the subject, in one or more compliance parameters, has lagged prior individuals in the database that successfully achieved the milestone, or has lagged a population of prior individuals in the database, which population of prior individuals is overrepresented by milestone achievers as compared to the average individual.

In some cases, the milestone achievement input communicates a number, degree, or proportion by which the subject, in one or more compliance parameters, has lagged an average (mean or median) of a population of prior individuals in the database that successfully achieved the milestone, or has lagged a population of prior individuals in the database, which population of prior individuals is overrepresented by milestone achievers as compared to the average individual. In some cases, the population is a selected sub-population of prior individuals that is matched to a subject's age, age range, gender, cardiometabolic disorder, body mass index, or body mass index range.

In some embodiments, the milestone achievement input comprises additional or alternative lifestyle interventions or regimens for increasing the likelihood or degree of milestone achievement, and/or increasing adherence to the lifestyle regimen. In some embodiments, the milestone achievement input comprises access to digital tools, e.g. for meal and/or exercise planning. In some embodiments, the milestone achievement input further comprises a request or requirement for confirmation or proof of completion of such additional or alternative lifestyle interventions or regimens, e.g. by photographic means.

In some embodiments, the milestone achievement input comprises a care escalation protocol providing for and/or scheduling a follow-up meeting with one or more human service providers (e.g., health coach, dietician, nutritionist, chef-educator, nurse practitioner, physical therapist, kinesiologist, physician, behavioral psychologist, psychiatrist, and the like). Additionally or alternatively, such care-escalation protocols can include a suggestion to complete one or more individual (one-on-one) or small-group coaching sessions with a medical service provider (e.g., nurse practitioner, physical therapist, kinesiologist, physician, behavioral psychologist, psychiatrist, and the like).

In some cases, where a subject enters a low number, count, rate, intensity, or entry activity of meal plan use; meal fallback; shopping list use; or number of meal plan meals consumed, the methods described herein can include a suggestion to complete one or more individual (one-on-one) or small-group coaching sessions with a health coach, dietician, nutritionist, chef-educator and/or combinations thereof. In some cases, where a subject enters a low number, count, rate, intensity, or entry activity of physical activities prescribed by the life-style regime, the methods described herein can include a suggestion to complete one or more individual (one-on-one) or small-group coaching sessions with a health coach, physical therapist, kinesiologist, and/or combinations thereof. In related embodiments, the method further comprises: step e) initiating direct personal feedback to said subject or increasing the level of direct personal feedback provided to said subject when said subject is predicted to be likely to miss their milestone.

In some embodiments, and particularly where there has been no or only limited engagement by the subject with the digital interface, a notification that triggers a user local device to present a message for interfacing with and/or encouraging dialogue with an automated chat module (chatbot) is provided to the user local device. In some embodiments, the automated chat module is configured to increase adherence to the lifestyle intervention regimen, e.g., via providing an interactive dialogue interface for encouraging the subject to engage with the digital interface and/or enter subject-specific data. In some embodiments, the automated chat module is configured to increase rate or number of subject-specific data entered by the subject via the digital interface, e.g., via providing an interactive dialogue interface. Chatbot technologies and their use are further described in co-pending PCT application entitled "SYSTEMS, METHODS, AND APPARATUSES FOR MANAGING DATA FOR ARTIFICIAL INTELLIGENCE SOFTWARE AND MOBILE APPLICATIONS IN DIGITAL HEALTH THERAPEUTICS", PCT Application No. PCT/US18/29654, filed Apr. 26, 2018.

In some embodiments, the lifestyle-related health condition milestone or therapeutic milestone for said cardiometabolic disorder comprises weight loss.

In some embodiments, the cardiometabolic disorder is diabetes, and said therapeutic milestone comprises maintenance of an HbA1c at a level indicative of therapeutic benefit for a subject having or at risk of having type-II diabetes.

In some embodiments, the cardiometabolic disorder is heart disease, and said therapeutic milestone comprises is selected from the group consisting of: a) weight loss; b) improved lipid profile; c) lower blood pressure; and d) lower resting pulse rate.

In another aspect, the present invention provides a system for performing a method according to any one of the foregoing aspects, embodiments, cases, or examples. In another aspect, the present invention provides a computer readable medium for performing a method according to any one of the foregoing aspects, embodiments, cases, or examples.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 3 is a flow chart of an embodiment of a method for treating a subject having or at risk of having a cardiometabolic disorder.

FIG. 12 illustrates data from performing an embodiment of a method disclosed herein. In this embodiment, participant subjects entered via the digital interface an indication of water intake. The data indicate that more frequent logging of water-intake via the digital interface is positively correlated with weight loss.

FIG. 13 illustrates data from performing an embodiment of a method disclosed herein. In this embodiment, participant subjects entered via the digital interface an indication that a provided shopping list was used. The data indicate that more frequent logging of shopping list use via the digital interface is positively correlated with weight loss.

Participant subjects who logged the most meal plan utilization lost approximately twice as much weight as those who logged the least.

Figure 20:
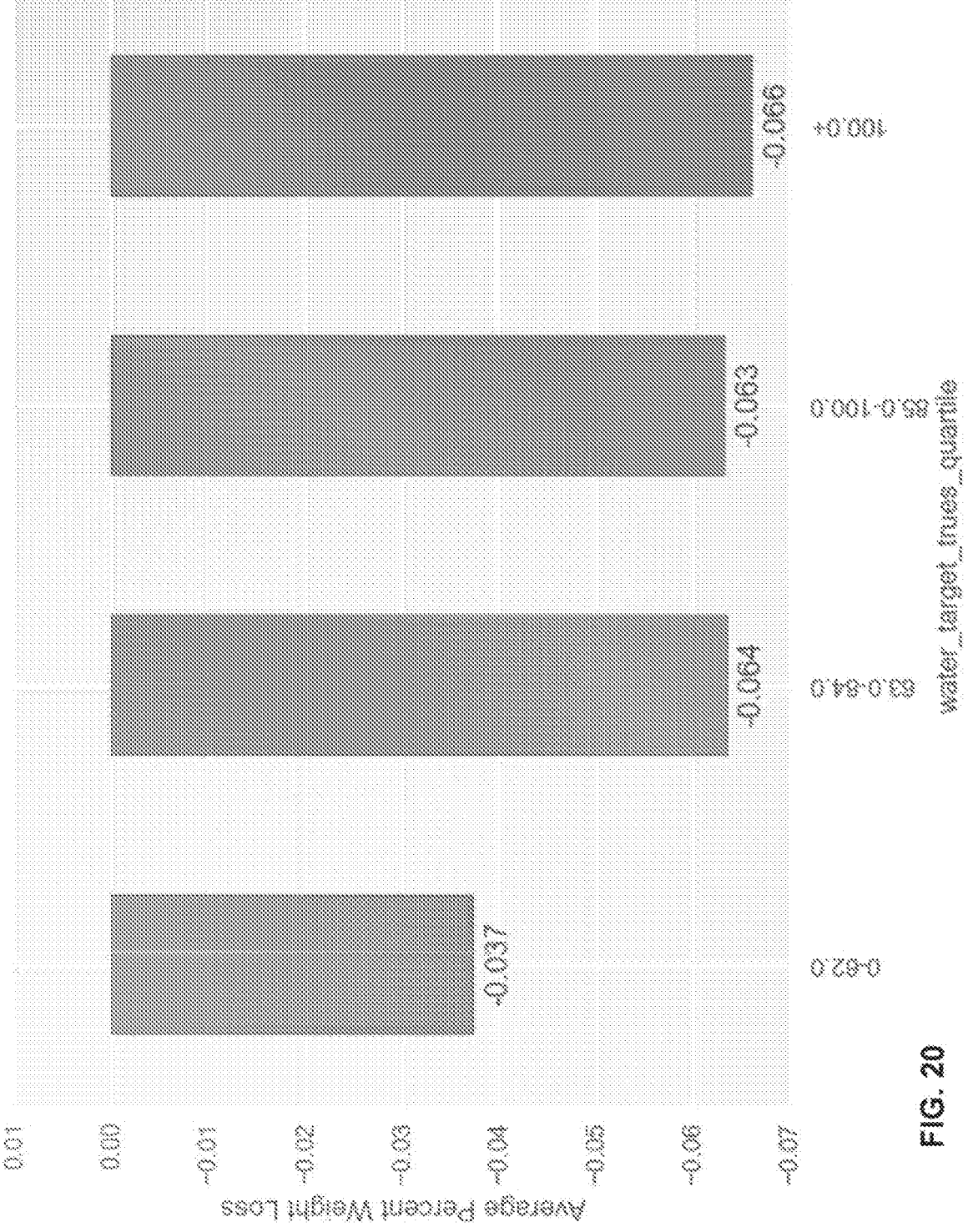

FIG. 20 illustrates data from performing an embodiment of a method disclosed herein. Water-intake count data entered via the digital interface were divided into four equal sized quartiles. More frequent logging of water-intake via the digital interface was positively correlated with weight loss. Participant subjects who logged the most water-intake lost approximately twice as much weight as those who logged the least.

Figure 21:
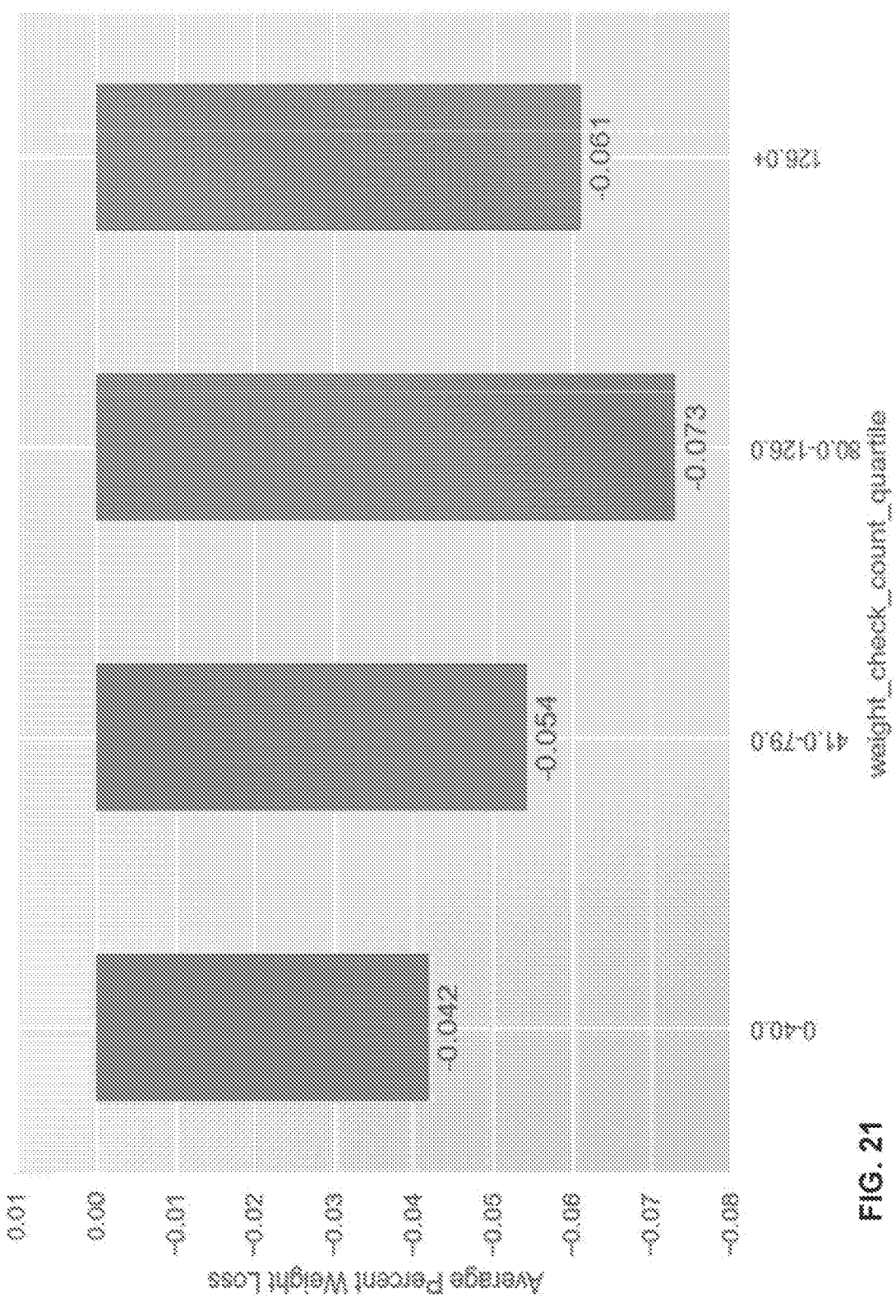

FIG. 21 illustrates data from performing an embodiment of a method disclosed herein. Body weight check activity data entered via the digital interface were divided into four equal sized quartiles. More frequent logging via the digital interface of performance of a body weight check was positively correlated with weight loss.

Figure 22:
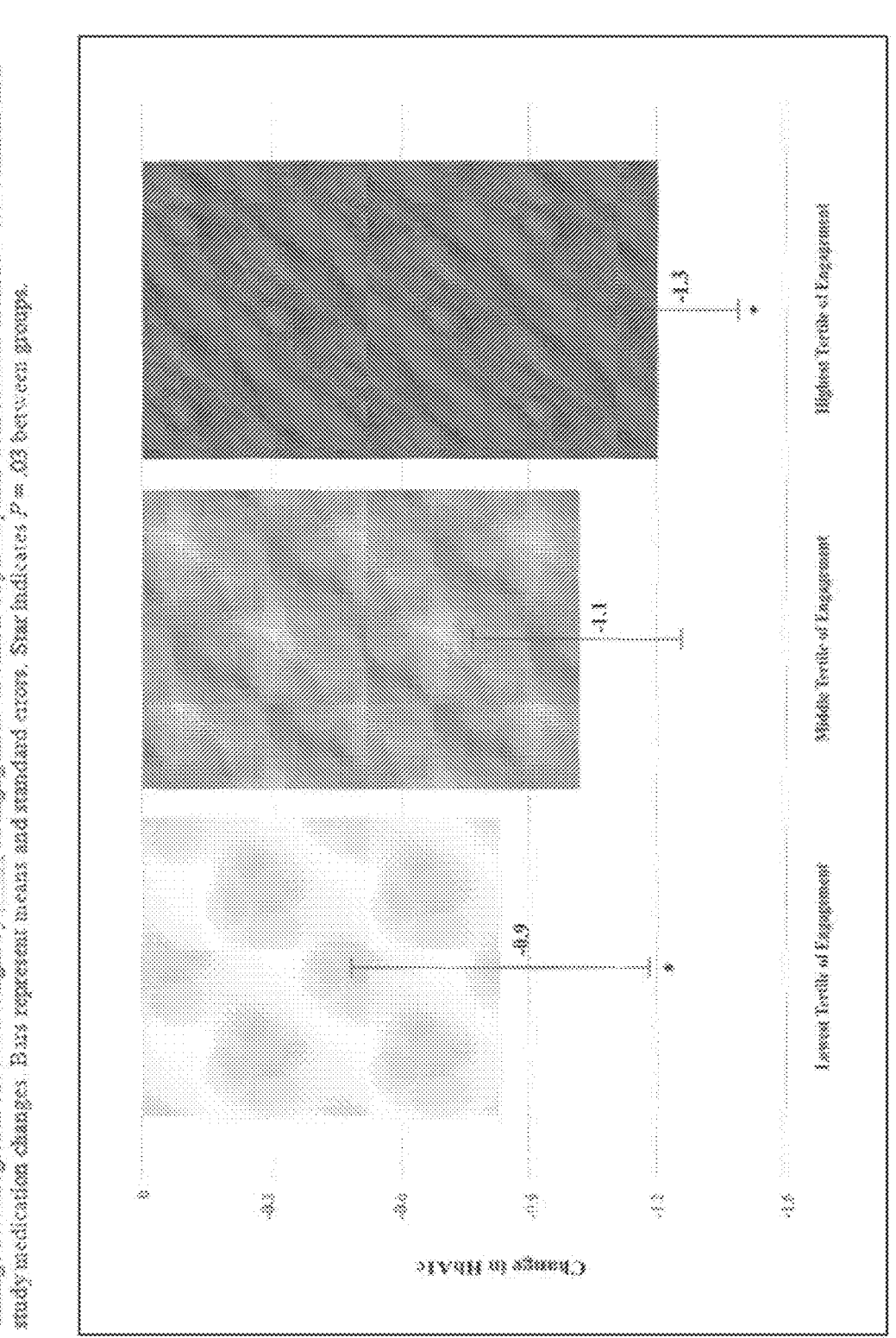

FIG. 22 compares the change in hemoglobin A1c and weight by tertile of engagement in subset of participants with baseline HbA1c>7.0% and no mid-study medication changes. Bars represent means and standard errors. Star indicates P=0.03 between groups.

Figure 23:
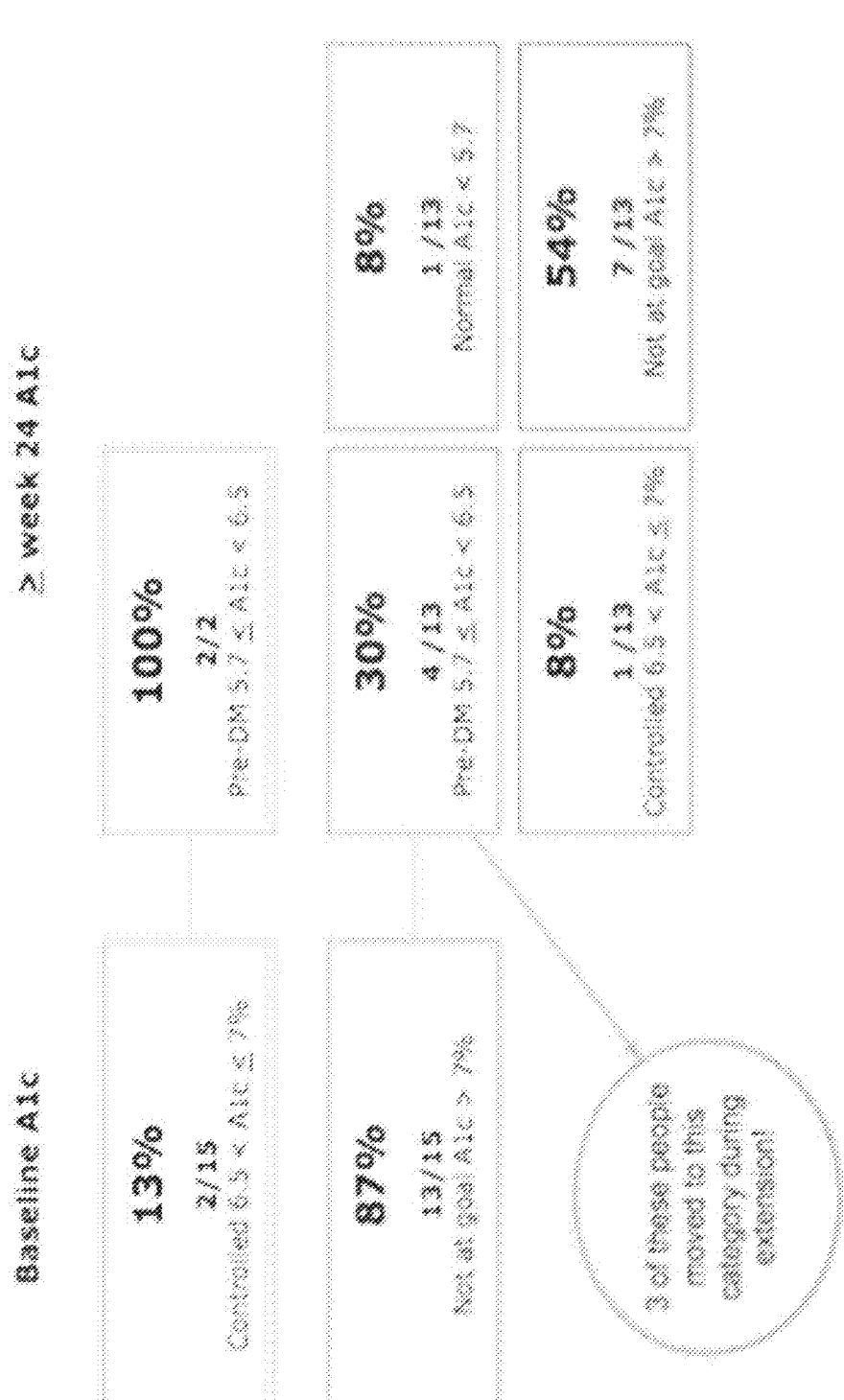

FIG. 23 illustrates therapeutic milestone achievement in subjects participating in extended (>12 weeks) diabetes treatment study.

Figure 24:
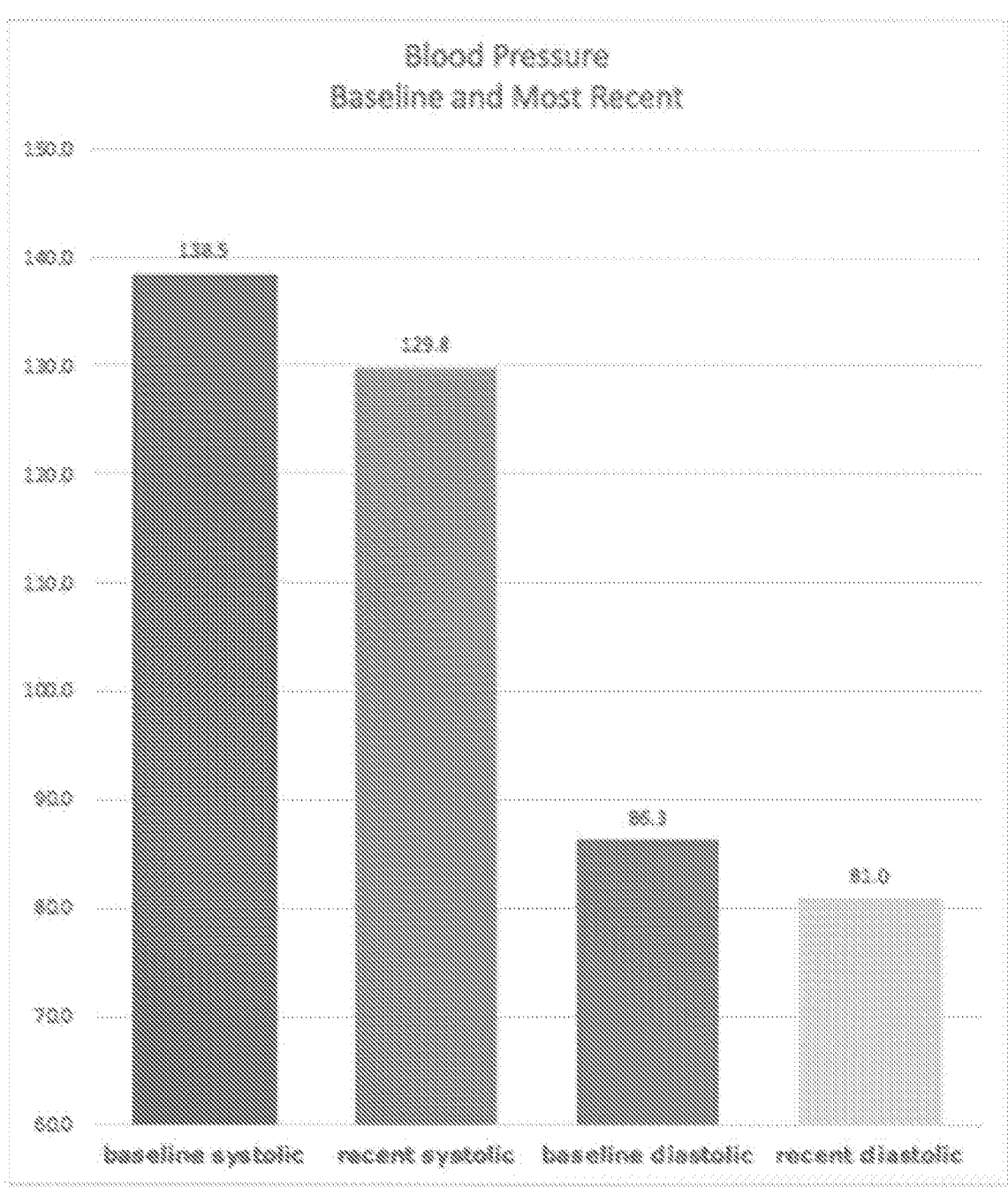

FIG. 24 illustrates therapeutic milestone achievement in subjects participating in hypertension treatment study.

DETAILED DESCRIPTION

The present invention relates to methods and systems for improving a lifestyle-related health condition of a subject. An exemplary lifestyle-related health condition is body weight. However, the methods and systems described herein can be applied to improve a variety of different lifestyle-related health conditions as well as particular cardiometabolic disorders for which the patient may already be undergoing clinical treatment. Cardiometabolic disorders that may be effectively targeted and treated by way of the subject invention include, e.g. metabolic disorders such as hyperglycemia, diabetes and the like as well as cardiovascular diseases such as hypertension, hyperlipidemia, angina, and the like.

In some embodiments, a method 100 is provided, including step 110 providing to a subject a digital interface. Typically, the digital interface is displayed on a user-local device. As used herein "user-local" device refers to a device that is owned or in physical possession of the subject. In some cases, the digital interface is provided by transmitting instructions to display the digital interface from a remote server to the user-local device. In other cases, the instructions to display the digital interface can be stored on the user-local device. In yet other cases, a portion of the instructions to display the digital interface can be stored on the user-local device, and a portion of the instructions transmitted to the user-local device from a remote server. The instructions can be stored and/or transmitted in the form of transitory or non-transitory computer readable media.

The digital interface of this embodiment is configured to receive subject-specific data for one or more validated compliance parameters that is entered by the subject via the digital interface. The validated compliance parameters can be validated as associated with a lifestyle-related health condition milestone. The lifestyle-related health condition milestone can be an improvement in a lifestyle-related health condition, or a target level of improvement in a lifestyle-related health condition. In some cases, the lifestyle-related health condition milestone is selected by the subject via the digital interface. In other cases, the lifestyle-related health condition milestone is pre-selected by the digital interface provider.

The method can further include a step 115b, in which a subject enters subject-specific data for one or more validated compliance parameters. Such data can include one or more of the following: whether a meal plan was followed; whether a lifestyle regimen activity was completed; whether a coaching call was completed; whether one or more, or all, ingredients on a shopping list were procured; whether the subject consumed a specified amount of water or whether the subject consumed water; a number of plant-based meals consumed, a number of exercise activities completed, the length of exercise activities completed (e.g. minutes of daily or weekly exercise), a number of coaching calls completed, length of one or more coaching calls, a number or fraction of ingredients procured from a shopping list, a number of hydration events, or a total volume of hydration. In some cases, where a meal plan was not followed, the data can include whether a meal fallback was consumed. In some cases, exercise data can include type of activity completed, e.g., resistance training, interval training, flexibility training, or cardiovascular training. In some cases, exercise data can include sub-type of activity completed, e.g., running, walking, swimming, weight lifting, yoga, etc. In some cases, data can include number or frequency of body weight measurements performed.

In preferred embodiments, the dietary regimens employed in the subject methods comprise, consist essentially of, or consist of a plant-based diet, i.e., they include one or more ingredients taken from the general classes of vegetables, fruits, legumes, whole grains, and/or nuts and seeds, the beneficial clinical impact of which has been well established. See, e.g., Jenkins et al., A dietary portfolio approach to cholesterol reduction: combined effects of plant sterols, vegetable proteins, and viscous fibers in hypercholesterolemia *Metabolism* 51:1596-1604 (2002); Barnard et al., A low-fat vegan diet and a conventional diabetes diet in the treatment of type 2 diabetes: a randomized, controlled, 74-wk clinical trial *Am J Clin Nutr* 89:15885-15968 (2009). In some embodiments, the plant-based diet comprises at least 50% of calories, or a majority of calories, from the foregoing general classes of vegetables, fruits, legumes, whole grains, and/or nuts and seeds. In some embodiments, the plant-based diet consists or consists essentially of vegetables, fruit, legumes, nuts and seeds, and whole grains. In some embodiments, where a meal plan focuses primarily on one class of ingredient, e.g., a vegetable or a legume, suitable meal fallbacks will be selected from among the remaining classes of ingredients, e.g., fruits, whole grains and/or nuts and seeds. As demonstrated herein the predictive value of non-compliance with a given meal plan is further enhanced by determining adherence to the preferred dietary principles, i.e. following a plant-based diet, by way of fall back inquiries.

In some cases, the data can be received, stored, and/or transmitted as a Boolean variable (e.g., true or false). For example, meal plan use data can be stored as a true indicating a meal plan was used (i.e., the meal specified by the meal plan was consumed) or a false indicating that a meal plan was not used (i.e., the meal specified by the meal plan was not consumed). In some cases, the data can be received, stored, and/or transmitted as a numerical variable (e.g., number of exercise activities completed, total amount of time engaged in one or more exercise activities, number of meals consumed, or number of coaching calls completed).

In an optional step 115c, that may be present or absent in this embodiment, the subject enters one or more body metric measurements. The one or more body metric measurements can be or include body weight, lipid profile, cholesterol level, triglyceride levels, low-density lipoprotein level, high-density lipoprotein level, very low-density lipoprotein level, blood pressure, fasting blood glucose level, pre-prandial glucose level; post-prandial glucose level, blood insulin level, fasting insulin level, alanine transaminase level, blood GIP level, insulin resistance, or glycated hemoglobin (HbA1c) level.

The method can further include a step 120, in which the subject-specific data entered into the digital interface by the subject is received. In some embodiments, the subject-specific data, or a portion thereof, is transmitted from the user-local device and received by a remote server. In some cases, the remote server includes a comparison engine. In some cases, the remote server transmits the subject-specific data or a component thereof to a comparison engine. The method can further include 135, comparing a rate or number of the subject specific data with a database of entry activity by prior subjects.

The comparison engine can output a prediction of likelihood of milestone achievement based on the entry activity by prior subjects. The likelihood can be determined as a function of engagement with the digital interface (i.e., number of times a subject has entered one or more, or all, subject-specific data), engagement with the lifestyle regimen (i.e., rate of compliance with lifestyle regimen activities, meal plans and the like). The likelihood can be determined as a function of one or more compliance parameters (e.g., true, false, number, or rate). For example, the likelihood can be determined as a function of whether a meal plan was followed or logged; or if not, whether a meal fallback was consumed or logged; whether a lifestyle regimen activity was completed or logged; whether a coaching call was completed or logged; whether ingredients on a lifestyle regimen shopping list were procured or logged; whether the subject consumed a specified amount of water or whether water intake was logged; a number of plant-based meals consumed, a number of exercise activities completed, the length of exercise activities completed (e.g. minutes of daily or weekly exercise), a number of coaching calls completed, length of one or more coaching calls, a number or fraction of ingredients procured from a shopping list, a number of hydration events, a total volume of hydration logged, or a number or rate of body weight measurements performed. In some cases, the likelihood can be determined as a function of type, duration, frequency and/or intensity of exercise completed and/or logged.

In some cases, the likelihood is determined by a multi-factorial weighted analysis of two or more, three or more, four or more, five or more, six or more, seven or more, eight or more, or all types, amounts, or rates of entry activity sub-types (e.g., engagement with interface, engagement with lifestyle regimen, compliance parameters, and/or type, frequency, duration and/or intensity of exercise completed). The weights and activity sub-types can be identified manually, by trial and error, or computationally via, e.g., logistic regression or machine learning, methods to identify patterns associated with a high or low likelihood of therapeutic milestone achievement.

For example, if a subject enters a low number of subject-specific datapoints (e.g., either relative to other members of the subject cohort, or relative to prior subjects in the database, or a portion thereof) into the digital interface, the comparison engine can indicate that the subject is unlikely to achieve a lifestyle-related health condition milestone. As another example, if a subject enters a high number of subject-specific datapoints into the digital interface, the comparison engine can indicate that the subject is likely to achieve a lifestyle-related health condition milestone.

As yet another example, if a subject enters into the digital interface a high number of meal plan meals consumed, the comparison engine can indicate that the subject is likely to achieve a lifestyle-related health condition milestone. As yet another example, if a subject enters into the digital interface a low number of meal plan meals consumed, the comparison engine can indicate that the subject is unlikely to achieve a lifestyle-related health condition milestone. As yet another example, if a subject enters into the digital interface a high number of meal fallbacks consumed, the comparison engine can indicate that the subject is likely to achieve a lifestyle-related condition health milestone. As yet another example, if a subject enters into the digital interface a low number of meal fallbacks consumed, the comparison engine can indicate that the subject is unlikely to achieve a lifestyle-related health condition milestone.

As yet another example, if a subject enters into the digital interface a high number of completed coaching calls, the comparison engine can indicate that the subject is likely to achieve a lifestyle-related health condition milestone. As yet another example, if a subject enters into the digital interface a low number of completed coaching calls, the comparison engine can indicate that the subject is unlikely to achieve a lifestyle-related health condition milestone. As yet another example, if a subject enters into the digital interface a high number or length of completed exercise activities, the comparison engine can indicate that the subject is likely to achieve a lifestyle-related health condition milestone. As yet another example, if a subject enters into the digital interface a low number or length of completed exercise activities, the comparison engine can indicate that the subject is unlikely to achieve a lifestyle-related health condition milestone.

As yet another example, if a subject enters into the digital interface a high number of meal water-intake events, the comparison engine can indicate that the subject is likely to achieve a lifestyle-related health condition milestone. As yet another example, if a subject enters into the digital interface a low number of water-intake events, the comparison engine can indicate that the subject is unlikely to achieve a lifestyle-related health condition milestone. As yet another example, if a subject enters into the digital interface a high volume of water intake, the comparison engine can indicate that the subject is likely to achieve a lifestyle-related health condition milestone. As yet another example, if a subject enters into the digital interface a low volume of water-intake, the comparison engine can indicate that the subject is unlikely to achieve a lifestyle-related health condition milestone.

As yet another example, if a subject enters into the digital interface a high number of shopping list ingredients procured, the comparison engine can indicate that the subject is likely to achieve a lifestyle-related health condition milestone. As yet another example, if a subject enters into the digital interface a low number of number of shopping list ingredients procured, the comparison engine can indicate that the subject is unlikely to achieve a lifestyle-related health condition milestone. As yet another example, if a subject enters into the digital interface a high count of body weight measurement activities, the comparison engine can indicate that the subject is likely to achieve a lifestyle-related health condition milestone. As yet another example, if a subject enters into the digital interface a low count of body weight measurement activities, the comparison engine can indicate that the subject is unlikely to achieve a lifestyle-related health condition milestone.

In preferred embodiments, the prediction is a function of 2, 3, 4, 5, 6, 7, 8, 9, 10, or more of a number, count, rate, intensity, or entry activity of meal plan use; meal fallback; activity; coaching call; shopping list use; water-intake; a number of meal plan meals consumed, or a body weight measurement.

The method can further include 140, providing the subject with milestone achievement input. The milestone achievement input can be a communication (e.g., displayed by the digital interface) that indicates likelihood of achieving the lifestyle-related health condition milestone. The milestone achievement input can be in the form of a graphical icon or a numerical score, a pre-configured message, or a combination thereof. The milestone achievement input can suggest additional or alternative lifestyle interventions or regimens for increasing the likelihood or degree of milestone achievement. In some case, the milestone achievement input communicates a number, degree, or proportion by which the subject, in one or more compliance parameters, has lagged prior individuals in the database that successfully achieved the milestone, or has lagged a population of prior individuals in the database, which population of prior individuals is overrepresented by milestone achievers as compared to the average individual.

For example in some embodiments, coaching call completion shows a strong positive correlation with weight loss. In this case, a subject who has entered a low number of completed coaching calls via a digital interface can be predicted as unlikely to achieve the weight loss milestone. The milestone achievement input can suggest completing more coaching calls, or indicate the difference between coaching calls completed by the subject and coaching calls completed by the highest weight loss quartile of the prior individuals in the database, or provide for and/or schedule a follow-up meeting with one or more human service providers (e.g., health coach, dietician, nutritionist, chef-educator, nurse practitioner, physical therapist, kinesiologist, physician, behavioral psychologist, psychiatrist, and the like). Such care-escalation protocols can include a suggestion to complete one or more individual (one-on-one) or small-group coaching sessions with a medical provider (e.g., nurse practitioner, physical therapist, kinesiologist, physician, behavioral psychologist, psychiatrist, or a combination thereof). In some cases, where a subject enters a low number, count, rate, intensity, or entry activity of meal plan use; meal fallback; shopping list use; or number of meal plan meals consumed, the methods described herein can include a suggestion to complete one or more individual (one-on-one) or small-group coaching sessions with a health coach, nutritionist, dietician, and/or chef-educator. In this way, more time-consuming and/or expensive human resources and/or personal medical care can be more efficiently implemented in escalating fashion when needed in order to assist the subject with their milestone achievement, and is not utilized with individuals who are likely to reach their milestone achievement in any event.

The milestone achievement input can be a communication (e.g., displayed by the digital interface) that is configured to increase engagement with the digital interface. For example, the communication can request entry of subject-specific data for one or more compliance parameters. In some embodiments, the method can include monitoring entry activity for one or more compliance parameters, detecting an absence of entry activity or an entry activity that is below a threshold and providing a milestone achievement input that requests or encourages entry activity. In some embodiments, the method can include monitoring entry activity for one or more compliance parameters, detecting an absence of entry activity indicating completion of one or more compliance parameters or an entry activity indicating completion of one or more compliance parameters that is below a threshold and providing a milestone achievement input that requests or encourages entry activity, and/or requests or encourages completion of one more compliance parameters.

In an exemplary embodiment, a subject that fails to report completion of a meal plan or completion of a threshold number of meal plans specified in the lifestyle intervention regimen, can be provided a milestone achievement input encouraging the subject to complete one or more meal-plans and/or enter meal-plans into the digital interface. In another exemplary embodiment, a subject that fails to report either completion or non-completion of a meal plan or a threshold number of meal plans specified in the lifestyle intervention regimen, can be provided a milestone achievement input instructing the subject to enter meal-plans into the digital interface.

Similarly, a subject that fails to report, via the digital interface, completion of a length of activity or number of exercise activities or completion of a threshold number or length of exercise activity specified in the lifestyle intervention regimen, can be provided a milestone achievement input encouraging the subject to complete one or more exercise activities and/or enter exercise activity into the digital interface. In another exemplary embodiment, a subject that fails to report either completion or non-completion of exercise activity or a threshold number or length of exercise activities specified in the lifestyle intervention regimen, can be provided a milestone achievement input instructing the subject to enter exercise activity. In some cases, the milestone achievement input increases adherence to the lifestyle intervention regiment as compared to a method that does not provide such milestone achievement input.

In some embodiments the method or portions thereof is repeated one or more times. For example, after receiving the subject-specific data 120, the digital interface 110 can be provided to the subject for entry into the digital interface of subject specific data for one or more validated compliance parameters. Additionally or alternatively, the method can be repeated after the comparing step of 135. Additionally or alternatively, the method can be repeated after the providing step of 140. The repeating can be at a set frequency, such as hourly, daily, weekly, etc. (e.g., throughout the duration of the lifestyle intervention regimen). Alternatively, the repeating can be for a set number of times throughout the duration of the lifestyle intervention regimen. For example, the method can provide the digital interface for entry of subject-specific data about 2, 3, 4, 5, 6, 7, 8, 9, 10, 11, 12, 13, 14, 15, 16, or more times for the duration of the lifestyle intervention regimen. As another example, the repeating can be on a continual basis or initiated by the subject's access of the digital interface on the user-local device.

In some embodiments, a method 200 is provided, including a step 210 providing to a subject a digital interface as described herein. Typically, the digital interface is displayed on a user-local device. In some cases, the digital interface is provided by transmitting instructions to display the digital interface from a remote server to the user-local device. In other cases, the instructions to display the digital interface can be stored on the user-local device. In yet other cases, a portion of the instructions to display the digital interface can be stored on the user-local device, and a portion of the instructions transmitted to the user-local device from a remote server. The instructions can be stored and/or transmitted in the form of transitory or non-transitory computer readable media.

The digital interface of this embodiment is configured to receive subject-specific data for one or more validated compliance parameters that is entered by the subject via the digital interface. The validated compliance parameters can be validated as associated with a lifestyle-related health condition milestone. The lifestyle-related health condition milestone can be an improvement in a lifestyle-related health condition, or a target level of improvement in a lifestyle-related health condition. In some cases, the lifestyle-related health condition milestone is selected by the subject via the digital interface. In other cases, the lifestyle-related health condition milestone is pre-selected by the digital interface provider.

The method can further include a step 215a, in which a subject receives from the digital interface a lifestyle intervention regimen. Typically, the lifestyle intervention regimen is displayed as a series of lifestyle activities (e.g., diet or meal plans, exercise plans, hydration instructions, etc.) or provided as a file containing the series of lifestyle activities.

The method can further include a step 215b, in which a subject enters subject-specific data for one or more validated compliance parameters. Such data can include one or more of the following: whether a meal plan was followed; whether a lifestyle regimen activity was completed; whether a coaching call was completed; whether one or more, or all, ingredients on a shopping list were procured; whether the subject consumed a specified amount of water or whether the subject consumed water; a number of meal plan meals consumed, a number of exercise activities completed, a total amount time (e.g., minutes) engaged in one or more exercise activities, a number of coaching calls completed, length of one or more coaching calls, a number or fraction of ingredients procured from a shopping list, a number of hydration events, or a total volume of hydration. In some cases, where a meal plan was not followed, the data can include whether a meal fallback was consumed. In some cases, data can include type or amount of physical activity completed and/or logged. In some cases, data can include number or frequency of body weight measurements performed.

In some cases, the data can be received, stored, and/or transmitted as a Boolean variable (e.g., true or false). For example, meal plan use data can be stored as a true indicating a meal plan was used (i.e., the meal specified by the meal plan was consumed) or a false indicating that a meal plan was not used (i.e., the meal specified by the meal plan was not consumed). In some cases, the data can be received, stored, and/or transmitted as a numerical variable (e.g., total amount of time (e.g., minutes) engaged in one or more exercise activities, number of exercise activities completed, number of meals consumed, or number of coaching calls completed).

In an optional step 215c, that may be present or absent in this embodiment, the subject enters one or more body metric measurements. The one or more body metric measurements can be or include body weight, lipid profile, cholesterol level, triglyceride levels, low-density lipoprotein level, high-density lipoprotein level, very low-density lipoprotein level, blood pressure, fasting blood glucose level, pre-prandial blood glucose level, post-prandial blood glucose level, blood insulin level, fasting insulin level, blood alanine transaminase level, blood GIP level, insulin resistance, or glycated hemoglobin (HbA1c) level.

The method can further include a step 220, in which the subject-specific data entered into the digital interface by the subject is received. In some embodiments, the subject-specific data, or a portion thereof, is transmitted from the user-local device and received by a remote server. In some cases, the remote server includes a comparison engine. In some cases, the remote server transmits the subject-specific data or a component thereof to a comparison engine. The method can further include 235, comparing a rate or number of the subject specific data with a database of entry activity by prior subjects.

The comparison engine can output a prediction of likelihood of milestone achievement based on the entry activity by prior subjects. The likelihood can be determined as a function of engagement with the digital interface (i.e., number of times a subject has entered one or more, or all, subject-specific data), engagement with the lifestyle regimen (i.e., rate of compliance with lifestyle regimen activities, meal plans and the like). The likelihood can be determined as a function of one or more compliance parameters (e.g., true, false, number, or rate). For example, the likelihood can be determined as a function of whether a meal plan was followed or logged; or if not, whether a meal fallback was consumed or logged; whether a lifestyle regimen activity was completed or logged; whether a coaching call was completed or logged; whether ingredients on a lifestyle regimen shopping list were procured or logged; whether the subject consumed a specified amount of water or whether water-intake was logged; a number of meal plan meals consumed, a number of activities completed, a total amount of time (e.g., minutes) engaged in one or more activities, a number of coaching calls completed, length of one or more coaching calls, a number or fraction of ingredients procured from a shopping list, a number of hydration events, a total volume of hydration logged, or a number or rate of body weight measurements performed. In some cases, the likelihood can be determined as a function of type, frequency, duration, and/or intensity of exercise completed and/or logged.

In preferred embodiments, the prediction is a function of 2, 3, 4, 5, 6, 7, 8, 9, 10, or more of a number, count, rate, intensity, length of, or entry activity of meal plan use; meal fallback; physical activity; coaching call; shopping list use; water-intake; a number of meal plan meals consumed, or a body weight measurement.

The method can further include 240, providing the subject with milestone achievement input. The milestone achievement input can be a communication (e.g., displayed by the digital interface) that indicates likelihood of achieving a milestone. The milestone achievement input can be in the form of a graphical icon or a numerical score, or a combination thereof.

The milestone achievement input can suggest additional or alternative lifestyle interventions or regimens for increasing the likelihood or degree of milestone achievement. In some case, the milestone achievement input communicates a number, degree, or proportion by which the subject, in one or more compliance parameters, has lagged prior individuals in the database that successfully achieved the milestone, or has lagged a population of prior individuals in the database, which population of prior individuals is overrepresented by milestone achievers as compared to the average individual. In some cases, the milestone achievement input communicates a number, degree, or proportion by which the subject, in one or more compliance parameters, has lagged an average (mean or median) of a population of prior individuals in the database that successfully achieved the milestone, or has lagged in the database, which population of prior individuals is overrepresented by milestone achievers as compared to the average individual. In some cases, the population is a selected sub-population of prior individuals that is matched to a subject's age, age range, gender, cardiometabolic disorder, body mass index, or body mass index range.

In some cases, the milestone achievement input can suggest or provide for and/or schedule a follow-up meeting with one or more human service providers (e.g., health coach, dietician, nutritionist, chef-educator, nurse practitioner, physical therapist, kinesiologist, physician, behavioral psychologist, psychiatrist, and the like). Such care-escalation protocols can include a suggestion to complete one or more individual (one-on-one) or small-group coaching sessions with a medical service provider (e.g., nurse practitioner, physical therapist, kinesiologist, physician, behavioral psychologist, psychiatrist, and the like). In some cases, where a subject enters a low number, count, rate, intensity, or entry activity of meal plan use; meal fallback; shopping list use; or number of meal plan meals consumed, the methods described herein can include a suggestion to complete one or more individual (one-on-one) or small-group coaching sessions with a health coach, dietician, nutritionist, chef-educator and/or combinations thereof.

The milestone achievement input can be a communication (e.g., displayed by the digital interface) that is configured to increase engagement with the digital interface. For example, the communication can request entry of subject-specific data for one or more compliance parameters. In some embodiments, the method can include monitoring entry activity for one or more compliance parameters, detecting an absence of entry activity or an entry activity that is below a threshold and providing a milestone achievement input that requests or encourages entry activity. In some embodiments, the method can include monitoring entry activity for one or more compliance parameters, detecting an absence of entry activity indicating completion of one or more compliance parameters or an entry activity indicating completion of one or more compliance parameters that is below a threshold and providing a milestone achievement input that requests or encourages entry activity, and/or requests or encourages completion of one more compliance parameters.

In some embodiments the method or portions thereof is repeated one or more times. For example, after receiving the subject-specific data 220, the digital interface 210 can be provided to the subject for entry into the digital interface of subject specific data for one or more validated compliance parameters. Additionally or alternatively, the method can be repeated after the comparing step of 235. Additionally or alternatively, the method can be repeated after the providing step of 240. The repeating can be at a set frequency, such as hourly, daily, weekly, etc. (e.g., throughout the duration of the lifestyle intervention regimen). Alternatively, the repeating can be for a set number of times throughout the duration of the lifestyle intervention regimen. For example, the method can provide the digital interface for entry of subject-specific data about 2, 3, 4, 5, 6, 7, 8, 9, 10, 11, 12, 13, 14, 15, 16, or more times for the duration of the lifestyle intervention regimen. As another example, the repeating can be on a continual basis or initiated by the subject's access of the digital interface on the user-local device.

In some embodiments, a method 300 is provided, including step 310 providing a digital interface to a subject having or at risk of having a cardiometabolic disorder. Typically, the digital interface is displayed on a user-local device. In some cases, the digital interface is provided by transmitting instructions to display the digital interface from a remote server to the user-local device. In other cases, the instructions to display the digital interface can be stored on the user-local device. In yet other cases, a portion of the instructions to display the digital interface can be stored on the user-local device, and a portion of the instructions transmitted to the user-local device from a remote server. The instructions can be stored and/or transmitted in the form of transitory or non-transitory computer readable media.

The digital interface of this embodiment is configured to receive subject-specific data for one or more validated compliance parameters that is entered by the subject via the digital interface. The validated compliance parameters can be validated as associated with a therapeutic milestone for a specified cardiometabolic disorder that a subject has or is at risk of having. The therapeutic milestone can be an improvement in cardiometabolic health condition, or a target level of improvement in a cardiometabolic health condition. In some cases, the therapeutic milestone for the cardiometabolic disorder is selected by the subject via the digital interface. In other cases, the therapeutic milestone for the cardiometabolic disorder is pre-selected by the digital interface provider or a reference physician.

The method can further include a step 315*b*, in which a subject enters subject-specific data for one or more validated compliance parameters. Such data can include one or more of the following: whether a meal plan was followed; whether a lifestyle regimen activity was completed; whether a coaching call was completed; whether one or more, or all, ingredients on a shopping list were procured; whether the subject consumed a specified amount of water or whether the subject consumed water; a number of meal plan meals consumed, a number of activities completed, a total amount of time (e.g., minutes) engaged in one or more activities, a number of coaching calls completed, length of one or more coaching calls, a number or fraction of ingredients procured from a shopping list, a number of hydration events, or a total volume of hydration. In some cases, where a meal plan was not followed, the data can include whether a meal fallback was consumed. In some cases, data can include type, frequency and/or intensity of exercise completed and/or logged. In some cases, data can include number or frequency of body weight measurements performed.

In preferred embodiments, the dietary regiments employed in the subject methods comprise, consist essentially of or consist of a plant-based diet, i.e., they preferably comprise one or more ingredients taken from the general classes of vegetables, fruits, legumes, whole grains, and/or nuts and seeds.

In some cases, the data can be received, stored, and/or transmitted as a Boolean variable (e.g., true or false). For example, meal plan use data can be stored as a true indicating a meal plan was used (i.e., the meal specified by the meal plan was consumed) or a false indicating that a meal plan was not used (i.e., the meal specified by the meal plan was not consumed). In some cases, the data can be received, stored, and/or transmitted as a numerical variable (e.g., amount of time engaged in one or more exercise activities, number of meals consumed, or number of coaching calls completed).

In an optional step 315*c*, that may be present or absent in this embodiment, the subject enters one or more body metric measurements. The one or more body metric measurements can be or include body weight, lipid profile, cholesterol level, triglyceride levels, low-density lipoprotein level, high-density lipoprotein level, very low-density lipoprotein level, blood pressure, fasting blood glucose level, pre-prandial blood glucose level, post-prandial blood glucose level, blood insulin level, blood GIP level, insulin resistance, or glycated hemoglobin (HbA1c) level.

The method can further include a step 320, in which the subject-specific data entered into the digital interface by the subject is received. In some embodiments, the subject-specific data, or a portion thereof, is transmitted from the user-local device and received by a remote server. In some cases, the remote server includes a comparison engine. In some cases, the remote server transmits the subject-specific data or a component thereof to a comparison engine. The method can further include 335, comparing a rate or number of the subject specific data with a database of entry activity by prior subjects.

The comparison engine can output a milestone achievement input such as a prediction of likelihood of achievement of the therapeutic milestone for the cardiometabolic disorder based on the entry activity by prior subjects. The milestone achievement input (e.g., likelihood of achievement of therapeutic milestone) can be determined as a function of engagement with the digital interface (i.e., number of times a subject has entered one or more, or all, subject-specific data), engagement with the lifestyle regimen (i.e., rate of compliance with lifestyle regimen activities, meal plans and the like). The milestone achievement input can be determined as a function of one or more compliance parameters (e.g., true, false, number, or rate). For example, the milestone achievement input can be determined as a function of whether a meal plan was followed or logged; or if not, whether a meal fallback was consumed or logged; whether a lifestyle regimen activity was completed or logged; whether a coaching call was completed or logged; whether ingredients on a lifestyle regimen shopping list were procured or logged; whether the subject consumed a specified amount of water or whether water-intake was logged; a number of meal plan meals consumed, a number of activities completed, a total amount of time engaged in one or more exercise activities, a number of coaching calls completed, length of one or more coaching calls, a number or fraction of ingredients procured from a shopping list, a number of hydration events, a total volume of hydration logged, or a number or rate of body weight measurements performed. In some cases, the milestone achievement input can be determined as a function of type, frequency and/or intensity of exercise completed and/or logged.

For example, if a subject enters a low number of subject-specific datapoints (e.g., either relative to other members of the subject cohort, or relative to prior subjects in the database, or a portion thereof such as a matched subpopulation of prior subjects) into the digital interface, the comparison engine can indicate that the subject is unlikely to achieve a therapeutic milestone. As another example, if a subject enters a high number of subject-specific datapoints into the digital interface, the comparison engine can indicate that the subject is likely to achieve a therapeutic milestone. As another example, if a subject enters a low number of subject-specific datapoints, or a low number of datapoints indicating successful completion of dietary and/or exercise activities specified in the lifestyle intervention regimen, the comparison engine can provide a milestone achievement input requesting or encouraging additional entry activity and/or requesting or encouraging additional completion and entry of activities specified in the lifestyle intervention regimen.

As yet another example, if a subject enters into the digital interface a high number of meal plan meals consumed, the comparison engine can indicate that the subject is likely to achieve a therapeutic milestone. As yet another example, if a subject enters into the digital interface a low number of meal plan meals consumed, the comparison engine can indicate that the subject is unlikely to achieve a therapeutic milestone. As yet another example, if a subject enters into the digital interface a high number of meal fallbacks consumed, the comparison engine can indicate that the subject is likely to achieve a therapeutic milestone. As yet another example, if a subject enters into the digital interface a low number of meal fallbacks consumed, the comparison engine can indicate that the subject is unlikely to achieve a therapeutic milestone.

As yet another example, if a subject enters into the digital interface a high number of completed coaching calls, the comparison engine can indicate that the subject is likely to achieve a therapeutic milestone. As yet another example, if a subject enters into the digital interface a low number of completed coaching calls, the comparison engine can indicate that the subject is unlikely to achieve a therapeutic milestone. As yet another example, if a subject enters into the digital interface a high number of completed activities, the comparison engine can indicate that the subject is likely to achieve a therapeutic milestone. As yet another example, if a subject enters into the digital interface a low number of completed activities, the comparison engine can indicate that the subject is unlikely to achieve a therapeutic milestone.

As yet another example, if a subject enters into the digital interface a high number of meal water-intake events, the comparison engine can indicate that the subject is likely to achieve a therapeutic milestone. As yet another example, if a subject enters into the digital interface a low number of water-intake events, the comparison engine can indicate that the subject is unlikely to achieve a therapeutic milestone. As yet another example, if a subject enters into the digital interface a high volume of water intake, the comparison engine can indicate that the subject is likely to achieve a therapeutic milestone. As yet another example, if a subject enters into the digital interface a low volume of water-intake, the comparison engine can indicate that the subject is unlikely to achieve a therapeutic milestone.

As yet another example, if a subject enters into the digital interface a high number of shopping list ingredients procured, the comparison engine can indicate that the subject is likely to achieve a therapeutic milestone. As yet another example, if a subject enters into the digital interface a low number of number of shopping list ingredients procured, the comparison engine can indicate that the subject is unlikely to achieve a therapeutic milestone. As yet another example, if a subject enters into the digital interface a high count of body weight measurement activities, the comparison engine can indicate that the subject is likely to achieve a therapeutic milestone. As yet another example, if a subject enters into the digital interface a low count of body weight measurement activities, the comparison engine can indicate that the subject is unlikely to achieve a therapeutic milestone.

In preferred embodiments, the prediction is a function of 2, 3, 4, 5, 6, 7, 8, 9, 10, or more of a number, count, rate, intensity, or entry activity of meal plan use; meal fallback; activity; coaching call; shopping list use; water-intake; a number of meal plan meals consumed, or a body weight measurement.

The method can further include 340, providing the subject with milestone achievement input. The milestone achievement input can be a communication (e.g., displayed by the digital interface) that indicates likelihood of achieving the therapeutic milestone. The milestone achievement input can be in the form of a graphical icon or a numerical score, or a combination thereof. The milestone achievement input can suggest additional or alternative lifestyle interventions or regimens for increasing the likelihood or degree of milestone achievement. In some case, the milestone achievement input communicates a number, degree, or proportion by which the subject, in one or more compliance parameters, has lagged prior individuals in the database that successfully achieved the milestone, or has lagged a population of prior individuals in the database, which population of prior individuals is overrepresented by milestone achievers as compared to the average individual.

For example in some embodiments, coaching call completion shows a strong positive correlation with weight loss. In this case, a subject who has entered a low number of completed coaching calls via a digital interface can be predicted as unlikely to achieve the weight loss milestone. The milestone achievement input can suggest completing more coaching calls, or indicate the difference between coaching calls completed by the subject and coaching calls completed by the highest weight loss quartile of the prior individuals in the database, or provide for and/or schedule a follow-up meeting with one or more human service providers (e.g., health coach, dietician, nutritionist, chef-educator, nurse practitioner, physical therapist, kinesiologist, physician, behavioral psychologist, psychiatrist, and the like). Such care-escalation protocols can include a suggestion to complete one or more individual (one-on-one) or small-group coaching sessions with a medical provider (e.g., nurse practitioner, physical therapist, kinesiologist, physician, behavioral psychologist, psychiatrist, or a combination thereof). In some cases, where a subject enters a low number, count, rate, intensity, or entry activity of meal plan use; meal fallback; shopping list use; or number of meal plan meals consumed, the methods described herein can include a suggestion to complete one or more individual (one-on-one) or small-group coaching sessions with a health coach, nutritionist, dietician, and/or chef-educator. In this way, more time-consuming and/or expensive human resources and/or personal medical care can be more efficiently implemented in escalating fashion when needed in order to assist the subject with their milestone achievement, and is not utilized with individuals who are likely to reach their milestone achievement in any event.

In some embodiments the method or portions thereof is repeated one or more times. For example, after receiving the subject-specific data 320, the digital interface 310 can be provided to the subject for entry into the digital interface of subject specific data for one or more validated compliance parameters. Additionally or alternatively, the method can be repeated after the comparing step of 335. Additionally or alternatively, the method can be repeated after the providing step of 340. The repeating can be at a set frequency, such as hourly, daily, weekly, etc. (e.g., throughout the duration of the lifestyle intervention regimen). Alternatively, the repeating can be for a set number of times throughout the duration of the lifestyle intervention regimen. For example, the method can provide the digital interface for entry of subject-specific data about 2, 3, 4, 5, 6, 7, 8, 9, 10, 11, 12, 13, 14, 15, 16, or more times for the duration of the lifestyle intervention regimen. As another example, the repeating can be on a continual basis or initiated by the subject's access of the digital interface on the user-local device.

In some embodiments, a method 400 is provided, including step 410 providing a digital interface to a subject having or at risk of having a cardiometabolic disorder. Typically, the digital interface is displayed on a user-local device. In some cases, the digital interface is provided by transmitting instructions to display the digital interface from a remote server to the user-local device. In other cases, the instructions to display the digital interface can be stored on the user-local device. In yet other cases, a portion of the instructions to display the digital interface can be stored on the user-local device, and a portion of the instructions transmitted to the user-local device from a remote server. The instructions can be stored and/or transmitted in the form of transitory or non-transitory computer readable media.

The digital interface of this embodiment is configured to receive subject-specific data for one or more validated compliance parameters that is entered by the subject via the digital interface. The validated compliance parameters can be validated as associated with a therapeutic milestone for the cardiometabolic disorder. The therapeutic milestone can be an improvement in cardiometabolic health condition, or a target level of improvement in a cardiometabolic health condition. In some cases, the therapeutic milestone for the cardiometabolic disorder is selected by the subject via the digital interface. In other cases, the therapeutic milestone for the cardiometabolic disorder is pre-selected by the digital interface provider or a reference physician.

The method can further include a step 415a, in which a subject receives from the digital interface a lifestyle intervention regimen. Typically, the lifestyle intervention regimen is displayed as a series of lifestyle activities (e.g., diet or meal plans, exercise plans, hydration instructions, etc.) or provided as a file containing the series of lifestyle activities.

The method can further include a step 415b, in which a subject enters subject-specific data for one or more validated compliance parameters. Such data can include one or more of the following: whether a meal plan was followed; whether a lifestyle regimen activity was completed; whether a coaching call was completed; whether one or more, or all, ingredients on a shopping list were procured; whether the subject consumed a specified amount of water or whether the subject consumed water; a number of meal plan meals consumed, a number of activities completed, a total amount of time engaged in one or more activities, a number of coaching calls completed, length of one or more coaching calls, a number or fraction of ingredients procured from a shopping list, a number of hydration events, or a total volume of hydration. In some cases, where a meal plan was not followed, the data can include whether a meal fallback was consumed. In some cases, data can include type, frequency and/or intensity of exercise completed and/or logged. In some cases, data can include number or frequency of body weight measurements performed.

In preferred embodiments, the dietary regiments employed in the subject methods comprise, consist essentially of or consist of a plant-based diet.

In some cases, the data can be received, stored, and/or transmitted as a Boolean variable (e.g., true or false). For example, meal plan use data can be stored as a true indicating a meal plan was used (i.e., the meal specified by the meal plan was consumed) or a false indicating that a meal plan was not used (i.e., the meal specified by the meal plan was not consumed). In some cases, the data can be received, stored, and/or transmitted as a numerical variable (e.g., amount of time engaged in one or more exercise activities, number of meals consumed, or number of coaching calls completed).

In an optional step 415c, that may be present or absent in this embodiment, the subject enters one or more body metric measurements. The one or more body metric measurements can be or include body weight, lipid profile, cholesterol level, triglyceride levels, low-density lipoprotein level, high-density lipoprotein level, very low-density lipoprotein level, blood pressure, fasting blood glucose level, pre-prandial blood glucose level, post-prandial blood glucose level, blood insulin level, blood GIP level, insulin resistance, or glycated hemoglobin (HbA1c) level.

The method can further include a step 420, in which the subject-specific data entered into the digital interface by the subject is received. In some embodiments, the subject-specific data, or a portion thereof, is transmitted from the user-local device and received by a remote server. In some cases, the remote server includes a comparison engine. In some cases, the remote server transmits the subject-specific data or a component thereof to a comparison engine. The method can further include 435, comparing a rate or number of the subject specific data with a database of entry activity by prior subjects.

The comparison engine can output a milestone achievement input such as a prediction of likelihood of achievement of the therapeutic milestone for the cardiometabolic disorder based on the entry activity by prior subjects. The milestone achievement input (e.g., likelihood of achievement of therapeutic milestone) can be determined as a function of engagement with the digital interface (i.e., number of times a subject has entered one or more, or all, subject-specific data), engagement with the lifestyle regimen (i.e., rate of compliance with lifestyle regimen activities, meal plans and the like). The milestone achievement input (e.g., likelihood of achievement of therapeutic milestone) can be determined as a function of one or more compliance parameters (e.g., true, false, number, or rate). For example, the milestone achievement input can be determined as a function of whether a meal plan was followed or logged; or if not, whether a meal fallback was consumed or logged; whether a lifestyle regimen activity was completed or logged; whether a coaching call was completed or logged; whether ingredients on a lifestyle regimen shopping list were procured or logged; whether the subject consumed a specified amount of water or whether water-intake was logged; a number of meal plan meals consumed, a number of activities completed, a total amount of time engaged in one or more activities, a number of coaching calls completed, length of one or more coaching calls, a number or fraction of ingredients procured from a shopping list, a number of hydration events, a total volume of hydration logged, or a number or rate of body weight measurements performed. In some cases, the milestone achievement input can be determined as a function of type, duration, frequency and/or intensity of exercise completed and/or logged.

For example, if a subject enters a low number of subject-specific datapoints (e.g., either relative to other members of the subject cohort, or relative to prior subjects in the database, or a portion thereof) into the digital interface, the comparison engine can indicate that the subject is unlikely to achieve a therapeutic milestone. As another example, if a subject enters a high number of subject-specific datapoints into the digital interface, the comparison engine can indicate that the subject is likely to achieve a therapeutic milestone. As another example, if a subject enters a low number of subject-specific datapoints, or a low number of datapoints indicating successful completion of dietary and/or exercise activities specified in the lifestyle intervention regimen, the comparison engine can provide a milestone achievement input requesting or encouraging additional entry activity and/or requesting or encouraging additional completion and entry of activities specified in the lifestyle intervention regimen.

As yet another example, if a subject enters into the digital interface a high number of meal plan meals consumed, the comparison engine can indicate that the subject is likely to achieve a therapeutic milestone. As yet another example, if a subject enters into the digital interface a low number of meal plan meals consumed, the comparison engine can indicate that the subject is unlikely to achieve a therapeutic milestone. As yet another example, if a subject enters into the digital interface a high number of meal fallbacks consumed, the comparison engine can indicate that the subject is likely to achieve a therapeutic milestone. As yet another example, if a subject enters into the digital interface a low number of meal fallbacks consumed, the comparison engine can indicate that the subject is unlikely to achieve a therapeutic milestone.

As yet another example, if a subject enters into the digital interface a high number of completed coaching calls, the comparison engine can indicate that the subject is likely to achieve a therapeutic milestone. As yet another example, if a subject enters into the digital interface a low number of completed coaching calls, the comparison engine can indicate that the subject is unlikely to achieve a therapeutic milestone. As yet another example, if a subject enters into the digital interface a high number of completed activities, the comparison engine can indicate that the subject is likely to achieve a therapeutic milestone. As yet another example, if a subject enters into the digital interface a low number of completed activities, the comparison engine can indicate that the subject is unlikely to achieve a therapeutic milestone.

As yet another example, if a subject enters into the digital interface a high number of meal water-intake events, the comparison engine can indicate that the subject is likely to achieve a therapeutic milestone. As yet another example, if a subject enters into the digital interface a low number of water-intake events, the comparison engine can indicate that the subject is unlikely to achieve a therapeutic milestone. As yet another example, if a subject enters into the digital interface a high volume of water intake, the comparison engine can indicate that the subject is likely to achieve a therapeutic milestone. As yet another example, if a subject enters into the digital interface a low volume of water-intake, the comparison engine can indicate that the subject is unlikely to achieve a therapeutic milestone.

As yet another example, if a subject enters into the digital interface a high number of shopping list ingredients procured, the comparison engine can indicate that the subject is likely to achieve a therapeutic milestone. As yet another example, if a subject enters into the digital interface a low number of number of shopping list ingredients procured, the comparison engine can indicate that the subject is unlikely to achieve a therapeutic milestone. As yet another example, if a subject enters into the digital interface a high count of body weight measurement activities, the comparison engine can indicate that the subject is likely to achieve a therapeutic milestone. As yet another example, if a subject enters into the digital interface a low count of body weight measurement activities, the comparison engine can indicate that the subject is unlikely to achieve a therapeutic milestone.

In preferred embodiments, the prediction is a function of 2, 3, 4, 5, 6, 7, 8, 9, 10, or more of a number, count, rate, intensity, or entry activity of meal plan use; meal fallback; activity; coaching call; shopping list use; water-intake; a number of meal plan meals consumed, or a body weight measurement.

The method can further include 440, providing the subject with milestone achievement input. The milestone achievement input can be a communication (e.g., displayed by the digital interface) that indicates likelihood of achieving the therapeutic milestone. The milestone achievement input can be in the form of a graphical icon or a numerical score, or a combination thereof. The milestone achievement input can suggest additional or alternative lifestyle interventions or regimens for increasing the likelihood or degree of milestone achievement. In some case, the milestone achievement input communicates a number, degree, or proportion by which the subject, in one or more compliance parameters, has lagged prior individuals in the database that successfully achieved the milestone, or has lagged a population of prior individuals in the database, which population of prior individuals is overrepresented by milestone achievers as compared to the average individual.

For example in some embodiments, coaching call completion shows a strong positive correlation with weight loss. In this case, a subject who has entered a low number of completed coaching calls via a digital interface can be predicted as unlikely to achieve the weight loss milestone. The milestone achievement input can suggest completing more coaching calls, or indicate the difference between coaching calls completed by the subject and coaching calls completed by the highest weight loss quartile of the prior individuals in the database, or provide for and/or schedule a follow-up meeting with one or more human service providers (e.g., health coach, dietician, nutritionist, chef-educator, nurse practitioner, physical therapist, kinesiologist, physician, behavioral psychologist, psychiatrist, and the like). Such care-escalation protocols can include a suggestion to complete one or more individual (one-on-one) or small-group coaching sessions with a medical provider (e.g., nurse practitioner, physical therapist, kinesiologist, physician, behavioral psychologist, psychiatrist, or a combination thereof). In some cases, where a subject enters a low number, count, rate, intensity, or entry activity of meal plan use; meal fallback; shopping list use; or number of meal plan meals consumed, the methods described herein can include a suggestion to complete one or more individual (one-on-one) or small-group coaching sessions with a health coach, nutritionist, dietician, and/or chef-educator.

In some embodiments of the method or portions thereof, is repeated one or more times. For example, after receiving the subject-specific data 420, the digital interface 410 can be provided to the subject for entry into the digital interface of subject specific data for one or more validated compliance parameters. Additionally or alternatively, the method can be repeated after the comparing step of 435. Additionally or alternatively, the method can be repeated after the providing step of 440. The repeating can be at a set frequency, such as hourly, daily, weekly, etc. (e.g., throughout the duration of the lifestyle intervention regimen). Alternatively, the repeating can be for a set number of times throughout the duration of the lifestyle intervention regimen. For example, the method can provide the digital interface for entry of subject-specific data about 2, 3, 4, 5, 6, 7, 8, 9, 10, 11, 12, 13, 14, 15, 16, or more times for the duration of the lifestyle intervention regimen. As another example, the repeating can be on a continual basis or initiated by the subject's access of the digital interface on the user-local device.

Cardiovascular Disease

Cardiovascular disease is the major cause of morbidity and mortality in the Western world (Brunzell et al. Lipoprotein Management in Patients with Cardiometabolic Risk, Diabetes Care 2008 31: 811-822), and the initial presentation of coronary arterial disease in particular manifests as sudden death in up to one-third of patients. Id. To more effectively address this rapidly growing public health problem the American Diabetes Association and the American College of Cardiology Foundation have also jointly developed and advocated for the treatment of cardiometabolic risk (CMR), which refers to a high lifetime risk of CVD. (Eckel et al. Preventing Cardiovascular Disease and Diabetes, Diabetes Care 2006 29:1697-1699). Notably, the risk factors for cardiovascular disease and type 2 diabetes often cluster, including obesity, insulin resistance, hyperglycemia, dyslipoproteinemia and hypertension. As such, a patient having or at risk of having a "cardiometabolic disorder" as described herein refers to a patient having one or more of these risk factors, e.g. including cardiovascular disease (stroke, heart failure, coronary artery disease and myocardial infarction), diabetes, and metabolic syndrome.

The term "cardiovascular disease" herein refers to any disease or disorder of the heart or blood vessels (i.e. arteries and veins) or any symptom thereof, or any disease or condition that causes or contributes to a cardiovascular disease." Non-limiting examples of cardiovascular diseases include acute cardiac ischemic events, acute myocardial infarction, angina, angina pectoris, arrhythmia, atrial fibrillation, atherosclerosis, arterial fibrillation, cardiac insufficiency, cardiovascular disease, chronic heart failure, chronic stable angina, congestive heart failure, coronary artery disease, coronary heart disease, deep vein thrombosis, diabetes, diabetes mellitus, diabetic neuropathy, diastolic dysfunction in subjects with diabetes mellitus, edema, essential hypertension, eventual pulmonary embolism, fatty liver disease, heart disease, heart failure, homozygous familial hypercholesterolemia (HoFH), homozygous familial sitosterolemia, hypercholesterolemia, hyperlipidemia, hyperlipidemia in HIV positive subjects, hypertension, hypertriglyceridemia, ischemic complications in unstable angina and myocardial infarction, low blood pressure, metabolic syndrome, mixed dyslipidemia, moderate to mild heart failure, myocardial infarction, obesity management, paroxysmal atrial/arterial fibrillation/fibrulation/flutter, paroxysmal supraventricular tachycardias (PSVT), particularly severe or rapid onset edema, platelet aggregation, primary hypercholesterolemia, primary hyperlipidemia, pulmonary arterial hypertension, pulmonary hypertension, recurrent hemodynamically unstable ventricular tachycardia (VT), recurrent ventricular arrhythmias, recurrent ventricular fibrillation (VF), ruptured aneurysm, sitisterolemia, stroke, supraventricular tachycardia, symptomatic atrial fibrillation/flutter, tachycardia, type-II diabetes, vascular disease, venous thromboembolism, ventricular arrhythmias, and other cardiovascular events.

Metabolic Disorders

The compositions and methods of the present invention also find advantageous use in the treatment and/or prophylaxis of a wide variety of clinical metabolic disorders, including obesity, prediabetes, Polycystic Ovary Syndrome, dislipidemia or disorders of lipid metabolism, as well as hyperglycemic conditions, such as insulin-dependent (type 1) or -independent (type 2) diabetes, as well as physiological conditions or disorders associated with or that result from the hyperglycemic condition. Thus, hyperglycemic conditions treatable by a method of the invention also include a histopathological change associated with chronic or acute hyperglycemia (e.g., diabetes). Particular examples include degeneration of pancreas (13-cell destruction), kidney tubule calcification, degeneration of liver, eye damage (diabetic retinopathy), diabetic foot, ulcerations in mucosa such as mouth and gums, excess bleeding, delayed blood coagulation or wound healing and increased risk of coronary heart disease, stroke, peripheral vascular disease, dyslipidemia, hypertension and obesity.

As used herein, the term "hyperglycemic" or "hyperglycemia," when used in reference to a condition of a patient, means a transient or chronic abnormally high level of glucose present in the blood of a patient. The condition can be caused by a delay in glucose metabolism or absorption such that the patient exhibits glucose intolerance or a state of elevated glucose not typically found in normal patients (e.g., in glucose-intolerant subdiabetic patients at risk of developing diabetes, or in diabetic patients). Fasting plasma glucose (FPG) levels for normoglycemia are less than about 100 mg/dl, for impaired glucose metabolism, between about 110 and 126 mg/dl, and for diabetics greater than about 126 mg/dl.

Metabolic disorders also include obesity or an undesirable body mass. Leptin, cholecystokinin, PYY and GLP-1 decrease hunger, increase energy expenditure, induce weight loss or provide normal glucose homeostasis. Disorders treatable also include those typically associated with obesity, for example, abnormally elevated serum/plasma LDL, VLDL, triglycerides, cholesterol, plaque formation leading to narrowing or blockage of blood vessels, increased risk of hypertension/stroke, coronary heart disease, etc.

The effect of improving a lifestyle-related health condition of a subject using one or more of the methods or systems described herein on aspects of diabetic disease can be evaluated according to methods known in the art and common practiced by physicians treating diabetic subjects.

Efficacy of treatment of diabetes/metabolic syndrome and diabetes-associated conditions with the compositions and methods described herein can be assessed using assays and methodologies known in the art. By way of example, quantitative assessment of renal function and parameters of renal dysfunction are well known in the art. Examples of assays for the determination of renal function/dysfunction include serum creatinine level; creatinine clearance rate; cystatin C clearance rate, 24-hour urinary creatinine clearance, 24-hour urinary protein secretion; Glomerular filtration rate (GFR); urinary albumin creatinine ratio (ACR); albumin excretion rate (AER); and renal biopsy.

Quantitative assessment of pancreatic function and parameters of pancreatic dysfunction or insufficiency are also well known in the art. Examples of assays for the determination of pancreas function/dysfunction include evaluating pancreatic functions using biological and/or physiological parameters such as assessment of islets of Langerhans size, growth and/or secreting activity, beta-cells size, growth and/or secreting activity, insulin secretion and circulating blood levels, glucose blood levels, imaging of the pancreas, and pancreas biopsy, glucose uptake studies by oral glucose challenge, assessment of cytokine profiles, blood-gas analysis, extent of blood-perfusion of tissues, and angiogenesis within tissues.

Additional assays for treatment of diabetes and diabetes-associated conditions are known in the art and are contemplated herein.

Hormone Modulation

The lifestyle intervention regimen also modulates hormone concentrations and/or concentrations of hormones including, but not limited to, GLP-1, GLP-2, GIP, oxyntomodulin, PYY, CCK, glycentin, insulin, glucagon, ghrelin, amylin, C-peptide and uroguanylin. Sampling of hormones can be performed frequently during or after the lifestyle intervention regimen and/or participating in one or more of the methods described herein. Subjects can be undergoing or not undergoing treatment to cause systemic inhibition of dipeptidyl-peptidase IV (DPP-IV) to augment the circulating half-life of the relevant hormones that can be degraded by DPP-IV.

In some embodiments, improving a lifestyle-related health condition of a subject using one or more of the methods or systems described herein modulates GLP-1. In some embodiments, improving a lifestyle-related health condition of a subject using one or more of the methods or systems described herein modulates GLP-2. In some embodiments, improving a lifestyle-related health condition of a subject using one or more of the methods or systems described herein modulates GIP.

In some embodiments, improving a lifestyle-related health condition of a subject using one or more of the methods or systems described herein modulates oxyntomodulin. In some embodiments, improving a lifestyle-related health condition of a subject using one or more of the methods or systems described herein modulates PYY. In some embodiments, improving a lifestyle-related health condition of a subject using one or more of the methods or systems described herein CCK. In some embodiments, improving a lifestyle-related health condition of a subject using one or more of the methods or systems described herein modulates glycentin.

In some embodiments, improving a lifestyle-related health condition of a subject using one or more of the methods or systems described herein modulates insulin. In some embodiments, improving a lifestyle-related health condition of a subject using one or more of the methods or systems described herein modulates glucagon. In some embodiments, improving a lifestyle-related health condition of a subject using one or more of the methods or systems described herein modulates, ghrelin.

In some embodiments, improving a lifestyle-related health condition of a subject using one or more of the methods or systems described herein modulates amylin. In some embodiments, improving a lifestyle-related health condition of a subject using one or more of the methods or systems described herein modulates C-peptide. In some embodiments, improving a lifestyle-related health condition of a subject using one or more of the methods or systems described herein modulates uroguanylin.

In embodiments, the levels of hormones assayed in association with the methods of the invention, including, but not limited to, GLP-1, GLP-2, GIP, oxyntomodulin, PYY, CCK, glycentin, insulin, glucagon, ghrelin, amylin, uroguanylin, C-peptide and/or combinations thereof are detected according to standard methods described in the literature. For example, proteins can be measured by immunological assays, and transcription products by nucleic acid amplification techniques. Functional assays described in the art can also be used as appropriate. In embodiments, samples assayed comprise cultured cells, patient cell or tissue samples, patient body fluids, e.g., blood or plasma, etc. Similarly, the levels of analytes (e.g., glucose, triglycerides, HDL, LDL, apoB and the like) assayed in association with the methods of the invention are detected according to any known method.

In some embodiments, patients are pre-evaluated for expression of metabolic hormones using methods described herein. The therapy provided to the individual can thus be targeted to his or her specific needs. In embodiments, a patient's hormonal profile is pre-evaluated and depending on the changes that the physician desires to affect, a certain lifestyle intervention regimen is administered. The evaluation process can be repeated and the treatment adjusted accordingly at any time during or following treatment.

Reducing Pharmaceutical Interventions

In some embodiments, the methods, systems, and computer program products described herein can achieve a therapeutic milestone in a subject having a cardiometabolic disorder or at risk of having a cardiometabolic disorder without pharmaceutical intervention or with a reduced dosing (e.g., dose amount and/or dose frequency) of one or more pharmaceutical interventions. For example, in a patient having or at risk of having type-II diabetes, a relevant therapeutic milestone can comprise, e.g., maintenance of HbA1c, fasting glucose, fasting insulin, alanine transaminase, and/or fasting lipids, and/or any other therapeutic milestone markers described herein relevant to evaluating diabetes treatment such as a hormone level, renal function biomarker, and the like, at a level indicative of a therapeutic benefit. In some cases, a patient having or at risk of having type-II diabetes can achieve one or more of the therapeutic milestones for type-II diabetes without pharmaceutical intervention or with a reduced dosing (e.g., dose amount and/or dose frequency) of one or more of biguanides; sulfonylureas; meglitinide derivatives; alpha-glucosidase inhibitors; thiazolidinediones (TZDs); glucagonlike peptide-1 (GLP-1) agonists; dipeptidyl peptidase IV (DPP-4) inhibitors; selective sodium-glucose transporter-2 (SGLT-2) inhibitors, and insulin.

As another example, in a patient having or at risk of heart disease, a relevant therapeutic milestone can comprise, e.g., weight loss, improved lipid profile, lower blood pressure, and/or lower resting pulse rate, or any other therapeutic milestone described herein relevant to evaluating treatment of heart disease. In some cases, a patient having or at risk of having heart disease can achieve one or more of the therapeutic milestones for heart disease without pharmaceutical intervention or with a reduced dosing (e.g., dose amount and/or dose frequency) of a beta-blocking agent, an alpha-blocking agent, an angiotensin-converting enzyme inhibitor, a statin, a diuretic, and a calcium channel blocker.

As another example, in a patient having or at risk of hypertension, a relevant therapeutic milestone can comprise, e.g., maintenance of a diastolic and/or systolic blood pressure, or any other therapeutic milestone described herein relevant to evaluating treatment of hypertension, at a level indicative of therapeutic benefit. In some cases, a patient having or at risk of hypertension can achieve one or more of the therapeutic milestones for hypertension without pharmaceutical intervention or with a reduced dosing (e.g., dose amount and/or dose frequency) of a beta-blocking agent, an alpha-blocking agent, an angiotensin-converting enzyme inhibitor, an angiotensin II receptor blocker, a calcium channel blocker, a diuretic, and a renin inhibitor.

As another example, in a patient having or at risk of hyperlipidemia, a relevant therapeutic milestone can comprise, e.g., maintenance of a diastolic and/or systolic blood pressure, or any other therapeutic milestone described herein relevant to evaluating treatment of hyperlipidemia, at a level indicative of therapeutic benefit. In some cases, a patient having or at risk of hyperlipidemia can achieve one or more of the therapeutic milestones for hyperlipidemia without pharmaceutical intervention or with a reduced dosing (e.g., dose amount and/or dose frequency) of a statin, exetimibe, and PCSK9 inhibitors statin.

As another example, in a patient having or at risk of coronary artery disease, a relevant therapeutic milestone can comprise, e.g., maintenance of a diastolic and/or systolic blood pressure, or any other therapeutic milestone described herein relevant to evaluating treatment of coronary artery disease, at a level indicative of therapeutic benefit. In some cases, a patient having or at risk of coronary artery disease can achieve one or more of the therapeutic milestones for hyperlipidemia without pharmaceutical intervention or with a reduced dosing (e.g., dose amount and/or dose frequency) of a) a cholesterol-modifying medication selected from the group consisting of a statin, exetimibe, and PCSK9 inhibitors; b) an anti-coagulant, preferably selected from the group consisting of an anti-platelet agent (e.g. aspirin or Plavix), warfarin, low-molecular weight heparin, a direct thrombin inhibitor, and a factor Xa inhibitor; c) a beta-blocking agent, d) a vasodilator; e) a diuretic; and f) an angiotensin-converting enzyme inhibitor and an angiotensin II receptor blocking agent.

Biguanides contemplated for reduction in accordance with the subject invention include, e.g. metformin, phenformin, buformin and like compounds described herein. Statins or HMG-CoA reductase inhibitors contemplated for reduction in accordance with the subject invention include, e.g. lovastatin, atorvastatin, fluvastatin, rosuvastatin, simvastatin, pravastatin, pitavastatin, and the like. Additional active agents contemplated for reduction in accordance with the subject compositions and methods include, e.g. anti-hypertensives and anti-platelet agents as well as diuretics, bile acid sequesterants, incretin enhancers and mimetics, oral anti-diabetic agents, anti-obesity agents, and anti-atherosclerotics.

Anti-hypertensives contemplated for reduction in accordance with the subject invention include, e.g., beta blockers (atenolol, betaxolol, metoprolol, nadolol, nebivolol, oxprenolol, pindolol, propranolol, timolol, etc.), alpha-1 blockers (alfuzosin, arotinolol, doxazosin, indoramin, moxisylyte, phenoxybenzamine, phentolamine, prazosin, silodosin, tamsulosin, terazosin, tolazoline, trimazosin), alpha-2 agonists (apraclonidine, brimonidine, clonidine, guanabenz, guanfacine, lofexidine, tolonidine, mixed alpha/beta blockers (bucindolol, carvedilol, labetalol, etc.), calcium channel blockers such as dihydropyridines (amlodipine, felodipine, isradipine, lercanidipine, nicardipine, nifedipine, nimodipine, nitrendipine, etc.) and non-dihydropyridines (diltiazem, verapamil, etc.), renin inhibitors (aliskiren), ACE inhibitors (captopril, enalapril, fosinopril, lisinopril, perindopril, quinapril, ramipril, trandolapril, benazepril, etc.), angiotensin II receptor antagonists (candesartan, eprosartan, irbesartan, losartan, olmesartan, telmisartan, valsartan, etc.), and the like.

Anti-platelet medications contemplated for reduction in accordance with the subject invention include, e.g., cyclooxygenase inhibitors (acetylsalicylic acid (aspirin), aloxiprin, carbasalate calcium, indobufen, trifusal, etc.), ADP receptor inhibitors (clopidogrel, ticlopidine, ticagrelor, etc.), phosphodiesterase inhibitors (cilostazol, etc.), adenose reuptake inhibitors (dipyridamole, etc.), thromboxane synthase or receptor inhibitors (picotamide, ramatroban, terbogrel, etc.), anagrelide, prasugrel, cloricromen, and the like.

Diuretics contemplated for reduction in accordance with the subject invention include e.g., loop diuretics (bumetanide, ethacrynic acid, furosemide, torsemide, etc.), thiazide diuretics (epitizide, hydrochlorothiazide, chlorothiazide, bendroflumethiazide, etc.), thiazide-like diuretics (indapamide, chlorthalidone, metolazone, etc.), potassium-sparing diuretics (amiloride, triamterene, spironolactone, etc.), and the like.

Bile acid sequesterants contemplated for reduction in accordance with the subject invention include, e.g., cholestyramine, colesevelam, colestipol, and the like.

Suitable incretin mimetics and enhancers for use in the subject invention include, e.g., peptidic and non-peptidic GLP-1 mimetics (including, e.g., allosteric activators of the GLP-1 receptor), peptidic and non-peptidic PYY mimetics, peptidic and non-peptidic Ghrelin antagonists and the like.

Suitable oral anti-diabetic agents for use in combination with metformin in the subject compositions and methods include, e.g., sulfonylureas (glyburide, glimepiride, glipizide, gliclazide, glycopyramide, gliquidone, tolbutamide, acetohexamide, tolazamide, chlorpropamide, carbutamide, etc.), nonsulfonylureas (repaglinide, nateglinide, etc.), thiazolidinediones (rosiglitazone, pioglitazone, rivoglitazone, troglitazone, ciglitazone, darglitazone, netoglitazone, englitazone, etc.), dual PPAR agonists (e.g., aleglitazar, farglitazar, muraglitazar, tesaglitazar, telmisartan, and the like), dipeptidyl peptidase-4 inhibitors (vildagliptin, sitagliptin, saxagliptin, linagliptin, alogliptin, septagliptin, berberine, etc.), sodium-glucose co-transporter-1 or 2 (SGLT1 or 2) inhibitors (canagliflozin, empagliflozin, dapagliflozin, LX4211, etc.) meglitinides (nateglinide, repaglinide, etc.), alpha-glucosidase inhibitors (acarbose, miglitol, voglibose, etc.), agonists of GPR40, GPR120, GPR119, GPR41, GPR43, and the like.

Suitable anti-obesity agents for use for use in the subject invention include, e.g., Orlistat (Zenical), Lorcaserin (Belviq), Sibutramine (Meridia, withdrawn from most markets), Rimonabant (Acomplia), Exenatide (Byetta and Bydureon), Pramlintide (Symlin), Redux, ZGN-433, Phentermine/topiramate (Qsymia), Naltrexone/buproprion (Contrave), as well as alternative medicine options including, e.g., conjugated linoleic acid, green tea extract, khat, lipoic acid, ECA Stack (Ephedrine Caffeine Stack), Raspberry ketone and the like.

Suitable anti-artherosclerotics for use in the subject invention include compounds that can reduce atherosclerosis independent of changes in other risk factors, e.g. fish oil as well as inhibitors of proprotein convertase subtilisin/kexin type 9 (PCSK9) such as AMG145 (Amgen), 1D05-IgG2 (Merck & Co.), and SAR236553/REGN727 (Aventis/Regeneron), peptides mimicking the LDLR that binds to PCSK9 (e.g. Shan et al. (2008) *Biochem. Biophys. Res. Commun.* 375: 69-73), and nucleic acid therapeutics targeting PCSK9 (e.g Graham et al. (2007) *J Lipid Res.* 48:763-7; Lindholm et al. (2012) *Mol. Ther.* 20:376-81).

Also contemplated as additional active agents are HDL/LDL ratio modifying compounds including, e.g., niacin, acipomox, MK-0354, other modulators of GPR81, GPR109A, GPR109B and the like.

Definitions

"Treating" or "treatment" of any condition, disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers preventing or to delaying the onset of the disease or disorder.

"Therapeutically effective amount" or "effective amount" means the amount of a composition, compound, therapy, or course of treatment that, when administered to an individual for treating a disorder or disease, is sufficient to effect such treatment for the disorder or disease. The "therapeutically effective amount" will vary depending on the composition, the compound, the therapy, the course of treatment, the disorder or disease and its severity and the age, weight, etc., of the individual to be treated.

Systems

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, smart watch or a smart phone, or a specialty device produced for the system Methods of the invention can be performed using software, hardware, firmware, hardwiring, or combinations of any of these. Features implementing functions can also be physically located at various positions, including being distributed such that portions of functions are implemented at different physical locations (e.g., digital interface in one location, computer server for providing said digital interface to user local device and/or receiving subject-specific data, and computer for hosting the database of entry activity by prior subjects in another location, e.g., in separate buildings, for example, with wireless or wired connections). In some cases, one or more functions are in the same location or on the same computer. For example, the function of hosting the database and comparing rate or number of subject-specific data with the database of entry activity by prior subjects can be performed on the same device, or a different device.

Processors suitable for the execution of computer programs include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user (e.g., the digital interface and/or the milestone achievement input) and an input or output device such as a keyboard and a pointing device, (e.g., a mouse or a trackball), by which the user can provide input to the computer. Other kinds of devices can be used to provide for interaction with a user as well, and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of a system can be interconnected through a network by any form or medium of digital data communication, e.g., a communication network. For example, a reference set of data (e.g., the database of entry activity by prior subjects) may be stored at a remote location and a computer can communicate across a network to access the reference set for purposes of comparing data. In other embodiments, however, a reference set is stored locally within the computer and the computer accesses the reference set within the CPU for purposes of comparing data. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers) to perform one or more of the methods described herein. A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art.

A computer program does not necessarily correspond to a file. A program can be transitory or non-transitory medium that is stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

Functions described above can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

EXAMPLES

Example 1

Participants were recruited for a 16-week pilot program We preferentially screened-in 601 participants to include women, in any US state, aged 45-54, with a BMI of 30-35 kg/m$^2$ (i.e. Class 1 Obesity), who also reported a willingness to prepare meals at home and eat mostly whole, plant-based foods. Ninety-five participants started the program and 71 (74.7%) completed the 16 weeks, with an average loss of body weight of 5.1% among all completers, and, in the top tertile of engagers (i.e. those who made the most use of the digital tools), we found an average of 7.1% weight loss in just over 14 weeks.

Certain participants having baseline metabolic abnormalities (i.e. elevated fasting glucose, fasting insulin, hemoglobin A1c, alanine transaminase (ALT), and/or fasting lipids) provided before and after program blood tests, allowing direct evaluation of clinical responses after their participation in the 16 week program. Among 7 participants with impaired glycemic responses at baseline, all 7 showed improvement in A1c (5 participants improved, with 3 of the 5 returning to normal) or insulin sensitivity (7 participants) at 16 weeks. Glycemic measures assessed include fasting blood glucose and insulin, hemoglobin A1e, and calculated HOMA2 (homeostatic model assessment-2) measures of beta-cell function and insulin resistance.

Example 2

In this study, we sought to understand to what degree a novel, skill-focused, digital therapeutic could change Hemoglobin A1e and anti-diabetic medication use in a geographically widely distributed sample of adults with type 2 diabetes. While the ultimate goal of the intervention is to be more cost-effective than other interventions, this study examines effectiveness alone.

Methods

Trial Design & Participants

We conducted a 12-week, non-blinded, single-arm interventional study in a convenience sample of adults with a self-reported diagnosis of Type 2 diabetes, targeting adults in any US state with an interest in type 2 diabetes. Eligibility criteria included having a diagnosis of type 2 diabetes, age 18 or older, and possession of an Android or iPhone Smartphone, as demonstrated by the ability to download the intervention app. Type 2 diabetes status was presumed by the combination of a self-reported diagnosis and an initial Hemoglobin A1c of 6.5% or higher. Participants were excluded if they were not able to comply with the study protocol, for example if they could not speak or read English or did not have sufficient computer literacy to operate the app successfully.

Enrollment was on a first-come-first-served basis and all data collection occurred online via electronic survey or directly through the app. Participants who were interested in the study were invited to download the app and enter a code to unlock the app. Participants were then instructed by the app to create an account using their email address. Upon creating an account, participants were emailed an informed consent document to review. Informed consent was obtained for each study participant via discussion with a study staff member prior to commencing their first coaching call. This phone call with study staff also ensured that each participant was unique.

Intervention

The digital therapeutic consisted of use of the intervention app paired with specialized human support, also delivered digitally. The content design of both app and human support incorporated evidenced-based dietary and lifestyle recommendations such as a dietary pattern consisting mainly of whole food plant-based meals and regular exercise meeting or exceeding national guidelines. Ley et al., *The Lancet* 383:1999-2007 (2014). Since increased meals prepared at home is associated with decreased disease burden, Zong et al. *PLOS Med* 13(7):e1002052 (2016), additional content was also developed with expert input to enhance culinary knowledge and skill acquisition with the aim of increasing meals prepared at home.

The app was designed to be used ad libitum, however expectations of use were established during the informed consent process as follows: 1. Use of the meal planning feature that facilitates advanced planning of meals and automated shopping lists (approximately 5 minutes per week). The meal planning feature used default recipes that met pre-specified criteria for ease-of-preparation, inclusion of easy-to-access, whole-food, plant-based ingredients, and staged introduction of culinary techniques. Participants could easily swap meals or plan to eat a meal not in the recipe database. 2. Self-monitoring of weight daily (via digitally connected scale provided free to participants or by self-report in app) and the option of reporting meals made (approximately 1-2 minutes per day). 3. Reviewing of educational materials aimed at advancing culinary or health literacy (approximately 15-20 minutes per week). 4. An optional, private Facebook community was created to provide additional peer-to-peer and expert-to-peer support (ad libitum). The app also delivered reminders, for example to schedule a coaching call or report meals made or eaten, in the form of in-app notifications and an ability to message their health coach.

The primary form of human support was delivered by 30-minute telephonic health coaching calls, scheduled at the participant's convenience every two weeks via the study app. Health coaching is an evidence-based practice grounded in behavior change theory that utilizes guided conversational techniques such as motivational interviewing. Wolever et al., *Glob Adv Health Med* 2(4):38-57 (2013). All study health coaches had completed training from accredited health coaching institutions and received additional training in lifestyle and culinary medicine, research methods, as well as training for coaching within a clinical team prior to the start of the study.

During the intervention period, the health coaches were supported by a specialized team of lifestyle medicine experts including a nurse practitioner, internist, psychiatrist, chef-educator, and registered dietitian, who were also available to speak to members on an as-needed basis via a care-escalation process. Participants were asked to continue managing all medications with their Primary Care Team or Endocrinologist during the course of the study.

Measures

Demographics

Participants reported age, gender, height, weight and US state of residence as a part of the signup process for the study app.

Hemoglobin A1c and Medication Use

Most recent Hemoglobin A1c and current diabetic medication use (name, dose and frequency of medication) were self-reported in the study app by participants. Participants were encouraged by their coaches to report any changes to medications within their study app. Email reminders were utilized to prompt entry of a follow-up Hemoglobin A1c and updated medications at 12 weeks. Medication and Hemoglobin A1c data were reviewed by two study authors (NLG, MAB). Participants were contacted by study staff (KLE, NLG) to help clarify potential reporting errors.

Engagement

Engagement with both the study app and coaching calls was measured automatically via the study app. Total engagement is defined as the average number of recorded app actions per day (e.g. planning or reporting meals, scheduling calls, building shopping lists, etc.).

End of program self-efficacy to manage diabetes and to maintain an optimal dietary pattern was measured via online survey questions using a Likert scale; this was emailed to participants during their 12th week.

Statistical Methods

Statistical analyses were performed using SAS software, version 9.4 (SAS Institute Inc.). Change over time of continuous variables was analyzed using two-tailed paired Student's t-test with alpha set at 0.05 and chi-square tests for differences in categorical variables. McNemar's test was used to evaluate medication change.

To evaluate the combined effects of medication and HbA1c change, we calculated a composite outcome measure defined as a decrease in diabetic medication use without an increase in HbA1c, or an improvement in HbA1c of at least 0.5% without an increase in diabetic medication use.

We used mixed-effects modeling to test the effects of baseline BMI, years since diagnosis of diabetes, net change in diabetes medications, total app engagement and baseline HbA1c on the mean change in HbA1c. To evaluate the intent-to-treat effect, we used a last-value-carried-forward approach for the missing data from participants who did not report follow-up Hemoglobin A1c's. Since effect-size can be modulated by baseline HbA1c [31] we also tested the effects of a log transformed HbA1c.

To investigate the relationship between engagement with the program and HbA1c, we first defined tertiles of app engagement using the sum of all actions taken in the app during the study. A general linear regression was used to test the effect of app use tertile with the change in HbA1c. Change in HbA1c was set as the dependent variable with tertile of app engagement, and the log transformed baseline HbA1c as independent variables. Using the least square means pairwise comparison, we tested the differences in changes in HbA1c by the tertiles of app engagement.

Results

Participants 123 individuals with self-reported type 2 diabetes and an initial Hemoglobin A1c of 6.5% or higher downloaded the intervention app, of which 118 (95.9% of downloads) consented to participation in the study. There were 9 dropouts (7.6% of consented) during the study. Of the remaining 109 participants, 94 (86.2%) were still using the app at 12-weeks and 101 (92.7%) provided some or all end-study data.

Baseline characteristics are summarized in Table 1. Participants from 38 US states consented to participate. 81.4% (n=96) were female, with a mean age of 50.7 years (SD 9.4) a mean BMI of 38.1 kg/m2 (SD 8.8) and a mean Hemoglobin A1c of 8.1% (SD 1.6) at baseline. There were no statistical differences in baseline characteristics between those who consented and those who submitted end-study data.

TABLE 1

| | Sample characteristics at baseline by program completion | | | |
| User Characteristics | Total (n = 118) | Completed Program (n = 109) | Submitted End Study Data[a] (n = 101) | P[b] |
|---|---|---|---|---|
| Female, n (%) | 96 (81.4) | 87 (79.8) | 80 (79.2) | .14 |
| Age (years), mean (SD) | 50.7 (9.4) | 50.4 (9.6) | 50.4 (9.7) | .85 |
| Geographic distribution, # U.S. states | 38 | 37 | 37 | .71 |
| Hemoglobin A1c (%), mean (SD) | 8.1 (1.6) | 8.2 (1.6) | 8.2 (1.7) | .81 |
| Body mass index (kg/m²), mean (SD) | 38.1 (8.8) | 38.4 (9.0) | 38.1 (8.9) | .99 |
| Time since diabetes diagnosis (years), | 2.6 (1.6) | 2.6 (1.5) | 2.6 (1.5) | .99 |

TABLE 1-continued

| | | | Submitted | |
|---|---|---|---|---|
| | | Completed | End Study | |
| | Total | Program | Data[a] | |
| User Characteristics | (n = 118) | (n = 109) | (n = 101) | P[b] |
| mean (SD) | | | | |
| Diabetes medications (count), mean (SD) | 1.4 (0.9) | 1.5 (0.9) | 1.5 (0.9) | .73 |

Sample characteristics at baseline by program completion

[a]Participants who submitted an end-study Hemoglobin A1c and/or self-efficacy survey
[b]P value comparing total sample to those submitting end study data Hemoglobin A1c Among participants who reported an end-study Hemoglobin A1c, 80.4% (78/97) had improvement of Hemoglobin Ale, with 58.8% (57/97) having a decrease of –0.5% or more, 39.2% (38/97) having a decrease of 1% or more, and 22.7% (22/97) having a follow-up Hemoglobin A1c<6.5%. The mean change was –0.8% (SD 1.3, P<0.001) over a mean interval of 3.5 months (SD 0.9). This change remained statistically significant in our mixed-effects model (P=0.003). Substituting the log transformed baseline HbA1c we found that the impact of baseline HbA1c was modulated and the significance of the mean change in HbA1c was improved (P<0.001). Using a last-value-carried-forward approach for the missing data from participants who did not report follow-up Hemoglobin A1c's, the mean change remained statistically significant (n=118, –0.6%, SD 0.9, P<0.001).

Among those with a baseline hemoglobin>7%, the mean change was –1.0% (n=69, SD 1.4, P<0.001). Excluding those who experienced a change in glycemic medication mid-study (n=2), the mean change in HbA1c was –1.1% (n=65, SD 1.4, P<0.001).

Medication Use

At the start of the study, participants reported taking an average of 1.4 diabetic medications (SD 0.9) with a self-reported average time since diagnosis of 2.6 years (SD 1.6). Of those reporting follow-up medication data (n=97), 4 (4.1%) changed medications or dosages within the 12-week study (i.e. their medication changes were likely to impact follow-up HbA1c). In conjunction with reporting an end-study hemoglobin A1c, 16 participants (16.5%) reported decreasing or stopping one or more diabetic medications and 8 (8.3%) increased or added one or more diabetic medications. The frequency of decreased medication use (either decreasing dose or stopping a medication) compared to baseline medication use was statistically significant (P<0.001).

Using the composite outcome measure defined above, 56.7% of participants (55/97) met the composite outcome of reducing HbA1c, reducing diabetic medication use or both.

Program Engagement

Of the 118 individuals who consented to participate, 109 (92.4%) were active in the study at the end of the 12-week intervention period and 95 of 109 (86.2%) were still utilizing the app. Total distinct app engagements averaged 4.3 per day (SD 2.5) and average number of coaching calls completed was 4.1 (SD 1.8) during the 12-week period.

Figure 1:
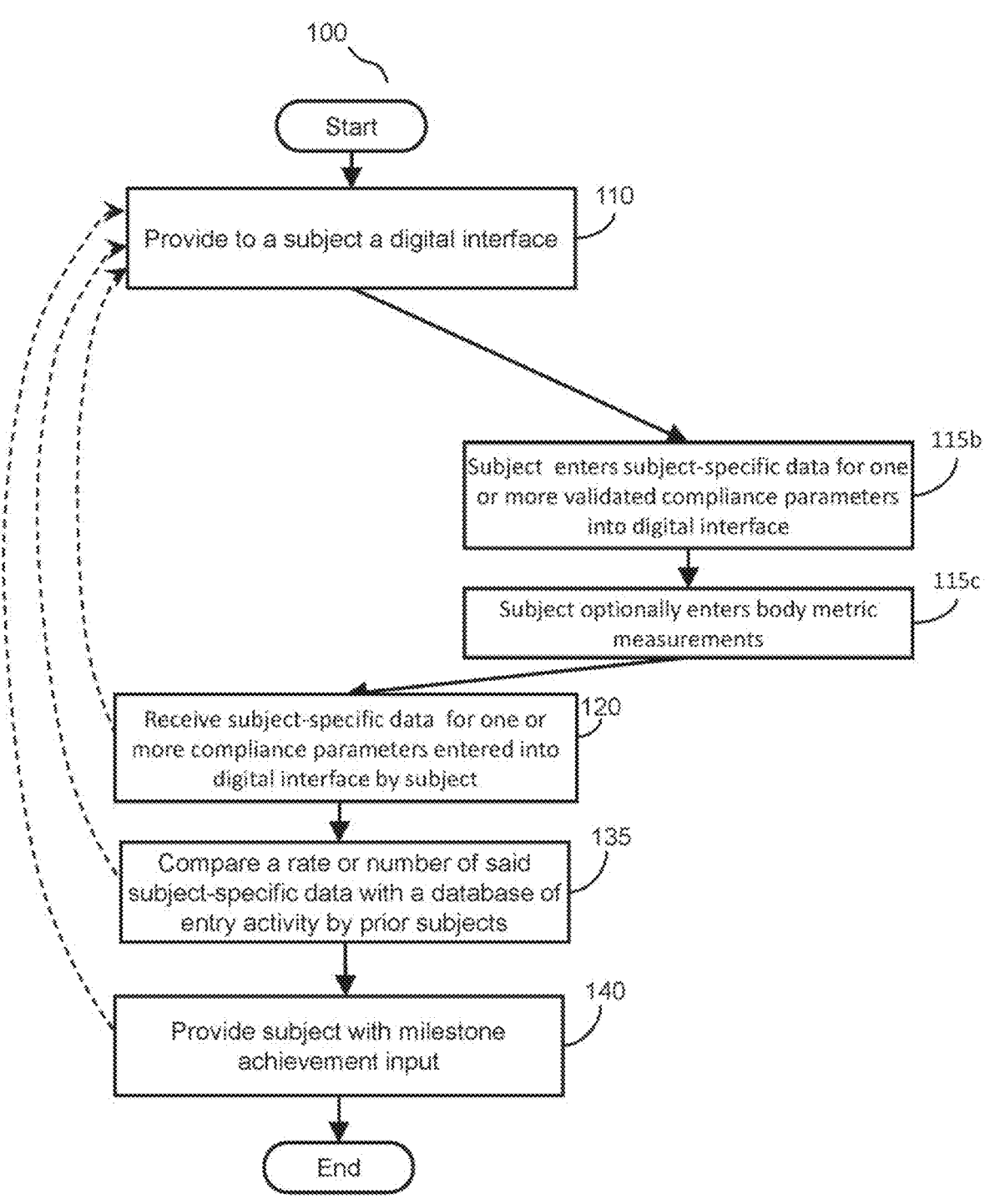
FIG. 1 is a flow chart of an embodiment of a method for improving a lifestyle-related health condition of a subject.
Figure 2:
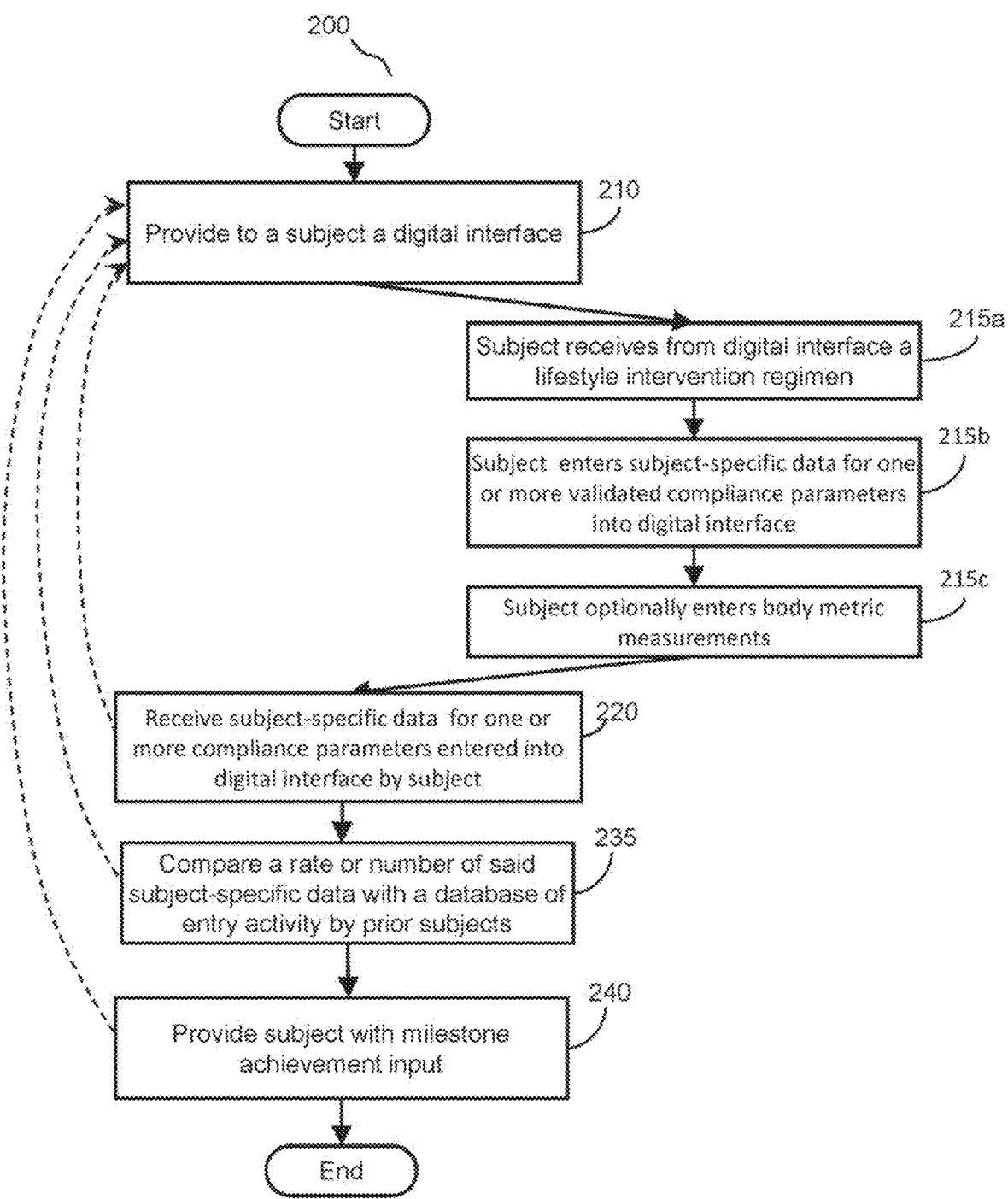
FIG. 2 is a flow chart of an embodiment of a method for improving a lifestyle-related health condition of a subject.
Figure 4:
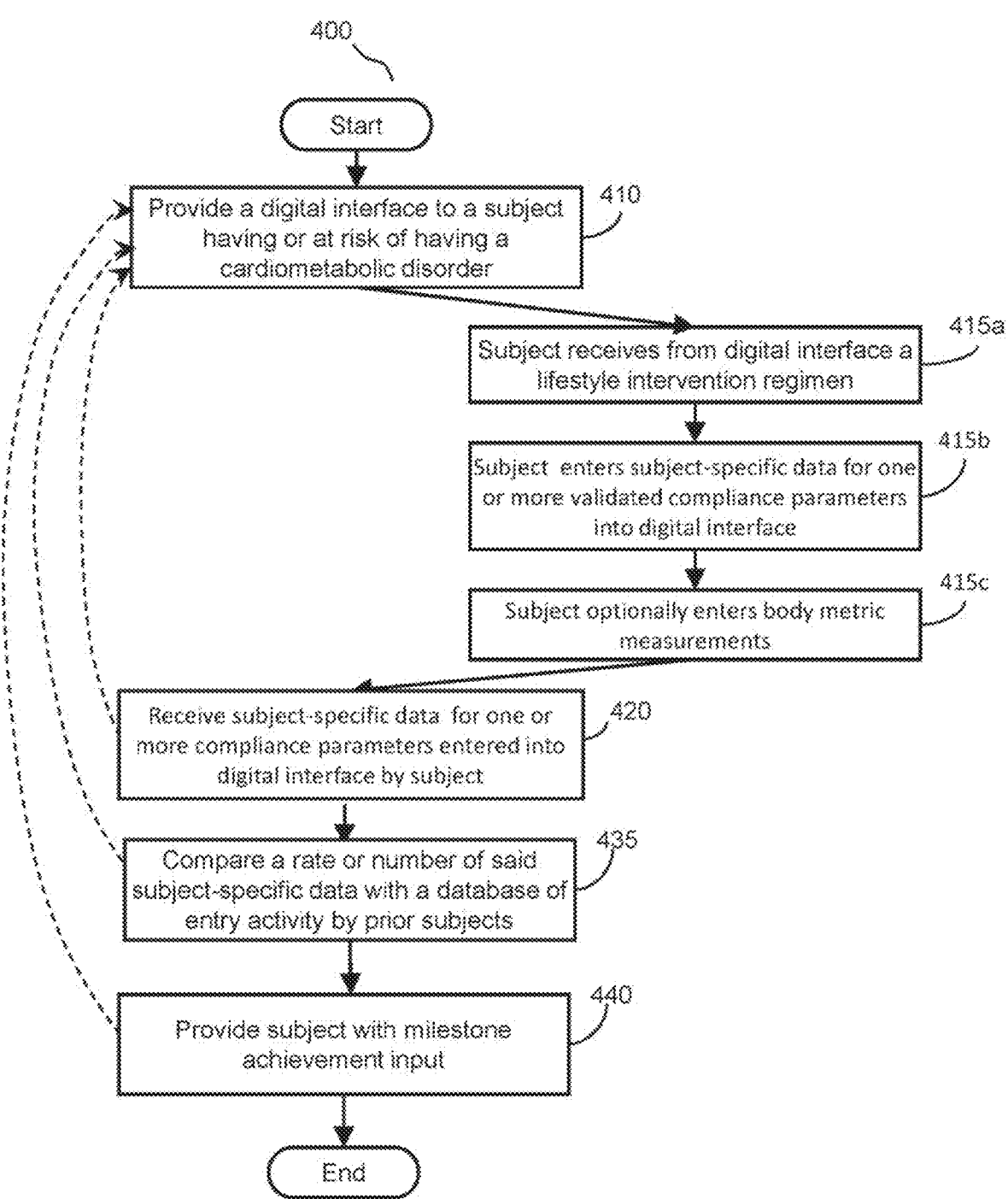
FIG. 4 is a flow chart of an embodiment of a method for treating a subject having or at risk of having a cardiometabolic disorder.
Figure 5:
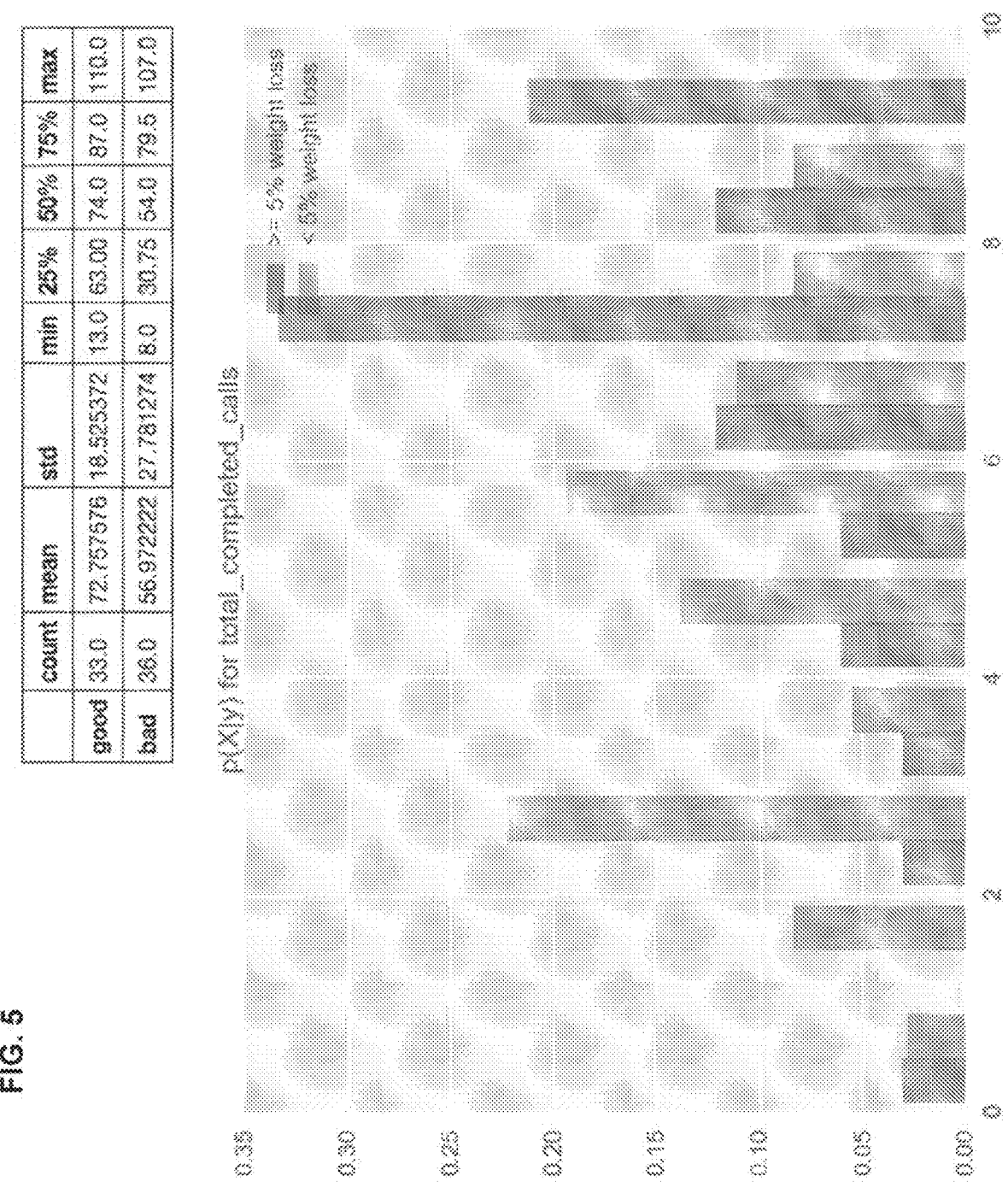
FIG. 5 illustrates data from performing an embodiment of a method disclosed herein. The data indicate that the number of completed coaching calls entered into the digital interface is positively correlated with a weight loss milestone.
Figure 6:
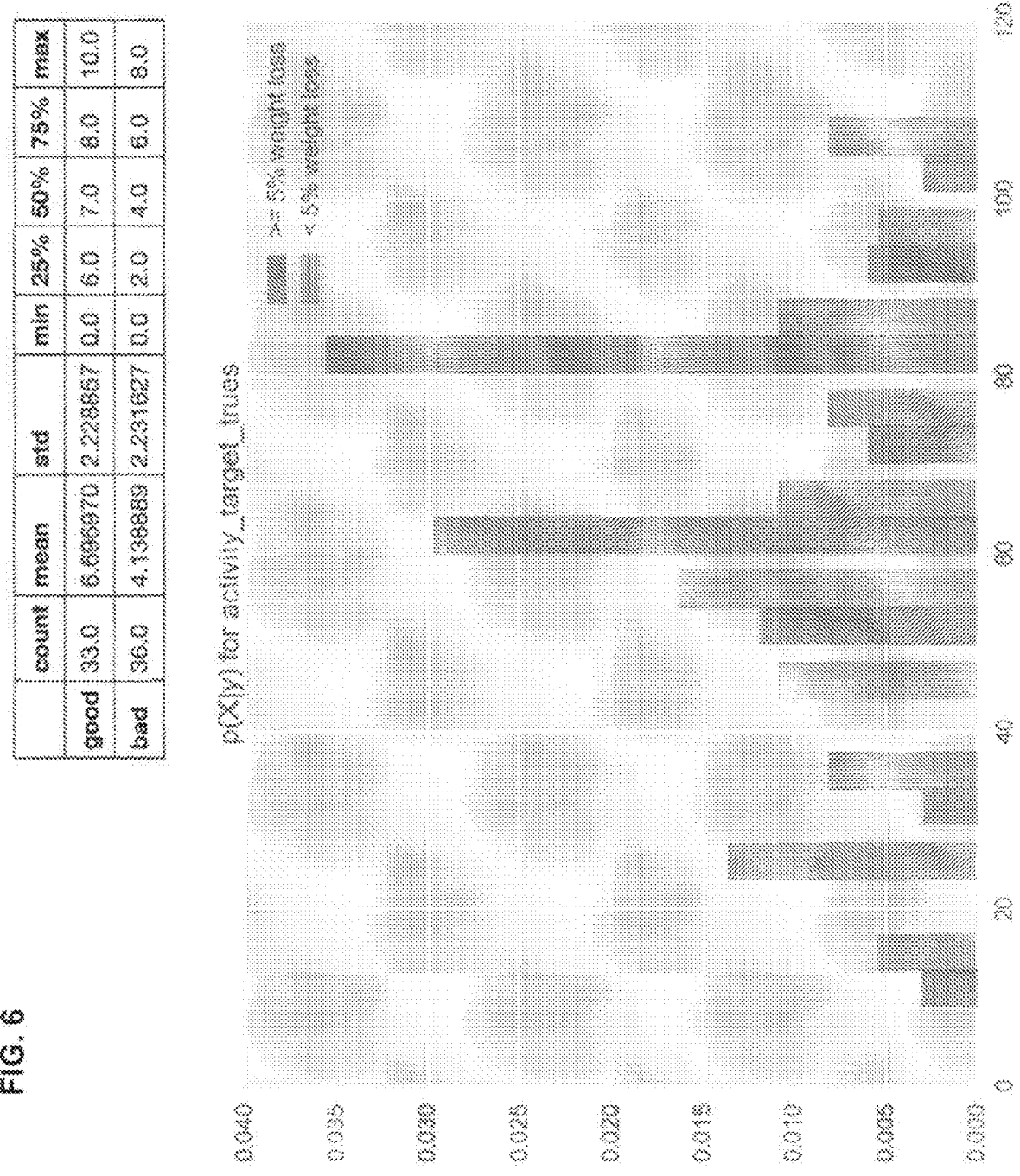
FIG. 6 illustrates data from performing an embodiment of a method disclosed herein. The data indicate that the number of entries into the digital interface that indicate completion of an activity target is positively correlated with a weight loss milestone.
Figure 7:
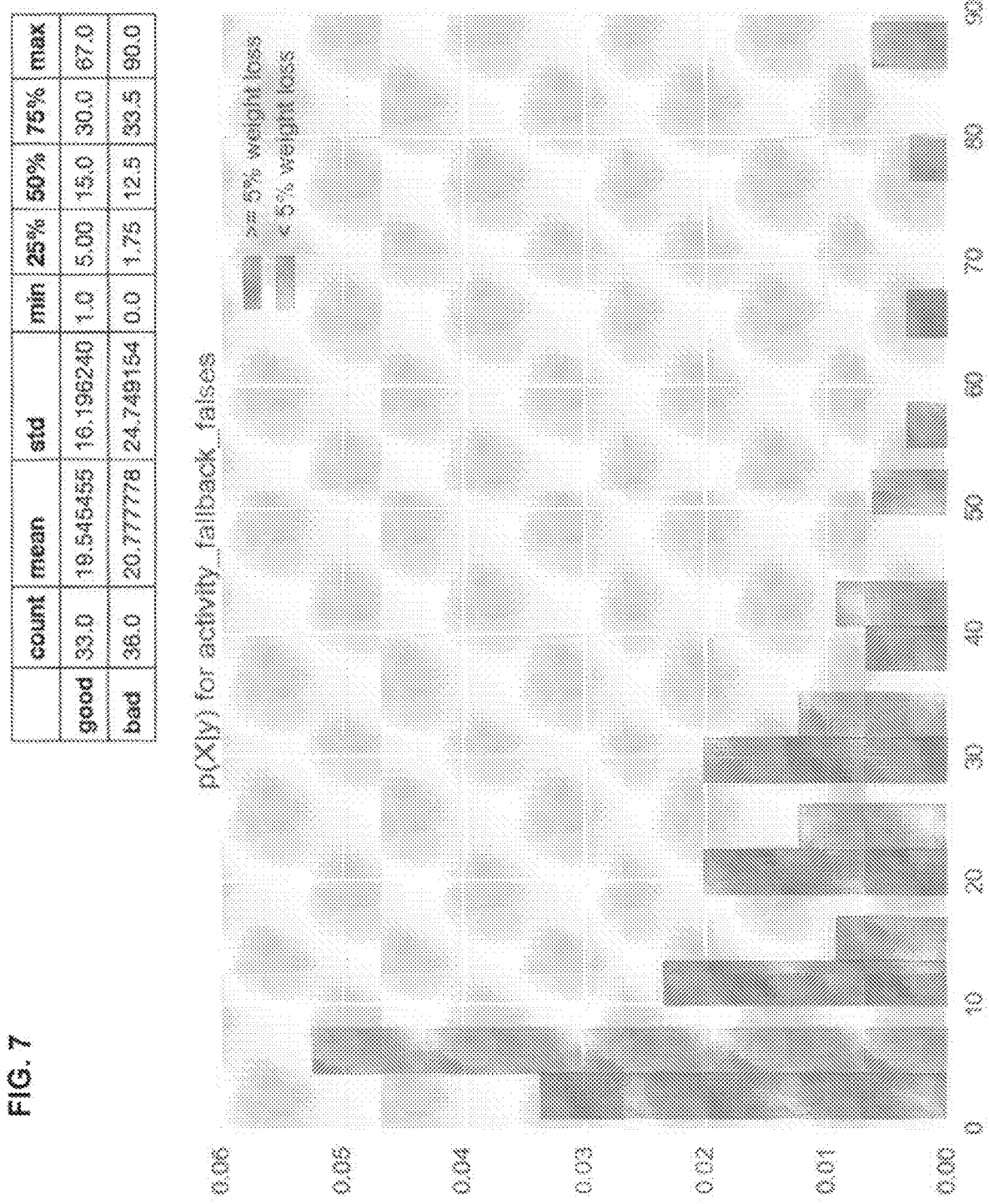
FIG. 7 illustrates data from performing an embodiment of a method disclosed herein. In this embodiment, participant subjects who entered via the digital interface an indication of non-completion of an activity target, were provided an activity fall back inquiry. The data indicate that participant subjects accurately entered via the digital interface subject-specific data for an activity fall back compliance parameter, as indicated by the number of entries indicating a fall back activity was not completed.
Figure 8:
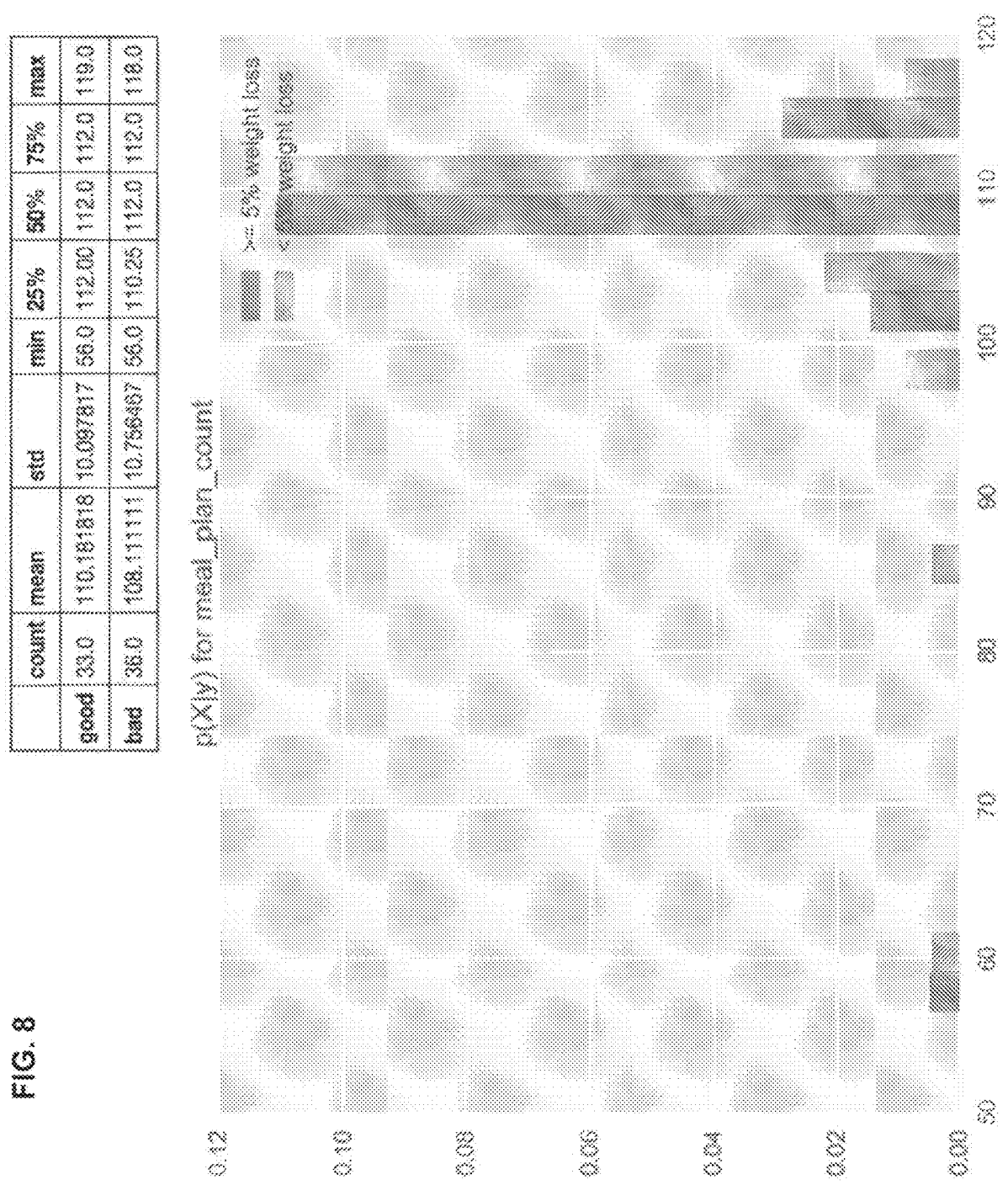
FIG. 8 illustrates data from performing an embodiment of a method disclosed herein. The data indicate that the majority of subjects who completed a lifestyle intervention regimen entered via the digital interface subject-specific data indicating a high rate and number of a meal-plan count compliance parameter.
Figure 9:
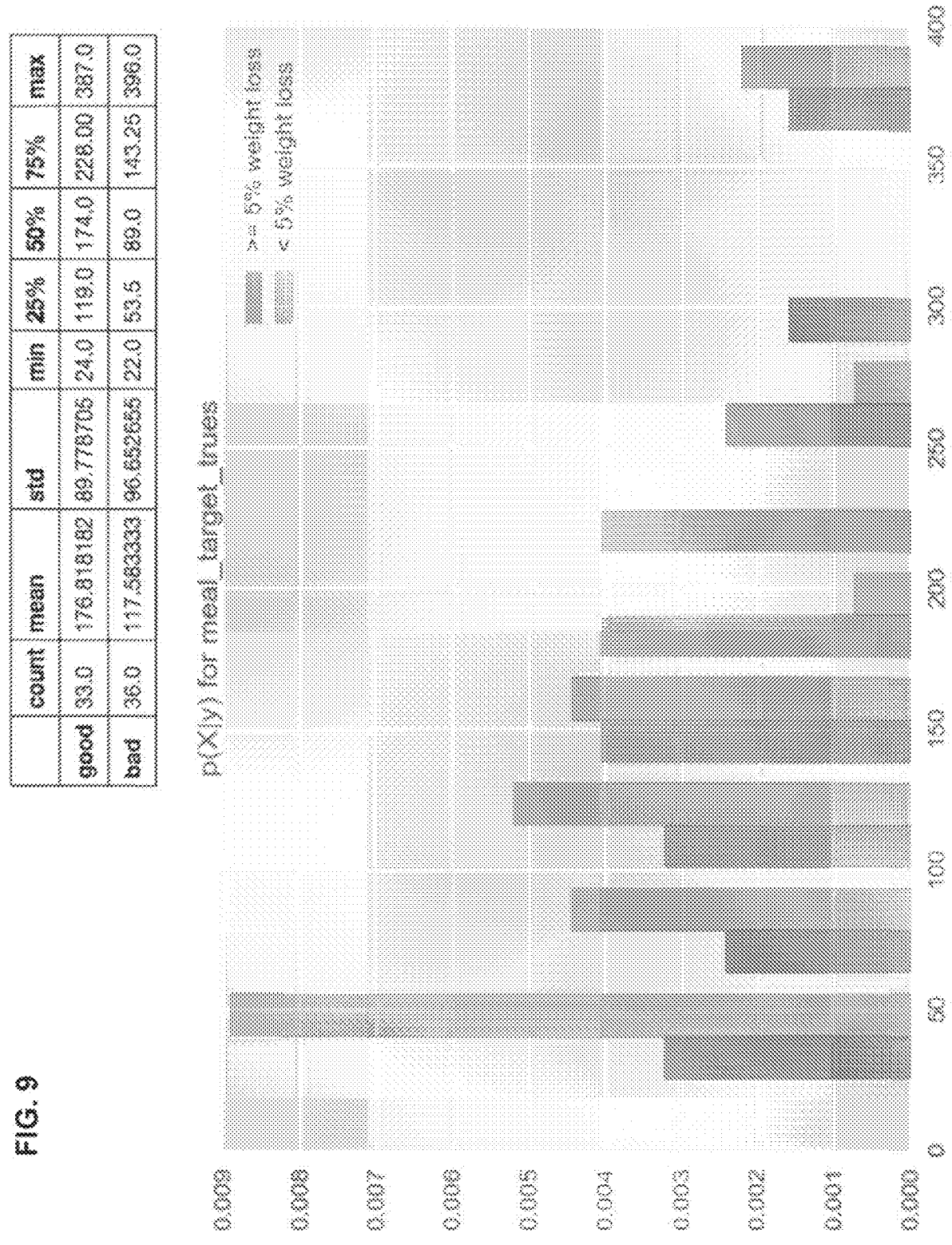
FIG. 9 illustrates data from performing an embodiment of a method disclosed herein. The data indicate that the number of entries into the digital interface that indicate completion of a meal target is positively correlated with a weight loss milestone.
Figure 10:
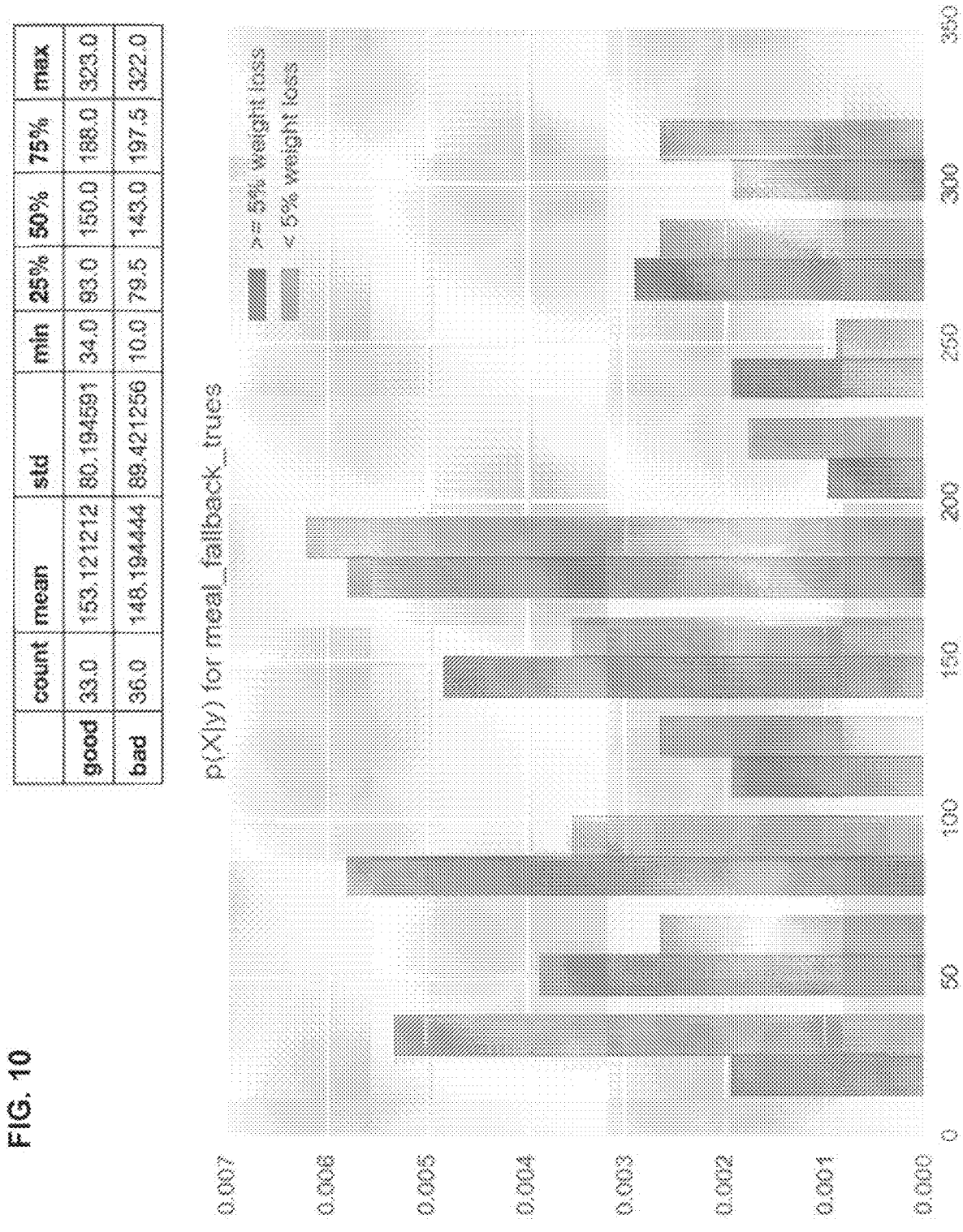
FIG. 10 illustrates data from performing an embodiment of a method disclosed herein. In this embodiment, participant subjects who entered via the digital interface an indication of non-completion of a meal plan target, were provided a meal plan fall back inquiry. The data indicate that more frequent logging of consumption of meal plan fall backs via the digital interface is positively correlated with weight loss.
Figure 11:
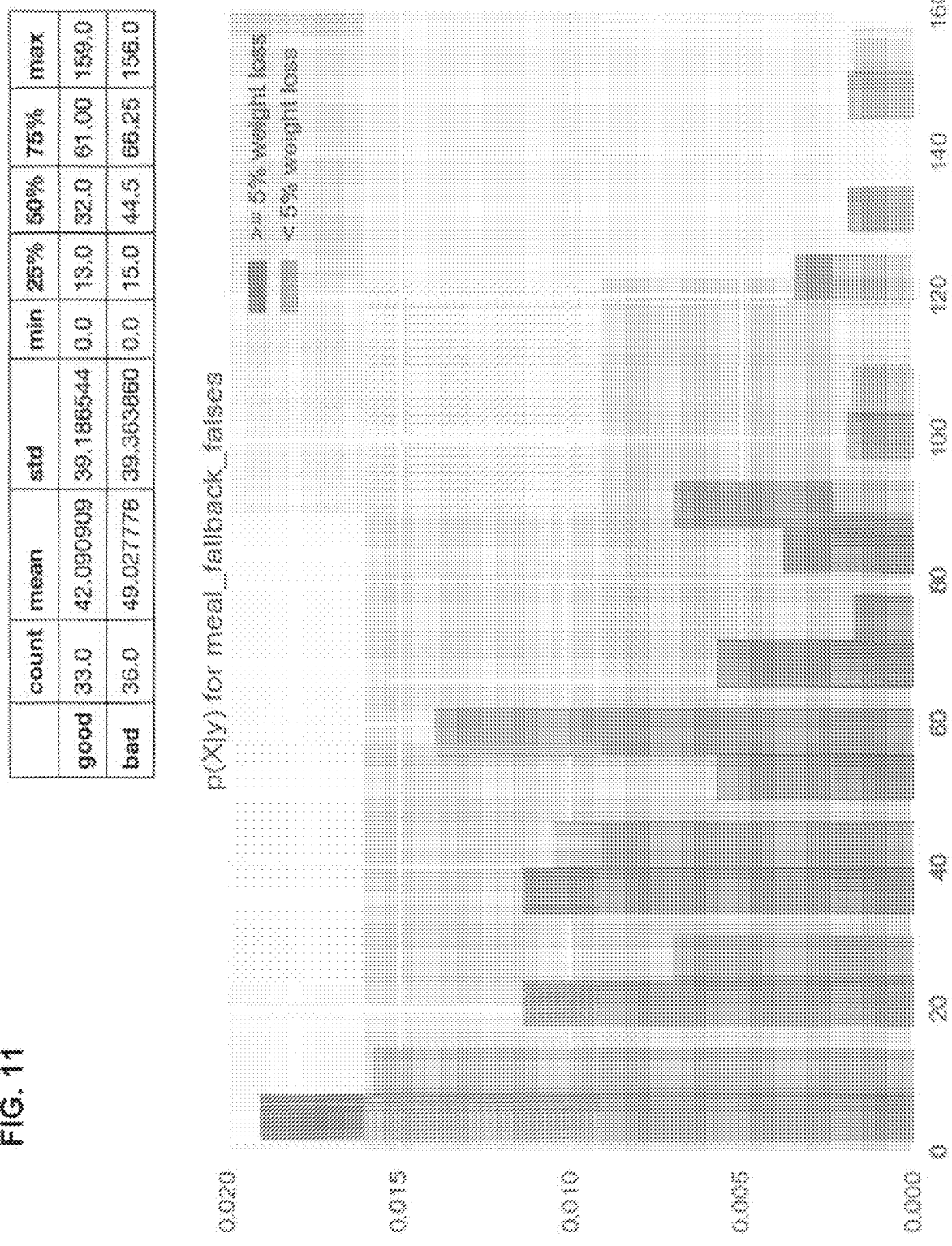
FIG. 11 illustrates data from performing an embodiment of a method disclosed herein. In this embodiment, participant subjects entered via the digital interface an indication of non-completion of a meal plan target, were provided a meal plan fall back inquiry. The data indicate that more frequent logging of non-consumption of meal plan fall backs via the digital interface is associated with a reduced amount of weight loss.
Figure 14:
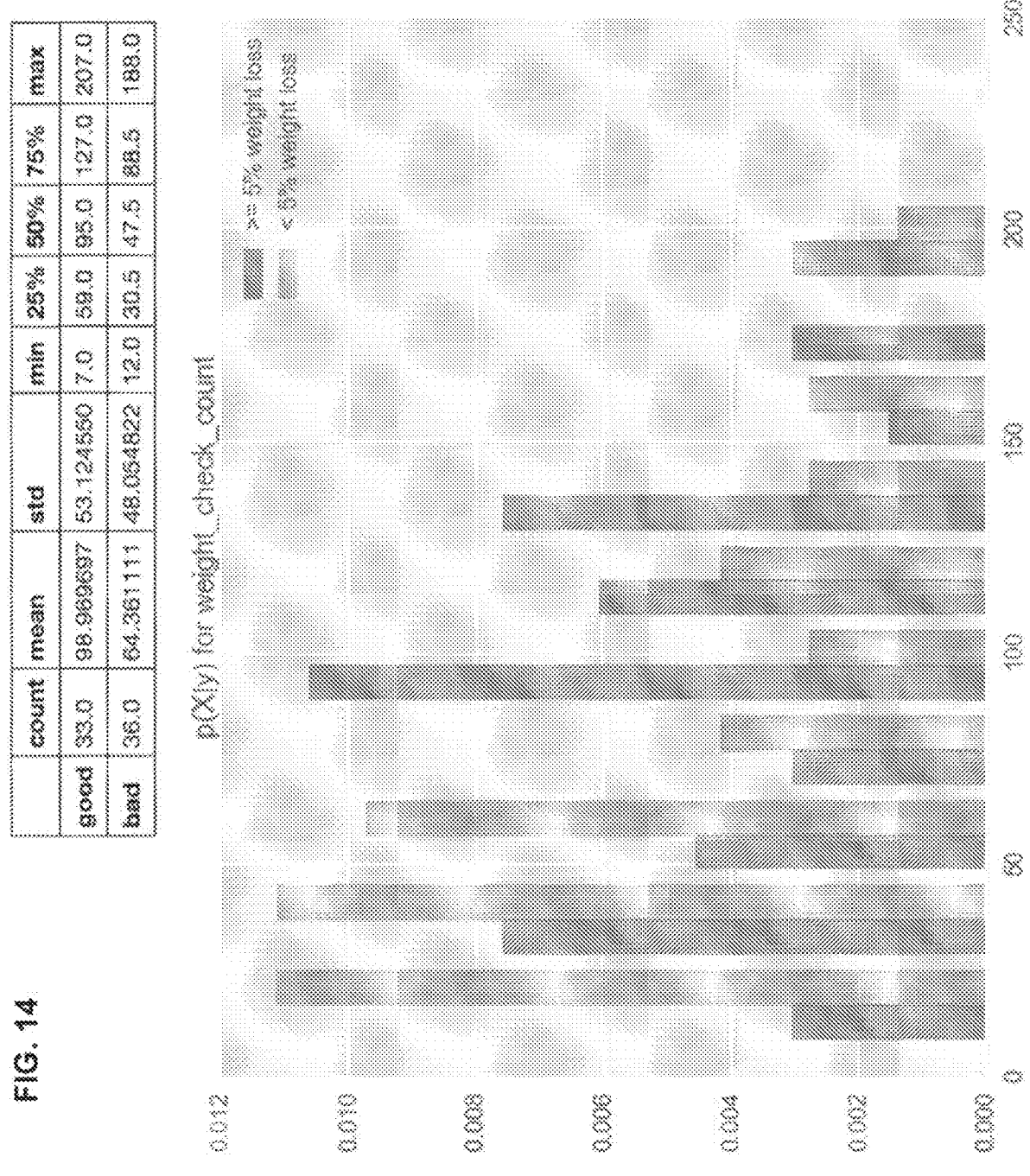
FIG. 14 illustrates data from performing an embodiment of a method disclosed herein. In this embodiment, participant subjects entered via the digital interface an indication that a body weight check was performed. The data indicate that more frequent logging of a weight check via the digital interface is positively correlated with weight loss.
Figure 15:
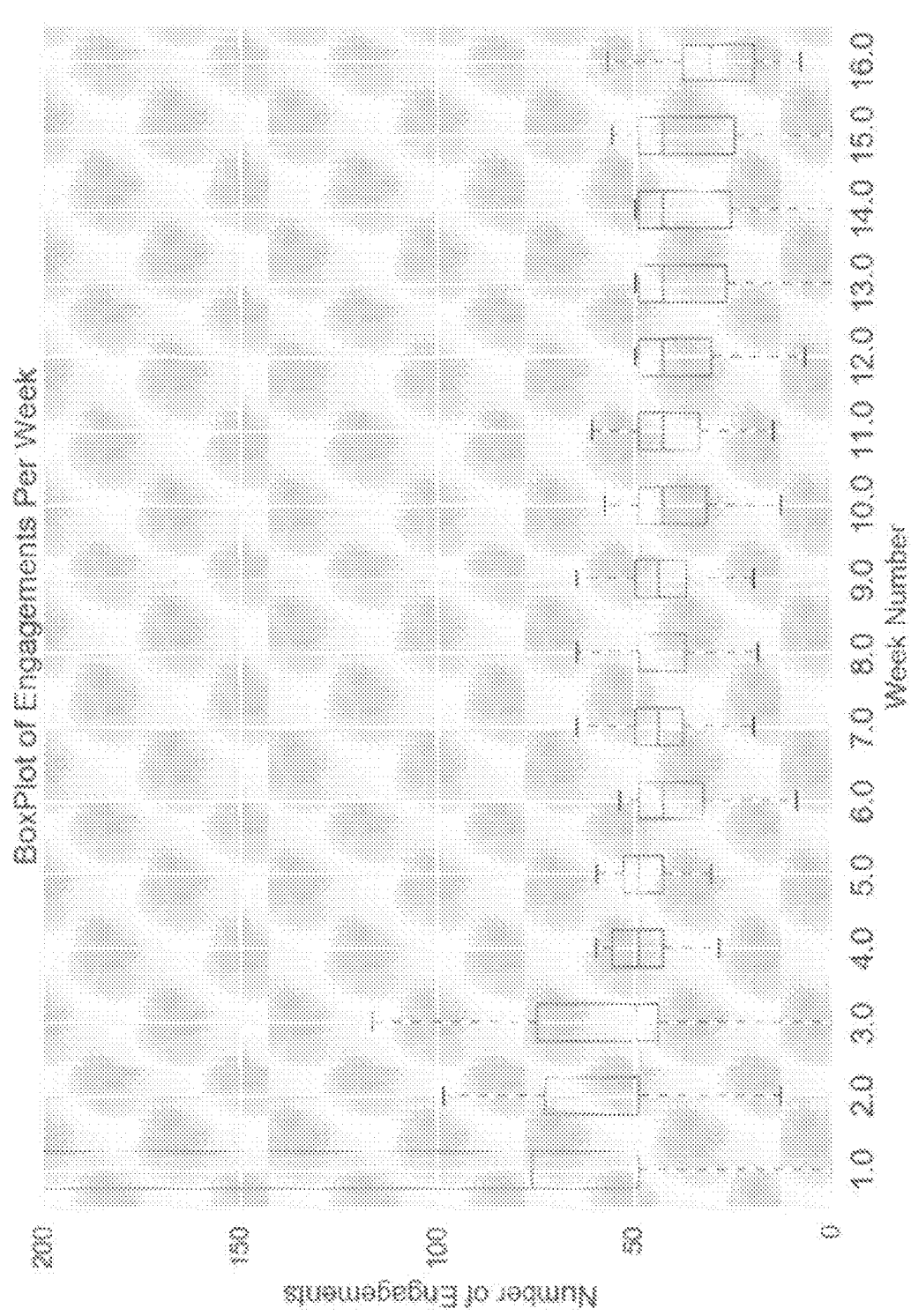
FIG. 15 illustrates data from performing an embodiment of a method disclosed herein. The number of times participant subjects engaged with the digital interface and entered at least one subject-specific datapoint per week is depicted as a boxplot. Participant subjects who completed the 16 week program exhibited a high degree of engagement throughout the program.
Figure 16:
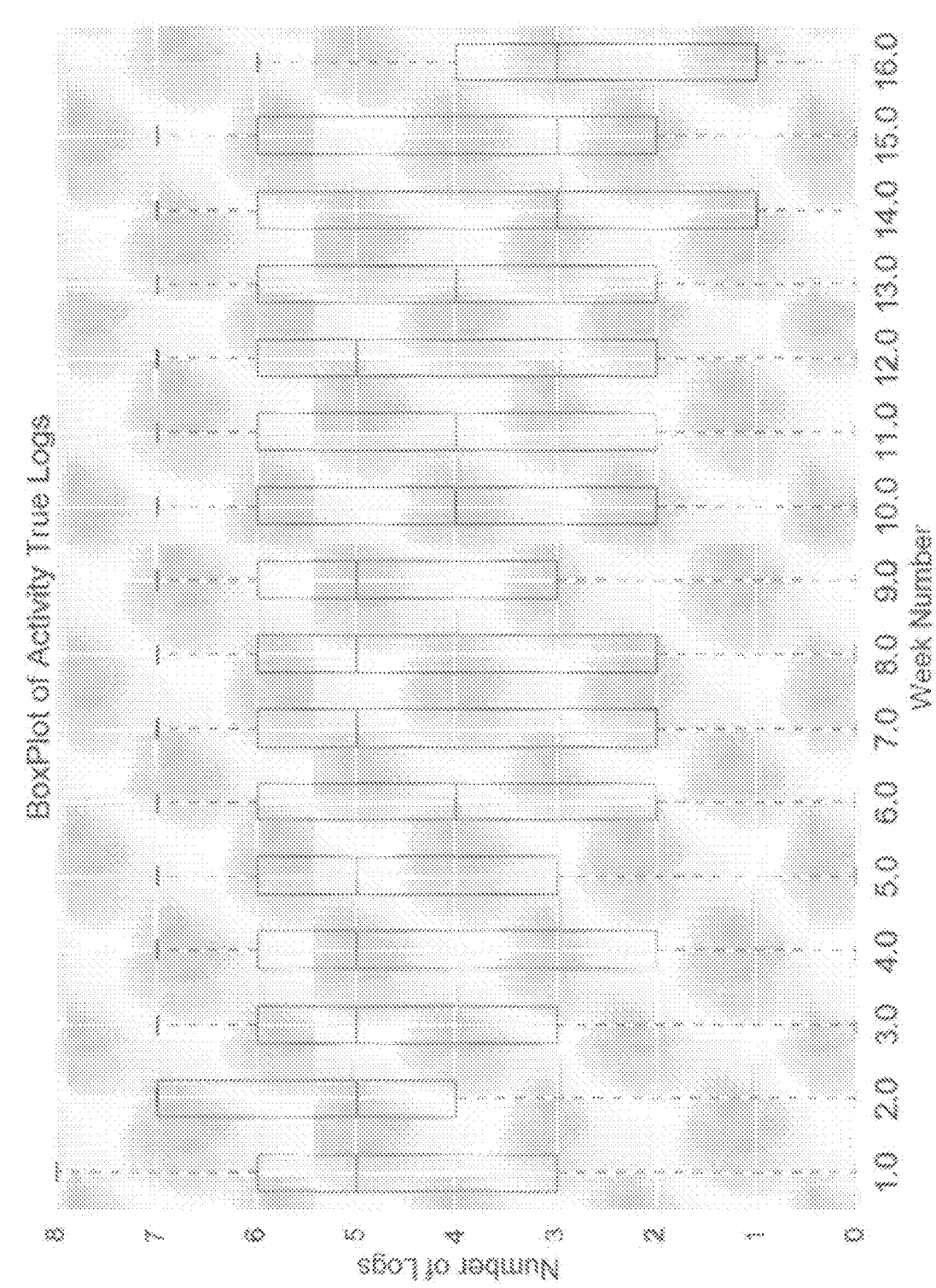
FIG. 16 illustrates data from performing an embodiment of a method disclosed herein. In this embodiment, participant subjects entered via the digital interface a log of activity. Participants who completed the lifestyle intervention regimen entered an average of 4 activity days per week.
Figure 17:
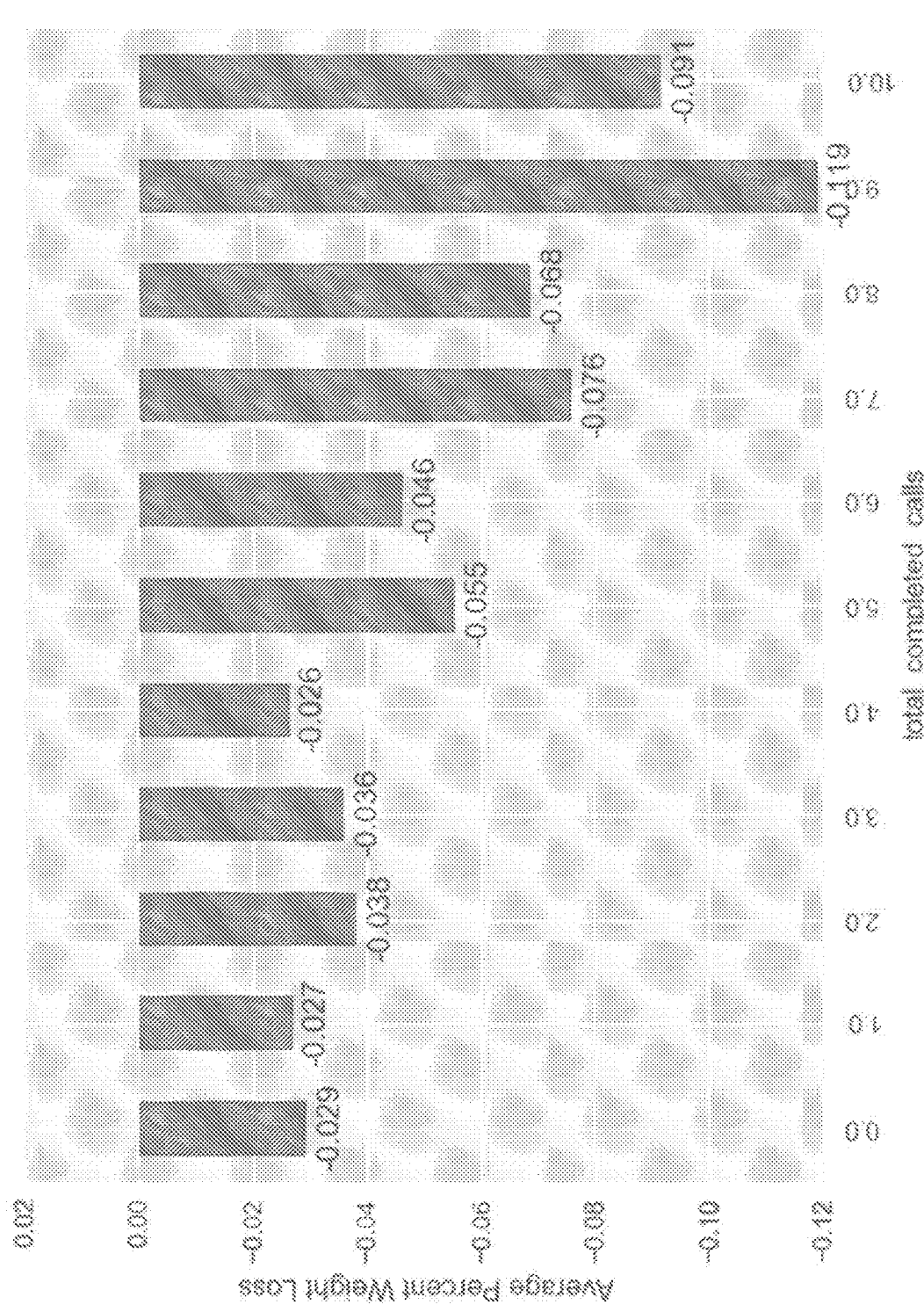
FIG. 17 illustrates data from performing an embodiment of a method disclosed herein. The number of times participant subjects entered a completed coaching call via the digital interface was positively and strongly correlated with weight loss.
Figure 18:
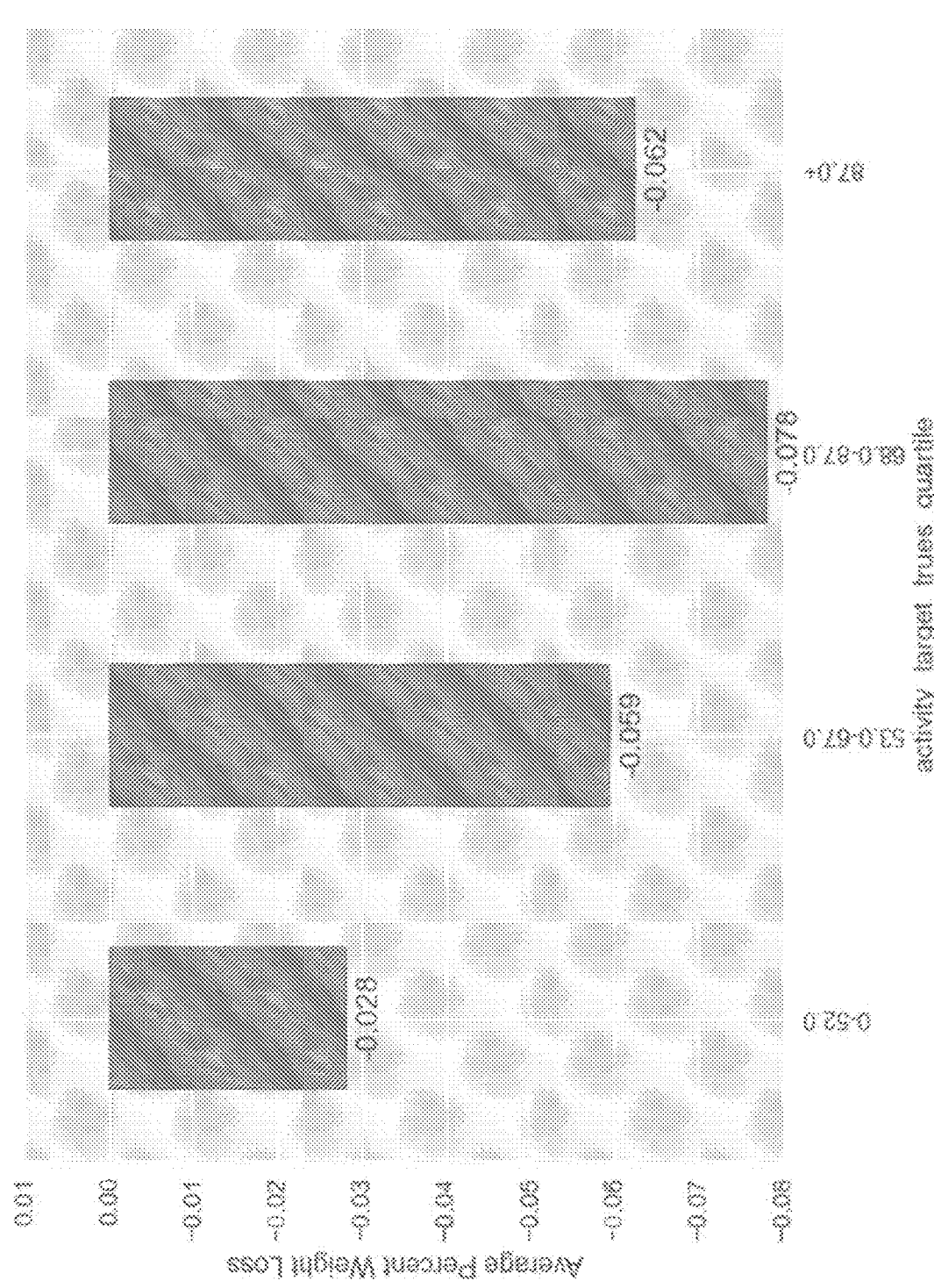
FIG. 18 illustrates data from performing an embodiment of a method disclosed herein. Logged activity data entered via the digital interface were divided into four equal sized quartiles. More frequent logging of activity via the digital interface was positively correlated with weight loss.
Figure 19:
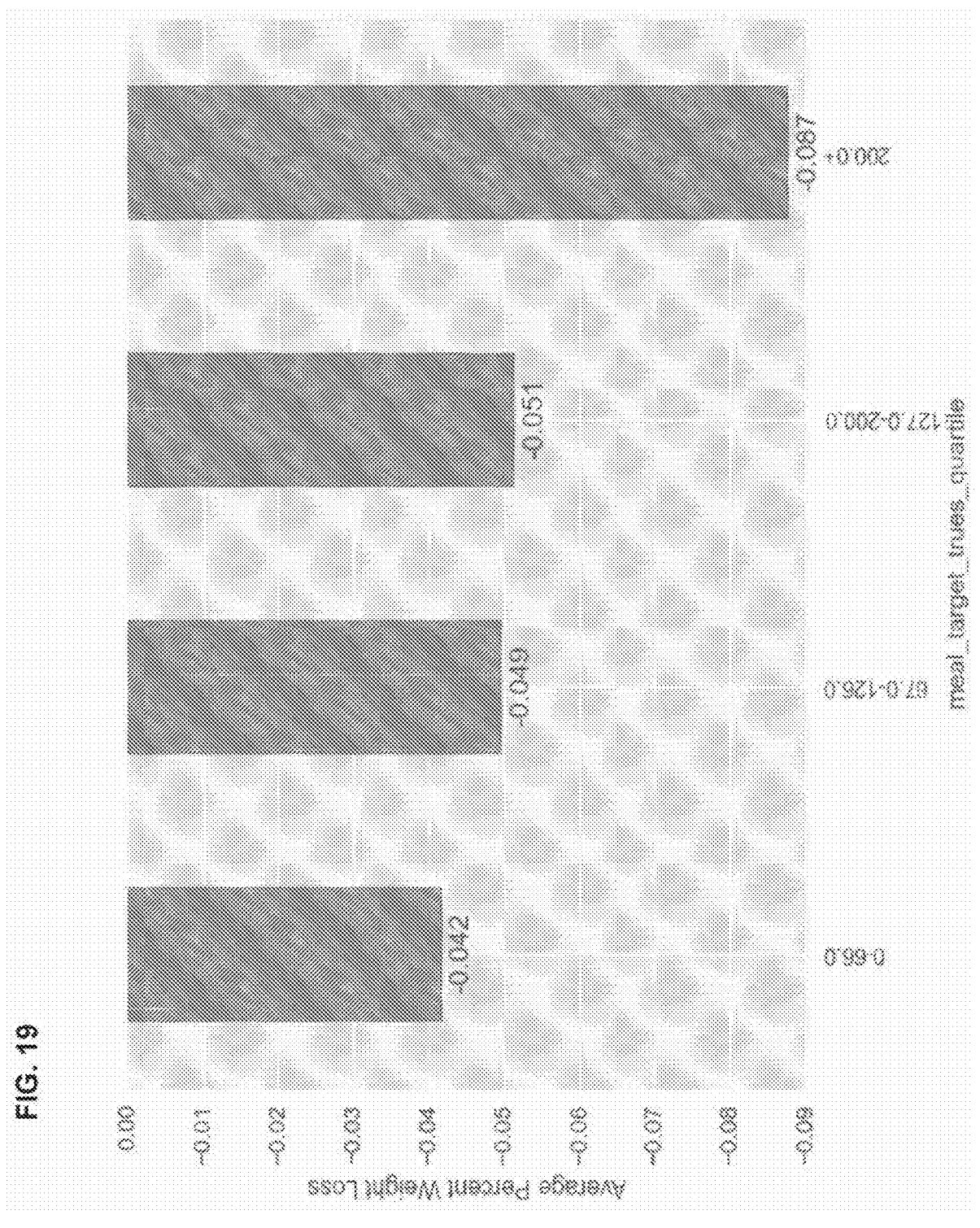
FIG. 19 illustrates data from performing an embodiment of a method disclosed herein. Meal plan use data entered via the digital interface were divided into four equal sized quartiles. More frequent logging of meal plan use via the digital interface was positively correlated with weight loss.

We explored the relationship between app use and Hemoglobin A1c change. As shown in FIG. 22, there was a stepwise decrease in Hemoglobin A1c as app engagement level increased. For example, as displayed in FIG. 1, in those with a baseline HbA1c>7.0% who did not change medications during the study period, the lowest tertile of engagers reduced HbA1c by 0.9% (SD 1.3); whereas, the highest tertile of engagers reduced HbA1c by 1.3% (SD 1.0, P=0.03 using log transformed baseline HbA1c).

Self-Efficacy 98 participants answered questions pertaining to self-efficacy. 90 participants (91.8% of those responding) reported greater confidence in their ability to manage their diabetes compared to before the program 89 participants (90.8%) reported greater confidence in their ability to maintain a healthy dietary pattern. Table 2 summarizes change in Hemoglobin A1c, diabetes medications and self-efficacy.

TABLE 2

Change in Hemoglobin A1c, diabetes medications and self-efficacy

| Measures | Value | n | P[a] |
|---|---|---|---|
| Hemoglobin A1c (%), mean change (SD) | –0.8 (1.3) | 97 | <.001 |
| Duration (months)[b], mean (SD) | 3.5 (0.8) | 97 | |
| Decrease by 0.5% of more, % | 58.8 | 57 | |
| Decrease by 1.0% of more, % | 39.2 | 38 | |
| Decrease in diabetes medication use[c], % | 16.5 | 16 | |
| Increase in diabetes medication use[c], % | 8.3 | 8 | |
| Daily mobile app engagements[d], mean (SD) | 4.3 (2.5) | 109 | |
| Diabetes self-efficacy[e], mean (SD) | 4.5 (0.6) | 98 | |
| Dietary change self-efficacy[e], mean (SD) | 4.4 (0.8) | 98 | |

[a]Comparison of baseline and end study values by paired Student's t-test
[b]Time between the baseline and end study hemoglobin A1c values
[c]Includes those who changed dose and/or number of medications used
[d]Includes use of all features in the mobile app, does not count login
[e]Rated on a 5 point Likert scale with 5 = a lot more confident and 1 = a lot less confident Discussion In this study we examined the effectiveness of a digital therapeutic delivered to participants with type 2 diabetes distributed across the United States. We found clinically meaningful reductions in both Hemoglobin A1c and the proportion of participants who reduced diabetic medication usage at the conclusion of the 12-week study period. We also observed greater glycemic control in participants with higher levels of engagement with the app.

The magnitude of Hemoglobin Ale reduction observed was comparable to those found with commonly prescribed medications (Sherifali et al. The Effect of Oral Antidiabetic Agents on A1c Levels *Diabetes Care* 33(8):1859-1864 (2010)) as well as intensive lifestyle interventions delivered in person. (Chen et al. Effect of Lifestyle Intervention in patients with type 2 diabetes: A meta-analysis *Metabolism* 64(2):338-347 (2015)) In addition, a meaningful percentage (22.7%, 22/97) of participants achieved a Hemoglobin A1c value below the diabetic range, 22.7% (5/22) of which reported no diabetic medication use, indicating potential for partial or complete remission of diabetes as defined by the ADA consensus definition. The short duration of this trial and lack of knowledge of the temporal sequence of lab test vs medication change did not allow us to conclusively evaluate remission status.

Example 3

Fifteen subjects from the 12-week study described in Example 2 were selected for an extended study to determine the durability of the clinical response observed in the results described in Example 2. The extended study was conducted for an additional 18 weeks for a total of 30 weeks. As shown in Table 3, patients who continued using the digital therapeutic exhibited sustained and improved outcomes as compared to the 12-week study results demonstrating that the methods described herein are effective for chronic treatment of chronic disorders and/or chronic lifestyle-related health conditions.

TABLE 3

| n = 15 | Mean (SD) | Min | Max |
|---|---|---|---|
| A1c at baseline | 8.6 (1.9) | 6.5 | 12.3 |
| A1c change at end intervention | −1.1 (1.5) | −3.8 | 0.8 |
| A1c change since baseline | −1.4 (1.8) | −4.8 | 1.3 |
| Weeks since baseline | 23.9 (3.8) | 18.0 | 33.4 |
| A1c change since week 12 | −0.3 (1.2) | −1.0 | 3.8 |

Of the 15 who participated in extension, 6 have A1c values that are in the pre-diabetes mellitus range (DM): 2 of these people started in this group at baseline, 1 moved into this range during the 12 week study, 3 moved into this range during the extension (FIG. 23).

Example 4

In this study, we sought to understand to what degree a novel, skill-focused, digital therapeutic program could reduce diastolic and/or systolic blood pressure in hypertensive subjects.

Methods

Eligibility criteria for participants included having a self-reported diagnosis of hypertension, a baseline systolic blood pressure (BP) of at least 130 mmHg and a diastolic blood pressure of at least 80 mmHg measured within 14 days of program start, and possession of an Android or iPhone Smartphone, as demonstrated by the ability to download the intervention app. Participants were excluded if they were not able to comply with the study protocol, for example if they could not speak or read English or did not have sufficient computer literacy to operate the app successfully.

Table 4 shows the results for participants who completed at least one coach call during the study period. Change in systolic and diastolic blood pressure were calculated as the average of the most recent values available within 48 hours of each other minus the baseline average value. Blood pressure duration was calculated as the number of days between the first value and the most recent value. Results are presented in graphic form in FIG. 24.

TABLE 4

| Variable | N | Mean | Std Dev | Min | Max | N Miss |
|---|---|---|---|---|---|---|
| Initial Systolic BP avg | 41 | 138.5 | 12.7 | 115 | 169 | 0 |
| Final Systolic BP avg | 41 | 129.8 | 12.3 | 108 | 159 | 0 |
| Initial Diastolic BP avg | 41 | 86.3 | 7.7 | 65 | 102 | 0 |
| Final Diastolic BP avg | 41 | 81.0 | 10.5 | 60 | 104 | 0 |

TABLE 4-continued

| Variable | N | Mean | Std Dev | Min | Max | N Miss |
|---|---|---|---|---|---|---|
| Change in Systolic | 41 | −8.7 | 12.3 | −52 | 10.5 | 0 |
| Change in Diastolic | 41 | −5.3 | 9.3 | −31 | 15 | 0 |
| Duration | 41 | 51.6 | 29.7 | 4 | 91 | 0 |

Tertile analysis was performed to analyze the correlation between app use engagement on reduction in blood pressure. 38 of the 41 participants produced app use data and were included in the tertile analysis. As shown in Tables 5 and 6, the lowest tertile of engagement showed significantly less reduction in both systolic (Table 5) and diastolic (Table 6) blood pressure as compared to the highest tertile of engagement.

TABLE 5

| | | | | | | |
|---|---|---|---|---|---|---|
| Systolic Blood Pressure | | | | | | |
| Tertile | N | Mean | Std Dev | Min | Max | N Miss |
| First (lowest engagement) | 12 | −4.7 | 13.1 | −28 | 10.5 | 0 |
| Second | 13 | −11.15 | 15.2 | −52 | 5.5 | 0 |
| Third | 13 | −10.7 | 9.3 | −30 | 6.7 | 0 |

TABLE 6

| | | | | | | |
|---|---|---|---|---|---|---|
| Diastolic Blood Pressure | | | | | | |
| Tertile | N | Mean | Std Dev | Min | Max | N Miss |
| First (lowest engagement) | 12 | −2.3 | 6.6 | −10.3 | 15 | 0 |
| Second | 13 | −5.7 | 11.0 | −24 | 7 | 0 |
| Third | 13 | −9.2 | 9.6 | −31 | 3 | 0 |

Results were also stratified by baseline systolic blood pressure. As illustrated in Tables 7-8, subjects exhibiting a higher baseline blood pressure received a greater reduction in blood pressure, demonstrating that both stage 1 and stage 2 hypertensive subjects benefit from the digital therapeutics described herein.

TABLE 7

| | | | | | | |
|---|---|---|---|---|---|---|
| Systolic Blood Pressure Stage 1 | | | | | | |
| Variable | N | Mean | Std Dev | Min | Max | N Miss |
| Initial Systolic Avg | 18 | 129.0 | 4.2 | 122 | 135.8 | 0 |
| Initial Diastolic Avg | 18 | 82.7 | 6.4 | 65 | 89 | 0 |
| Change in Systolic | 18 | −3.5 | 9.1 | −23 | 10.5 | 0 |
| Change in Diastolic | 18 | −1.9 | 6.5 | −12.3 | 15 | 0 |
| Duration | 18 | 45.4 | 30.0 | 7 | 88 | 0 |

TABLE 7

| | | | | | | |
|---|---|---|---|---|---|---|
| Systolic Blood Pressure Stage 2 | | | | | | |
| Variable | N | Mean | Std Dev | Min | Max | N Miss |
| Initial Systolic Avg | 23 | 146.0 | 12.1 | 115 | 169 | 0 |
| Initial Diastolic Avg | 23 | 89.1 | 7.6 | 68 | 102 | 0 |

43

TABLE 7-continued

| | | | Systolic Blood Pressure Stage 2 | | | |
|---|---|---|---|---|---|---|
| Variable | N | Mean | Std Dev | Min | Max | N Miss |
| Change in Systolic | 23 | −12.8 | 13.1 | −52 | 7.7 | 0 |
| Change in Diastolic | 23 | −8.0 | 10.4 | −31 | 7 | 0 |
| Duration | 23 | 56.4 | 29.2 | 4 | 91 | 0 |

While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for communicating with user devices over networked environments, comprising:

at least one server having one or more processors coupled with memory, configured to:

provide, to a user device over a communication network, an instruction to present a graphical user interface (GUI) on a user device to prompt a user to input values for a set of compliance parameters for events on the user device according to a data protocol;

receive, from the user device, a plurality of values for the set of compliance parameters inputted via the GUI for the events on the user device;

store, in one or more data structures, the plurality of values for the set of compliance parameters;

track, based on inputting via the GUI, a completion status of at least one of the set of compliance parameters corresponding to at least one event corresponding with achieving a target;

determine, based on tracking, a metric associated with a rate or quality of the plurality of values for the set of compliance parameters;

apply the metric into a machine learning model to generate a likelihood to satisfy a target associated with the data protocol, wherein generating the likelihood comprises comparing the metric to a reference metric of a reference set of users; and responsive to the likelihood not satisfying a threshold, transmit to the user device over the communication network, a subsequent instruction to prompt the user to input values for the set of compliance parameters for events on the user device according to the data protocol.

2. The system of claim 1, wherein the at least one server is further configured to apply the plurality of values and the metric to the machine learning model having one or more weights to (i) identify patterns in user inputs associated with at least one target associated with the data protocol and (ii) generate the likelihood based on the identified patterns.

3. The system of claim 1, wherein the at least one server is further configured to determine, based on inputting via the GUI, the metric comprising at least one of a frequency of inputting or a number of inputting by the user.

4. The system of claim 1, wherein the at least one server is further configured to generate, in response to the likelihood being below a threshold, the subsequent instruction to prompt the user to input the values for the set of compliance parameters via the GUI according to the data protocol.

5. The system of claim 1, wherein the at least one server is further configured to present, in response to the likelihood being below a threshold, the subsequent instruction in a messaging interface with an automated chatbot via the GUI on the user device to prompt the user to enter inputs.

6. The system of claim 1, wherein the at least one server is further configured to monitor for inputs via the GUI corresponding to the plurality of values for the set of compliance parameters for events on the user device.

7. The system of claim 1, wherein the at least one server is further configured to validate the set of compliance parameters as associated with the target of the data protocol.

8. A method of communicating with user devices over networked environments, comprising:

providing, by a server to a user device over a communication network, an instruction to present a graphical user interface (GUI) on a user device to prompt a user to input values for a set of compliance parameters for events on the user device according to a data protocol;

receiving, by the server from the user device, a plurality of values for the set of compliance parameters inputted via the GUI for the events on the user device;

storing, by the server, in one or more data structures, the plurality of values for the the set of compliance parameters;

tracking, by the server from the user device, based on inputting via the GUI, a completion status of at least one of the set of compliance parameters corresponding to at least one event corresponding with achieving a target;

determining, by the server, based on tracking, a metric associated a rate or quality of the plurality of values for the set of compliance parameters;

applying, by the server, metric into a machine learning model to generate a likelihood to satisfy a target associated with the data protocol, wherein generating the likelihood comprises comparing the metric to a reference metric of a reference set of users; and transmitting, by the server to the user device over the communication network responsive to the likelihood not satisfying a threshold, a notification comprising a subsequent instruction to prompt the user to input values for the set of compliance parameters via the GUI according to the data protocol.

9. The method of claim 8, wherein applying to the machine learning model further comprises applying the plurality of values and the metric to the machine learning model having one or more weights to (i) identify patterns in inputs associated with at least one target associated with the data protocol and (ii) generate the likelihood based on the identified patterns.

10. The method of claim 8, wherein determining the metric further comprises determining, based on inputting via the GUI, the metric comprising at least one of a frequency of inputting or a number of inputting of the plurality of values for the set of compliance parameters by the user.

11. The method of claim 8, wherein transmitting the subsequent instruction further comprises generating, in response to the likelihood being below the threshold, the subsequent instruction to prompt the user to input the values for the set of compliance parameters via the GUI according to the data protocol.

12. The method of claim 8, wherein transmitting the subsequent instruction further comprises generating, in response to the likelihood being below the threshold, the subsequent instruction to present a messaging interface with an automated chatbot via the GUI on the user device to prompt the user to enter inputs.

13. The method of claim 8, further comprising monitoring, by the server, for inputs via the GUI corresponding to the plurality of values for the the set of compliance parameters for events on the user device.

14. The method of claim 8, further comprising validating, by the server, the set of compliance parameters as associated with the target of the data protocol.

* * * * *